(12) United States Patent
Brew et al.

(10) Patent No.: US 10,016,437 B2
(45) Date of Patent: *Jul. 10, 2018

(54) DRUG COMBINATIONS AND USES IN TREATING A COUGHING CONDITION

(71) Applicant: Infirst Healthcare Limited

(72) Inventors: John Brew, London (GB); Robin Mark Bannister, London (GB)

(73) Assignee: Infirst Healthcare Limited, London (GB)

(*) Notice: Subject to any disclaimer, the term of this patent is extended or adjusted under 35 U.S.C. 154(b) by 0 days.

This patent is subject to a terminal disclaimer.

(21) Appl. No.: 14/287,017

(22) Filed: May 24, 2014

(65) Prior Publication Data

US 2014/0256752 A1 Sep. 11, 2014

Related U.S. Application Data

(63) Continuation-in-part of application No. 13/446,217, filed on Apr. 13, 2012, which is a continuation-in-part of application No. PCT/GB2011/051610, filed on Aug. 25, 2011, and a continuation-in-part of application No. PCT/GB2010/052085, filed on Dec. 14, 2010, and a continuation-in-part of application No. PCT/GB2010/052086, filed on Dec. 14, 2010, and a continuation-in-part of application No. PCT/GB2010/051895, filed on Nov. 12, 2010, and a continuation-in-part of application No. PCT/GB2010/051896, filed on Nov. 12, 2010, and a continuation-in-part of application No. PCT/GB2010/050997, filed on Jun. 15, 2010.

(30) Foreign Application Priority Data

| Jun. 16, 2009 | (GB) | 0910375.5 |
|---|---|---|
| Nov. 13, 2009 | (GB) | 0919889.6 |
| Nov. 13, 2009 | (GB) | 0919893.8 |
| Dec. 14, 2009 | (GB) | 0921803.3 |
| Dec. 14, 2009 | (GB) | 0921805.8 |
| Aug. 27, 2010 | (GB) | 1014391.5 |
| Jul. 5, 2011 | (GB) | 1111485.7 |

(51) Int. Cl.
| A61K 31/522 | (2006.01) |
|---|---|
| A61K 31/485 | (2006.01) |
| A61K 31/138 | (2006.01) |
| A61K 31/137 | (2006.01) |
| A61K 45/06 | (2006.01) |

(52) U.S. Cl.
CPC .......... *A61K 31/522* (2013.01); *A61K 31/137* (2013.01); *A61K 31/138* (2013.01); *A61K 45/06* (2013.01)

(58) Field of Classification Search
USPC .................................................. 514/263.34
See application file for complete search history.

(56) References Cited

U.S. PATENT DOCUMENTS

| 5,100,898 A | 3/1992 | Sorrentino |
|---|---|---|
| 6,348,470 B1 | 2/2002 | Korbonits et al. |
| 6,417,206 B1 | 7/2002 | Leflein et al. |
| 7,166,640 B2 | 1/2007 | Berg |
| 2002/0052312 A1 | 5/2002 | Reiss et al. |
| 2003/0206942 A1 | 11/2003 | Kulkarni et al. |
| 2004/0122027 A1* | 6/2004 | Gonzales ............ A61K 31/135 514/255.04 |
| 2004/0202677 A1 | 10/2004 | Hopkins et al. |
| 2004/0204440 A1 | 10/2004 | Staniforth et al. |
| 2005/0220897 A1 | 10/2005 | Hack et al. |
| 2006/0148837 A1 | 7/2006 | Giordano et al. |
| 2007/0160689 A1 | 7/2007 | Giordano et al. |
| 2007/0249566 A1* | 10/2007 | Martin et al. ................. 514/165 |
| 2008/0003280 A1* | 1/2008 | Levine et al. ................ 424/456 |
| 2008/0014267 A1 | 1/2008 | Giordano et al. |
| 2008/0085312 A1 | 4/2008 | Wilson et al. |
| 2008/0176955 A1 | 7/2008 | Heck et al. |
| 2008/0220078 A1 | 9/2008 | Morton et al. |
| 2009/0136427 A1 | 5/2009 | Croft et al. |
| 2009/0220594 A1 | 9/2009 | Field |
| 2012/0128738 A1 | 5/2012 | Brew et al. |
| 2012/0252824 A1 | 10/2012 | Brew et al. |

FOREIGN PATENT DOCUMENTS

| CN | 1593451 | 3/2005 |
|---|---|---|
| CN | 101024014 A | 8/2007 |
| CN | 101112383 B | 5/2010 |
| DE | 4420708 A1 | 12/1995 |
| EP | 2050435 B1 | 4/2009 |
| GB | 2114001 A | 8/1983 |
| GB | 2284761 A | 6/1995 |
| GB | 2424185 B | 9/2006 |

(Continued)

OTHER PUBLICATIONS

Bjornsdottir (efficacy of diphenhydramine against cough in humands: a review, Pharm world Sci, 2007, 29, 29 pp. 577-583).*
Cough: Causes, Mechanisms and Therapy, pp. 318 (eds. Chung, et al., 2003).
Forsberg, et al., Selective Inhibition of Cough and Bronchoconstriction in Conscious Guinea Pigs, Respiration 59: 72-76 (1992).
Levine, A Novel Treatment of Chronic Unexplained Cough, Chest J. 134(4 Meeting Abstracts): s17003 (2008).
Murao, et al., Intoxication with Over-the-Counter Antitussive Medication Containing Dihydrocodeine and Chlorpheniramine Causes Generalized Convulsion and Mixed Acidosis, Inter. Med. 47: 1013-1015 (2008).
Nickitas-Etienne, PCT International Preliminary Report on Patentability, PCT/GB2012/050816, pp. 9, dated Jan. 7, 2014
Packman, et al., Antitussive Effects of Diphenhydramine on the Citric Acid Aerosol-Induced Cough Response in Humans, Int. J. Clin. Pharmacol. Ther. Toxicol. 29(6): 218-222 (1991).

(Continued)

*Primary Examiner* — Kathrien A Cruz
(74) *Attorney, Agent, or Firm* — Ultimatedge IP Law Group, P.C.; Dean G. Stathakis

(57) ABSTRACT

The present specification discloses compositions comprising a plurality of therapeutic compound having antitussive activity and methods and uses for treating a coughing condition with such compositions.

10 Claims, No Drawings

(56) References Cited

FOREIGN PATENT DOCUMENTS

| | | | |
|---|---|---|---|
| GB | 2442828 | A | 4/2008 |
| JP | 62-249924 | A | 10/1987 |
| JP | H10-316568 | A | 12/1998 |
| JP | 2001-518928 | A | 10/2001 |
| JP | 2002193839 | A | 7/2002 |
| JP | 2003-012514 | A | 1/2003 |
| JP | 2003055258 | A | 2/2003 |
| JP | 2003128549 | A | 5/2003 |
| JP | 2003-321357 | A | 11/2003 |
| JP | 2005-516917 | A | 6/2005 |
| JP | 2008031146 | A | 2/2008 |
| KR | 2008009994 | A | 1/2008 |
| WO | 19891003213 | A1 | 4/1989 |
| WO | 19951007103 | A1 | 3/1995 |
| WO | 19981042322 | A2 | 10/1998 |
| WO | WO 98/42322 | * | 10/1998 |
| WO | 20001000212 | A1 | 1/2000 |
| WO | 20001030715 | A1 | 6/2000 |
| WO | 20111058373 | A2 | 5/2003 |
| WO | 2004058236 | A1 | 7/2004 |
| WO | 2006064780 | A1 | 6/2006 |
| WO | 20061059152 | A2 | 6/2006 |
| WO | 20081002514 | A2 | 1/2008 |
| WO | 2008089260 | A2 | 7/2008 |
| WO | 2009019598 | A2 | 2/2009 |
| WO | 20101146394 | A1 | 12/2010 |
| WO | 20111058374 | A1 | 5/2011 |
| WO | 20111073646 | A1 | 6/2011 |
| WO | 20111073647 | A1 | 6/2011 |
| WO | 20121025761 | A1 | 3/2012 |
| WO | 20131004999 | A1 | 1/2013 |

OTHER PUBLICATIONS

Small, et al., The Releaxant and Spasmogenic Effects of Some Xanthine Derivatives Acting on Guinea-Pig Isolated Trachealis Muscle, Br. J. Pharmacol. 94: 1091-1100 (1988).
Balsamo, et al. Mucoactive drugs, European Respiratory Review, 2010, vol. 19, No. 116, p. 127-133.
Rogers, Mucoactive Agents for Airway Mucus Hypersecretory Diseases, Respiratory Care, Sep. 2007, vol. 52, No. 9, p. 1176-1197.
Wangemann, Notes from Practice Clinical Experiences with the Asthma Drug Dyspnoced, from the 2nd Internal Division of the Westend Hospital, Berlin-Charlottenburg (Head physician: Dr. A. Tietze).
Abstracts: Presented At Poster Sessions, Annals of Allergy, Asthma & Immunology, USA, Jan. 1, 2009, V102 N1, p. A23, A25-A128.
Brown, et al, "Antitussive activity of sigma-1 receptor agonists in the guinea-pig" Br. J. Pharmacol., 2004, vol. 141, No. 2, p. 233-240.
Database WPI, Week 200343, Thomson Scientific, London, GB, AN 2005-704785 & CN 1 593 451 (Yang X) Mar. 16, 2005.
Database WPI, Week 200308, Thomson Scientific, London, GB, AN 2003-078587 & JP 2002-193839 (Meiji) Jul. 10, 2002.
Database WPI, Week 200343, Thomson Scientific, London, GB, AN 2003-451953 & JP 2003-055258 (Rohto) Feb. 26, 2003.
Dicpinigaitis, et al., Currently Available Antitussives. Pulmonary Pharmacology & Therapeutics 22(2): 148-151 (2009).
Gallico, et al, "Moguisteine: a novel peripheral non-narcotic antitussive drug" Br. J. Phamacol. (1994), 112, 795-800.
Grattan, et al., "The effect of inhaled and oral dextromethorphan on citric acid induced cough in man" Br. J. Clin. Pharmacol., 1995, vol. 39, No. 3, p. 261-263.
Levine, A Novel Treatment of Chronic Unexplained Cough, Abstract P331, Annals of Allergy, Asthma & Immunology 102(1): A113 (2009).
Minamizawa, et al., Effect of d-Psuedophedrine on Cough Reflex and its Mode of Action in Guinea Pigs, Journal of Pharmacological Sciences 102(1): 136-142 (2006).
Nickitas-Etienne, PCT International Preliminary Report on Patentability, PCT/GB2010/050997, pp. 9, dated Dec. 16, 2011.
Nickitas-Etienne, PCT International Preliminary Report on Patentability, PCT/GB2010/051895, pp. 10, dated May 15, 2012.
Nickitas-Etienne, PCT International Preliminary Report on Patentability, PCT/GB2010/051896, pp. 10, dated May 15, 2012.
Nickitas-Etienne, PCT International Preliminary Report on Patentability, PCT/GB2010/052085, pp. 9, dated Jun. 19, 2012.
Nickitas-Etienne, PCT International Preliminary Report on Patentability, PCT/GB2010/052086, pp. 6, dated Jun. 19, 2012.
Nickitas-Etienne, PCT International Preliminary Report on Patentability, PCT/GB2011/051610, pp. 13, dated Mar. 5, 2013.
Usmani, et al., "Theobromine inhibits sensory nerve activation and cough" FASEB J., 2005, vol. 19, No. 2, p. 231-233.
Usmani, et al., "Theobromine inhibits sensory nerve activation and cough" FASEB J., Nov. 17, 2004 p. 1-16.
Usmani, et al., Theobromine Inhibits Sensory Nerve Activation and Cough, FASEB Journal, pp. 1-16, online publication Nov. 2004.
Wangemann G. Klinische Erfahrungen über das Asthmamittel Dyspnoced, Arztliche Wochenschrift, 1950, vol. 5(17), p. 272-273.
Wangemann, Clinical Experience with Dyspnocedy an Anti-Athma Drug, Arztliche Wochenschrift 5(17): 272-273 (1950).
Paul et al., Effect of Dextromethorphan, Diphenhydramine, and Placebo on Nocturnal Cough and Sleep Quality for Coughing Children and Their Parents, Pediatrics vol. 114 No. 1 Jul. 2004.
Smith et al., Over-the-counter (OTC) medications for acute cough in children and adults in ambulatory settings (Review), The Cochrane Collaboration. Published by John Wiley & Sons, Ltd. 2012, Issue 8.
Yoder et al., Child Assessment of Dextromethorphan, Diphenhydramine, and Placebo for Nocturnal Cough Due to Upper Respiratory Infection, Clin Pediatr. 2006;45:633-640.
Kane et al. "Molecular Recognition of Opioid Receptor Ligands", AAPS Journal, 8 (1): E126-E137, 2006.
Knapp et al. "Molecular Biology and Pharamology of Cloned Opioid Receptors", The FASEB Journal, 9: 516-525, Apr. 1995.
Law et al. "Regulation of Opioid Receptor Activities", The Journal of Pharmacology and Experimental Therapeutics, 289(2): 607-624, 1999.
Smith et al. "Antitussive Effects of Memantine", CHEST Original Research, 141: 996-1002, Apr. 4, 2012.
Bastian, R.W., "Sensory neuropathic cough: a common and treatable cause of chronic cough," Otolaryngol Head Nck Surgery, vol. 135, No. 1, pp. 17-21, (2006).
Borja, J.M., et al., "Maculopapular exanthema from diacetylmidecamycin," Allergy Net, (MOM), (1998).
JP Article, pp. 625-637 (2003).
Menthol Use This One (Menthol also called peppermint Camphor or Mint Camphor) is obtained from oil of peppermint (species *Mentha peperita*)or Japanese or Chinese (also called commint) oil of peppermint (species *Mentha arvensis*) (1995), pp. 1-5.
Ormerod, et al.,"Ascorbic Acid (Vitamin C) Treatment of Whooping Cough," The Canadian Medical Association Journal, (Aug. 1937) vol. 37, No. 2, pp. 134-136.

* cited by examiner

DRUG COMBINATIONS AND USES IN TREATING A COUGHING CONDITION

This continuation-in-part application claims priority pursuant to 35 U.S.C. § 120 to U.S. patent application Ser. No. 13/446,217, filed Apr. 13, 2012, a continuation-in-part application of International patent Application PCT/GB2011/051610, filed Aug. 25, 2011, which claims priority to GB Provisional 1014391.5, filed Aug. 27, 2010; International patent Application PCT/GB2010/052085, filed Dec. 14, 2010, which claims priority to GB Provisional 0921805.8, filed Dec. 14, 2009; International patent Application PCT/GB2010/052086, filed Dec. 14, 2010, which claims priority to GB Provisional 0921803.3, filed Dec. 14, 2009; International patent Application PCT/GB2010/051895, filed Nov. 12, 2010, which claims priority to GB Provisional 0919889.6 filed Nov. 13, 2009; International patent Application PCT/GB2010/051896, filed Nov. 12, 2010, which claims priority to GB Provisional 0919893.8 filed Nov. 13, 2009; International patent Application PCT/GB2010/050997, filed Jun. 15, 2010, which claims priority to GB Provisional 0910375.5, filed Jun. 16, 2009; and GB Provisional 1111485.7, filed Jul. 5, 2011, each of which is hereby incorporated by reference in its entirety.

A cough is a protective reflexive action that helps clear the large breathing passages of the lungs from bodily secretions, irritants, foreign particles and microbes. A cough occurs when special cells along the air passages get irritated and trigger a chain of events, resulting in air being forced out of the lungs under high pressure. The cough reflex includes three phases: an inhalation, a forced exhalation against a closed glottis, and a violent release of air from the lungs following opening of the glottis, usually accompanied by a distinctive sound. Coughing can happen voluntarily as well as involuntarily.

Cough, although a common affliction, may have one or a combination of causes. For example, cough may be a result of a simple viral upper respiratory infection, of short duration, lasting but a few weeks (acute cough). However, cough can be persistent, lasting for several weeks, months, or even years (chronic cough). Chronic cough may be caused by continuous mucus drainage down the throat, asthma, gastroesophageal reflux, a variety of pulmonary disorders including chronic bronchitis and lung tumors, pollutants, choking, cardiovascular disorders, and even as a side effect of certain medications such as Angiotensin-Converting Enzyme (ACE) inhibitors. In some cases, coughing serves as a protective mechanism by preventing aspiration of foreign material into the lungs or, as with infectious processes, expulsion of unwanted mucus and pathogens from the airway. However, in many cases of chronic cough, the mechanism serves no useful purpose and may dramatically affect one's entire lifestyle causing sleeplessness, exhaustion, annoyance, self consciousness, and social limitation. Physical consequences may be hoarseness, incontinence of urine or stool, perspiration, and chest wall pain. Therefore, in those situations where cough serves no useful purpose, the benefit of a pharmaceutical composition and/or therapeutic compound to suppress cough, termed antitussives, are highly desirable.

The complications of coughing can be classified as either acute or chronic. Acute complications include cough syncope (fainting spells due to decreased blood flow to the brain when coughs are prolonged and forceful), insomnia, cough-induced vomiting, rupture of blebs causing spontaneous pneumothorax (although this still remains to be proven), subconjunctival hemorrhage or "red eye", coughing defecation and in women with a prolapsed uterus, cough urination. Chronic complications are common and include abdominal or pelvic hernias, fatigue fractures of lower ribs and costochondritis.

Even though cough medicines are a common an over-the-counter remedy for individuals seeking outpatient medical attention, their effectiveness as a treatment for a cough is doubtful. In 2006, the American College of Chest Physicians issued guidelines stating that "most over the counter cough medications are ineffective", and several research reports seem to confirm this conclusion. For example, the non-opiate antitussive drug Dextromethorphan is marketed as a cough therapy. However, its efficacy and suitability as a treatment for cough is questionable, since its apparent success as a clinical treatment was attributed to a placebo effect; Dextromethorphan itself had no efficacy in treating cough. (Ramsey et al., Br. J. Clin. Pharmacol.) Similarly, the decongestant pseudoephedrine has been to shown to have very limited efficacy in the citric acid induced cough model in guinea-pigs (Minamizawa et. al., J Pharmacol. Sci. 102 (1); 136-142, 2006) and most of the literature fails to demonstrate that pseudoephedrine has an antitussive effect. In fact, although a number of papers describe effects of pseudoephedrine on "cough and cold" (which has little meaning in the medical field), none describes or even examines direct antitussive effect. Lastly, a review article reports that presumptions about efficacy of the antihistamine diphenhydramine against cough in humans are not univocally substantiated in literature. (Bjornsdottir et al., Pharma. World Sci. 29(6): 577-583, 2007). In other words, there is no strong evidence that antihistamines have any efficacy in cough.

Thus, there is a still exists a need for the development of pharmaceutical compositions and/or therapeutic compounds having an antitussive activity.

SUMMARY

Aspects of the present specification disclose compositions comprising a plurality of therapeutic compounds having antitussive activity. Therapeutic compounds include, without limitation, a methylxanthine, a non-opiate antitussive agent, an opiate antitussive agent, a decongestant, an expectorant, a mucolytic agent, an anti-histamine, a non-steroidal anti-inflammatory drug (NSAID), a neuropathic pain agent, a terpene, an ACE inhibitor, an angiotensin II receptor antagonist or any combination thereof. The composition disclosed herein may reduce an unwanted side and/or reduce a symptom associated with a coughing condition. The composition disclosed herein may suppress a vagal nerve function associated with a cough, suppress a central nerve function associated with a cough, and/or suppress a peripheral nerve function associated with a cough.

Aspects of the present specification also disclose compositions comprising a methylxanthine and a plurality of additional therapeutic compounds having antitussive activity. Methylxanthines include, without limitation, Aminophylline, Caffeine, IBMX, Paraxanthine, Pentoxifylline, Theobromine, Theophylline, Xanthine, or any combination thereof. Additional therapeutic compounds include, without limitation, a non-opiate antitussive agent, an opiate antitussive agent, a decongestant, an expectorant, a mucolytic agent, an anti-histamine, a non-steroidal anti-inflammatory drug (NSAID), a neuropathic pain agent, a terpene, an ACE inhibitor, an angiotensin II receptor antagonist or any combination thereof. The composition disclosed herein may reduce an unwanted side and/or reduce a symptom associated with a coughing condition. The composition disclosed herein may suppress a vagal nerve function associated with a cough, suppress a central nerve function associated with a cough, and/or suppress a peripheral nerve function associated with a cough.

Aspects of the present specification also disclose methods of treating a coughing condition in an individual. The disclosed methods comprising the step of administering a pharmaceutical composition disclosed herein to an individual, wherein administration reduces a symptom associated with the coughing condition. The coughing condition may be an acute coughing condition, a subacute coughing condition, or a chronic coughing condition. The coughing condition may be a non-productive coughing condition or a productive coughing condition. The coughing condition may be a cough associated with a disease or disorder. Administration of a pharmaceutical composition may also reduce an unwanted side in the individual.

Aspects of the present specification disclose uses of the disclosed compositions and/or therapeutic compounds in the manufacture of a medicament for the treatment of a coughing condition.

Aspects of the present specification disclose uses of the disclosed compositions and/or therapeutic compounds in the treatment of a coughing condition.

DESCRIPTION

The present specification discloses combinations of various therapeutic compounds that when combined produce synergistic effects in reducing a symptom associated with a coughing condition. Consequently, a considerably reduced dose of both therapeutic compounds can be given for an equivalent effect for each individual therapeutic compound, thereby reducing side-effects and drug burden.

In addition, the present specification discloses that administration of the disclosed combinations of various therapeutic compounds by inhalation, a therapeutically effect is observed at one-third the dose administered orally. Via the inhaled route, therapeutic compounds disclosed herein are surprisingly potent and do not follow the oral PK/PD relationship, revealing that the disclosed combinations of various therapeutic compounds have a substantially local effect in the lung. Consequently, via the inhaled route, less drug is given for an equivalent oral effect, so reducing side-effects and drug burden.

Aspects of the present specification disclose, in part, a pharmaceutical composition. As used herein, the term "pharmaceutical composition" is synonymous with "pharmaceutically acceptable composition" and refers to a therapeutically effective concentration of an active ingredient, such as, e.g., any of the therapeutic compounds disclosed herein. As used herein, the term "pharmaceutically acceptable" refers to any molecular entity or composition that does not produce an adverse, allergic or other untoward or unwanted reaction when administered to an individual. A pharmaceutical composition disclosed herein is useful for medical and veterinary applications. A pharmaceutical composition may be administered to an individual alone, or in combination with other supplementary active ingredients, agents, drugs or hormones.

A pharmaceutical composition disclosed herein may comprise one or more therapeutic compounds disclosed herein. In one embodiment, pharmaceutical composition disclosed herein may comprise only a single a therapeutic compound having antitussive activity. In another embodiment, pharmaceutical composition disclosed herein may comprise a plurality of therapeutic compounds having antitussive activity. In aspects of this embodiment, a pharmaceutical composition disclosed herein comprises at least one therapeutic compound having antitussive activity, at least two therapeutic compounds having antitussive activity, at least three therapeutic compounds having antitussive activity, or at least four therapeutic compounds having antitussive activity. In other aspects of this embodiment, a pharmaceutical composition disclosed herein comprises at most two therapeutic compounds having antitussive activity, at most three therapeutic compounds having antitussive activity, or at most four therapeutic compounds having antitussive activity. In yet other aspects of this embodiment, a pharmaceutical composition disclosed herein comprises one to three therapeutic compounds having antitussive activity, two to four therapeutic compounds having antitussive activity, two to five therapeutic compounds having antitussive activity, three to five therapeutic compounds having antitussive activity, or two to three therapeutic compounds having antitussive activity. In aspects of this embodiment, a therapeutic compound having antitussive activity includes, without limitation, a methylxanthine, a non-opiate antitussive agent, an opiate antitussive agent, a decongestant, an expectorant, a mucolytic agent, an anti-histamine, a non-steroidal anti-inflammatory drug (NSAID), a neuropathic pain agent, a terpene, an ACE inhibitor, and/or an angiotensin II receptor antagonist.

In another embodiment, a pharmaceutical composition disclosed herein comprises a methylxanthine and a single additional therapeutic compound having antitussive activity. In another embodiment, a pharmaceutical composition disclosed herein comprises a methylxanthine and a plurality of additional therapeutic compound having antitussive activity. In aspects of this embodiment, a pharmaceutical composition disclosed herein comprises a methylxanthine and at least one additional therapeutic compound having antitussive activity at least two additional therapeutic compounds having antitussive activity, at least three additional therapeutic compounds having antitussive activity, at least four additional therapeutic compounds having antitussive activity. In other aspects of this embodiment, a pharmaceutical composition disclosed herein comprises a methylxanthine and at most one additional therapeutic compound having antitussive activity, at most two additional therapeutic compounds having antitussive activity, at most three additional therapeutic compounds having antitussive activity, at most four additional therapeutic compounds having antitussive activity. In yet other aspects of this embodiment, a pharmaceutical composition disclosed herein comprises a methylxanthine and one to three additional therapeutic compounds having antitussive activity, two to four additional therapeutic compound having antitussive activity, two to three additional therapeutic compounds having antitussive activity, two to five additional therapeutic compound having antitussive activity, or three to five additional therapeutic compound having antitussive activity. In aspects of this embodiment, an additional therapeutic compound having antitussive activity includes, without limitation, a non-opiate antitussive agent, an opiate antitussive agent, a decongestant, an expectorant, a mucolytic agent, an anti-histamine, a non-steroidal anti-inflammatory drug (NSAID), a neuropathic pain agent, a terpene, an ACE inhibitor, and/or an angiotensin II receptor antagonist.

In another embodiment, a pharmaceutical composition disclosed herein comprises a methylxanthine and a plurality of therapeutic compounds having antitussive activity disclosed herein, wherein the plurality of therapeutic compounds does not include a non-opiate antitussive agent disclosed herein. In an aspect of this embodiment, a pharmaceutical composition disclosed herein comprises a methylxanthine and a plurality of therapeutic compounds having antitussive activity, wherein the plurality of therapeutic compounds does not include Dextromethorphan.

In another embodiment, a pharmaceutical composition disclosed herein comprises a methylxanthine and a plurality of therapeutic compounds having antitussive activity disclosed herein, wherein the plurality of therapeutic compounds does not include an anti-histamine disclosed herein. In an aspect of this embodiment, a pharmaceutical composition disclosed herein comprises a methylxanthine and a plurality of therapeutic compounds having antitussive activity, wherein the plurality of therapeutic compounds does not include Azatadine, Bromodiphenhydramine, Brompheniramine, Carbinoxamine, Cetirizine, Chlorpheniramine, Clemestine, Dexchlorpheniramine, Dexbrompheniramine, Diphenhydramine, Doxylamine, Pyrilamine, Tripelennamine, or Tripolidine.

A pharmaceutical composition disclosed herein may reduce an unwanted side effect elicited by administration of one or more of the therapeutic compounds contained in the pharmaceutical composition. Examples of unwanted side effects, include, without limitation, sedation, cognitive fogging, dizziness, drowsiness, postural hypertension, coordination problems, weakness, tremors, respiratory depression, psychotropic effects, sleep disturbances, unwanted waitfulness, CNS stimulation, weight gain, appetite change, change in sexual function, constipation, dry mouth, gut erosion, gastric ulcerations, renal inflammation, cardiovascular hypertension, cardiovascular stimulation, hyperchlimina, not going into public, chest pain, and/or stress incontinence.

In aspects of this embodiment, an unwanted side-effect associated with a non-opiate antitussive agent, includes, without limitation, sedation, psychotropic effect, hallucination, or any combination thereof. In other aspects of this embodiment, an unwanted side-effect associated with an opiate antitussive agent includes, without limitation, sedation, constipation, respiratory depression, or any combination thereof. In yet other aspects of this embodiment, an unwanted side-effect associated with a decongestant includes, without limitation, unwanted waitfulness, CNS stimulation, cardiovascular stimulation, tachycardia, or any combination thereof. In still other aspects of this embodiment, an unwanted side-effect associated with an antihistamine includes, without limitation, sedation, dry mouth, a sensory-based side effect, an anti-muscarinic side effect, or any combination thereof.

In other aspects of this embodiment, an unwanted side-effect associated with a NSAID, includes, without limitation, gut erosion, gastric ulcerations, renal inflammation, cardiovascular hypertension, or any combination thereof. In yet other aspects of this embodiment, an unwanted side-effect associated with a neuropathic pain agent, includes, without limitation, cognitive fogging, dizziness, drowsiness, coordination problems, weakness, tremors, weight gain, appetite change, change in sexual function, sleep disturbance, or any combination thereof. In still other aspects of this embodiment, an unwanted side-effect associated with an ACE inhibitor, includes, without limitation, coughing, hyperchlimina, postural hypertension, dizziness, headache, drowsiness, weakness, or any combination thereof. In further aspects of this embodiment, an unwanted side-effect associated with an angiotension 2 receptor antagonist, includes, without limitation, coughing, hyperchlimina, postural hypertension, dizziness, headache, drowsiness, weakness, or any combination thereof.

Aspects of the present specification disclose, in part, a therapeutic compound. A therapeutic compound is a compound that provides pharmacological activity or other direct effect in the diagnosis, cure, mitigation, treatment, or prevention of disease, or to affect the structure or any function of the body of man or animals. Any suitable form of a therapeutic compound may be chosen. A therapeutic compound disclosed herein may be used in the form of a pharmaceutically acceptable salt, solvate, or solvate of a salt, e.g. the hydrochloride. Additionally, therapeutic compound disclosed herein may be provided as racemates, or as individual enantiomers, including the R- or S-enantiomer. Thus, the therapeutic compound disclosed herein may comprise a R-enantiomer only, a S-enantiomer only, or a combination of both a R-enantiomer and a S-enantiomer of a therapeutic compound. A therapeutic compound disclosed herein may also be provided as prodrug or active metabolite.

A therapeutic compound disclosed herein may have antitussive activity. As used herein, the term "antitussive activity" refers to the ability of a therapeutic compound to reduce a symptom associated with a coughing condition, including, without limitation, the frequency of a cough, the severity of a cough, the volume or noise level of a cough, hoarseness, sore throat, breathing difficulty, respiratory congestion, wheezing, respiratory constriction, respiratory inflammation, muscle spasms associated with a cough, phlegm production, fainting, insomnia, vomiting, subconjunctival hemorrhage (red eye), cough defecation, cough urination, abdominal hernia, pelvic hernia, costochondritis, and lower rib fractures.

In one embodiment, a therapeutic compound disclosed herein having antitussive activity reduces a symptom associated with a coughing condition. In aspects of this embodiment, a therapeutic compound having antitussive activity reduces a symptom associated with a coughing condition by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound having antitussive activity reduces a symptom associated with a coughing condition by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In another embodiment, a therapeutic compound disclosed herein having antitussive activity reduces the frequency of a cough or the number of coughs that incur over a given time period. In aspects of this embodiment, a therapeutic compound having antitussive activity the frequency of a cough by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound having antitussive activity reduces the frequency of a cough by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In another embodiment, a therapeutic compound disclosed herein having antitussive activity reduces the severity of a cough. In aspects of this embodiment, a therapeutic compound having antitussive activity reduces the severity of a cough by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound having antitussive activity reduces the severity of a cough by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In another embodiment, a therapeutic compound disclosed herein having antitussive activity reduces muscle spasms associated with a cough. In aspects of this embodiment, a therapeutic compound having antitussive activity reduces muscle spasms associated with a cough by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound having antitussive activity reduces muscle spasms associated with a cough by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In another embodiment, a therapeutic compound disclosed herein having antitussive activity reduces the volume or noise level of a cough. In aspects of this embodiment, a therapeutic compound having antitussive activity reduces the volume or noise level of a cough by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound having antitussive activity reduces the volume or noise level of a cough by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

The coughing mechanism is a reflex arc that is initiated by stimulation of sensory nerve fibers belonging to branches of the vagal nerve distributed throughout the respiratory tract with greatest concentration in the upper airways. There fibers respond to chemical and/or mechanical stimuli. After stimulation, impulses travel away along nerves (afferent limb), to intermediate nerve terminal ganglions, where connecting nerves intersect to further transmit impulses to the cough center in the medulla. In the brain, all nerve impulses are integrated, and a coordinated set of nerve impulses are generated to nerves (efferent limb) leading to the expiratory muscles that contract to produce an effective cough. A pharmaceutical composition or a therapeutic compound disclosed herein have an antitussive effect that may work at one or at a combination of sites along the reflex arc.

In one embodiment, a therapeutic compound disclosed herein having antitussive activity suppresses a vagal nerve function associated with a cough. In aspects of this embodiment, a therapeutic compound having antitussive activity suppresses vagal nerve function associated with a cough by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound having antitussive activity suppresses vagal nerve function associated with a cough by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In another embodiment, a therapeutic compound disclosed herein having antitussive activity suppresses a central nerve function associated with a cough. In aspects of this embodiment, a therapeutic compound having antitussive activity suppresses central nerve function associated with a cough by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound having antitussive activity suppresses central nerve function associated with a cough by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In another embodiment, a therapeutic compound disclosed herein having antitussive activity suppresses a peripheral nerve function associated with a cough. In aspects of this embodiment, a therapeutic compound having antitussive activity suppresses peripheral nerve function associated with a cough by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound having antitussive activity suppresses peripheral nerve function associated with a cough by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

A therapeutic compound disclosed herein may be a cocoa. In aspects of this embodiment, the cocoa may be a cocoa powder, a cocoa liquid, or any other suitable form of cocoa. In aspects of this embodiment, a pharmaceutical composition comprises cocoa is in an amount of, e.g., about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 18%, or about 20% of the total weight or volume of the pharmaceutical composition. In other aspects of this embodiment, a pharmaceutical composition comprises cocoa is in an amount of, e.g., at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 18%, or at least 20% of the total weight or volume of the pharmaceutical composition. In yet other aspects of this embodiment, a pharmaceutical composition comprises cocoa is in an amount of, e.g., at most 1%, at most 2%, at most 3%, at most 4%, at most 5%, at most 6%, at most 7%, at most 8%, at most 9%, at most 10%, at most 11%, at most 12%, at most 13%, at most 14%, at most 15%, at most 16%, at most 17%, at most 18%, at most 18%, or at most 20% of the total weight or volume of the pharmaceutical composition. In still other aspects of this embodiment, a pharmaceutical composition comprises cocoa is in an amount of, e.g., about 1% to about 3%, about 1% to about 5%, about 1% to about 7%, about 1% to about 10%, about 1% to about 12%, about 1% to about 15%, about 1% to about 18%, about 1% to about 20%, about 2% to about 3%, about 2% to about 5%, about 2% to about 7%, about 2% to about 10%, about 2% to about 12%, about 2% to about 15%, about 2% to about 18%, about 2% to about 20%, about 3% to about 5%, about 3% to about 7%, about 3% to about 10%, about 3% to about 12%, about 3% to about 15%, about 3% to about 18%, about 3% to about 20%, about 5% to about 7%, about 5% to about 10%, about 5% to about 12%, about 5% to about 15%, about 5% to about 18%, about 5% to about 20%, about 7% to about 10%, about 7% to about 12%, about 7% to about 15%, about 7% to about 18%, about 7% to about 20%, about 8% to about 10%, about 8% to about 12%, about 8% to about 15%, about 8% to about 18%, about 8% to about 20%, about 10% to about 12%, about 10% to about 15%, about 10% to about 18%, about 10% to about 20%, bout 12% to about 15%, about 12% to about 18%, about 12% to about 20%, about 15% to about 18%, about 15% to about 20%, or about 18% to about 20%.

A therapeutic compound disclosed herein may be a methylxanthine. As used herein, the term "methylxanthine" refers to a class of therapeutic compounds composed of various purines having two oxygen atoms attached to the six-member ring of carbon and nitrogen atoms that act as a smooth muscle relaxant, vasodilator, and/or diuretic. Methylxanthines act as bronchodilators by relaxing bronchial smooth muscles, thereby dilating inflamed or otherwise constricted respiratory tract airways. Methylxanthines are 1) competitive nonselective phosphodiesterase inhibitor which raise intracellular cAMP, activate PKA, inhibit TNF-α, and inhibit leukotriene synthesis, thereby reducing inflammation and innate immunity; and 2) nonselective adenosine receptor antagonist, blocking A1, A2, and A3 receptors, thereby inhibiting the bronchoconstriction and sleepiness-inducing effects of adenosine. Methylxanthines naturally occur in as many as sixty different plant species including the coffee plant, cacao plant, tea plant, and the kola (or cola) plant. Examples of suitable methylxanthines include, without limitation, Aminophylline, Caffeine (1,3,7-trimethyl-1H-purine-2,6(3H,7H)-dione), IBMX, Paraxanthine, Pentoxifylline, Theobromine (3,7-dihydro-3,7-dimethyl-1H-purine-2,6-dione), Theophylline (1,3-dimethyl-7H-purine-2,6-dione) and Xanthine (3,7-dihydro-purine-2,6-dione).

A methylxanthine may be in an amount suitable for its intended use. In aspects of this embodiment, a pharmaceutical composition comprises methylxanthine in an amount of, e.g., about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 14 mg/mL, about 15 mg/mL, about 16 mg/mL, about 17 mg/mL, about 18 mg/mL, about 19 mg/mL, about 20 mg/mL, about 21 mg/mL, about 22 mg/mL, about 23 mg/mL, about 24 mg/mL, about 25 mg/mL, about 26 mg/mL, about 27 mg/mL, about 28 mg/mL, about 29 mg/mL, or about 30 mg/mL In other aspects of this embodiment, a pharmaceutical composition comprises methylxanthine in an amount of, e.g., about 10 mg/mL, about 20 mg/mL, about 30 mg/mL, about 40 mg/mL, about 50 mg/mL, about 60 mg/mL, about 70 mg/mL, about 80 mg/mL, about 90 mg/mL, about 100 mg/mL, about 125 mg/mL, about 150 mg/mL, about 175 mg/mL, about 200 mg/mL, about 225 mg/mL, about 250 mg/mL, about 275 mg/mL, about 300 mg/mL, about 325 mg/mL, about 350 mg/mL, about 375 mg/mL, about 400 mg/mL, about 425 mg/mL, about 450 mg/mL, about 475 mg/mL, about 500 mg/mL, about 525 mg/mL, about 550 mg/mL, about 575 mg/mL, about 600 mg/mL, about 625 mg/mL, about 650 mg/mL, about 675 mg/mL, about 700 mg/mL, about 725 mg/mL, about 750 mg/mL, about 775 mg/mL, about 800 mg/mL, about 825 mg/mL, about 850 mg/mL, about 875 mg/mL, about 900 mg/mL, about 925 mg/mL, about 950 mg/mL, about 975 mg/mL, or about 1000 mg/mL.

In other aspects of this embodiment, a pharmaceutical composition comprises methylxanthine in an amount of, e.g., at least 0.1 mg/mL, at least 0.2 mg/mL, at least 0.3 mg/mL, at least 0.4 mg/mL, at least 0.5 mg/mL, at least 0.6 mg/mL, at least 0.7 mg/mL, at least 0.8 mg/mL, at least 0.9 mg/mL, at least 1 mg/mL, at least 2 mg/mL, at least 3 mg/mL, at least 4 mg/mL, at least 5 mg/mL, at least 6 mg/mL, at least 7 mg/mL, at least 8 mg/mL, at least 9 mg/mL, at least 10 mg/mL, at least 11 mg/mL, at least 12 mg/mL, at least 13 mg/mL, at least 14 mg/mL, at least 15 mg/mL, at least 16 mg/mL, at least 17 mg/mL, at least 18 mg/mL, at least 19 mg/mL, at least 20 mg/mL, at least 21 mg/mL, at least 22 mg/mL, at least 23 mg/mL, at least 24 mg/mL, at least 25 mg/mL, at least 26 mg/mL, at least 27 mg/mL, at least 28 mg/mL, at least 29 mg/mL, or at least 30 mg/mL In aspects of this embodiment, a pharmaceutical composition comprises methylxanthine in an amount of, e.g., at least 10 mg/mL, at least 20 mg/mL, at least 30 mg/mL, at least 40 mg/mL, at least 50 mg/mL, at least 60 mg/mL, at least 70 mg/mL, at least 80 mg/mL, at least 90 mg/mL, at least 100 mg/mL, at least 125 mg/mL, at least 150 mg/mL, at least 175 mg/mL, at least 200 mg/mL, at least 225 mg/mL, at least 250 mg/mL, at least 275 mg/mL, at least 300 mg/mL, at least 325 mg/mL, at least 350 mg/mL, at least 375 mg/mL, at least 400 mg/mL, at least 425 mg/mL, at least 450 mg/mL, at least 475 mg/mL, at least 500 mg/mL, at least 525 mg/mL, at least 550 mg/mL, at least 575 mg/mL, at least 600 mg/mL, at least 625 mg/mL, at least 650 mg/mL, at least 675 mg/mL, at least 700 mg/mL, at least 725 mg/mL, at least 750 mg/mL, at least 775 mg/mL, at least 800 mg/mL, at least 825 mg/mL, at least 850 mg/mL, at least 875 mg/mL, at least 900 mg/mL, at least 925 mg/mL, at least 950 mg/mL, at least 975 mg/mL, or at least 1000 mg/mL.

In other aspects of this embodiment, a pharmaceutical composition comprises methylxanthine in an amount of, e.g., at most 0.1 mg/mL, at most 0.2 mg/mL, at most 0.3 mg/mL, at most 0.4 mg/mL, at most 0.5 mg/mL, at most 0.6 mg/mL, at most 0.7 mg/mL, at most 0.8 mg/mL, at most 0.9 mg/mL, at most 1 mg/mL, at most 2 mg/mL, at most 3 mg/mL, at most 4 mg/mL, at most 5 mg/mL, at most 6 mg/mL, at most 7 mg/mL, at most 8 mg/mL, at most 9 mg/mL, at most 10 mg/mL, at most 11 mg/mL, at most 12 mg/mL, at most 13 mg/mL, at most 14 mg/mL, at most 15 mg/mL, at most 16 mg/mL, at most 17 mg/mL, at most 18 mg/mL, at most 19 mg/mL, at most 20 mg/mL, at most 21 mg/mL, at most 22 mg/mL, at most 23 mg/mL, at most 24 mg/mL, at most 25 mg/mL, at most 26 mg/mL, at most 27 mg/mL, at most 28 mg/mL, at most 29 mg/mL, or at most 30 mg/mL In yet other aspects of this embodiment, a pharmaceutical composition comprises methylxanthine in an amount of, e.g., at most 10 mg/mL, at most 20 mg/mL, at most 30 mg/mL, at most 40 mg/mL, at most 50 mg/mL, at most 60 mg/mL, at most 70 mg/mL, at most 80 mg/mL, at most 90 mg/mL, at most 100 mg/mL, at most 125 mg/mL, at most 150 mg/mL, at most 175 mg/mL, at most 200 mg/mL, at most 225 mg/mL, at most 250 mg/mL, at most 275 mg/mL, at most 300 mg/mL, at most 325 mg/mL, at most 350 mg/mL, at most 375 mg/mL, at most 400 mg/mL, at most 425 mg/mL, at most 450 mg/mL, at most 475 mg/mL, at most 500 mg/mL, at most 525 mg/mL, at most 550 mg/mL, at most 575 mg/mL, at most 600 mg/mL, at most 625 mg/mL, at most 650 mg/mL, at most 675 mg/mL, at most 700 mg/mL, at most 725 mg/mL, at most 750 mg/mL, at most 775 mg/mL, at most 800 mg/mL, at most 825 mg/mL, at most 850 mg/mL, at most 875 mg/mL, at most 900 mg/mL, at most 925 mg/mL, at most 950 mg/mL, at most 975 mg/mL, or at most 1000 mg/mL.

In other aspects of this embodiment, a pharmaceutical composition comprises methylxanthine in an amount of, e.g., about 0.1 mg/mL to about 1 mg/mL, about 0.1 mg/mL to about 2 mg/mL, about 0.1 mg/mL to about 3 mg/mL, about 0.1 mg/mL to about 4 mg/mL, about 0.1 mg/mL to about 5 mg/mL, about 0.1 mg/mL to about 6 mg/mL, about 0.1 mg/mL to about 7 mg/mL, about 0.1 mg/mL to about 8 mg/mL, about 0.1 mg/mL to about 9 mg/mL, about 0.1 mg/mL to about 10 mg/mL, about 0.5 mg/mL to about 1 mg/mL, about 0.5 mg/mL to about 2 mg/mL, about 0.5 mg/mL to about 3 mg/mL, about 0.5 mg/mL to about 4 mg/mL, about 0.5 mg/mL to about 5 mg/mL, about 0.5 mg/mL to about 6 mg/mL, about 0.5 mg/mL to about 7 mg/mL, about 0.5 mg/mL to about 8 mg/mL, about 0.5 mg/mL to about 9 mg/mL, about 0.5 mg/mL to about 10 mg/mL, about 1 mg/mL to about 5 mg/mL, about 1 mg/mL to about 10 mg/mL, about 1 mg/mL to about 15 mg/mL, about 1 mg/mL to about 20 mg/mL, about 1 mg/mL to about 25 mg/mL, about 1 mg/mL to about 30 mg/mL, about 1 mg/mL to about 35 mg/mL, about 1 mg/mL to about 40 mg/mL, about 1 mg/mL to about 45 mg/mL, about 1 mg/mL to about 50 mg/mL, about 5 mg/mL to about 10 mg/mL, about 5 mg/mL to about 15 mg/mL, about 5 mg/mL to about 20 mg/mL, about 5 mg/mL to about 25 mg/mL, about 5 mg/mL to about 30 mg/mL, about 5 mg/mL to about 35 mg/mL, about 5 mg/mL to about 40 mg/mL, about 5 mg/mL to about 45 mg/mL, about 5 mg/mL to about 50 mg/mL, about 10 mg/mL to about 20 mg/mL, about 10 mg/mL to about 30 mg/mL, about 10 mg/mL to about 40 mg/mL, about 10 mg/mL to about 50 mg/mL, about 10 mg/mL to about 60 mg/mL, about 10 mg/mL to about 70 mg/mL, about 10 mg/mL to about 80 mg/mL, about 10 mg/mL to about 90 mg/mL, about 10 mg/mL to about 100 mg/mL, about 25 mg/mL to about 50 mg/mL, about 25 mg/mL to about 75 mg/mL, about 25 mg/mL to about 100 mg/mL, about 25 mg/mL to about 125 mg/mL, about 25 mg/mL to about 150 mg/mL, about 25 mg/mL to about 175 mg/mL, about 25 mg/mL to about 200 mg/mL, about 25 mg/mL to about 225 mg/mL, about 25 mg/mL to about 250 mg/mL, about 50 mg/mL to about 75 mg/mL, about 50 mg/mL to about 100 mg/mL, about 50 mg/mL to about 125 mg/mL, about 50 mg/mL to about 150 mg/mL, about 50 mg/mL to about 175 mg/mL, about 50 mg/mL to about 200 mg/mL, about 50 mg/mL to about 225 mg/mL, about 50 mg/mL to about 250 mg/mL, about 50 mg/mL to about 275 mg/mL, about 50 mg/mL to about 300 mg/mL, about 50 mg/mL to about 325 mg/mL, about 50 mg/mL to about 350 mg/mL, about 50 mg/mL to about 375 mg/mL, about 50 mg/mL to about 400 mg/mL, about 50 mg/mL to about 425 mg/mL, about 50 mg/mL to about 450 mg/mL, about 50 mg/mL to about 475 mg/mL, about 50 mg/mL to about 500 mg/mL, about 100 mg/mL to about 150 mg/mL, about 100 mg/mL to about 200 mg/mL, about 100 mg/mL to about 250 mg/mL, about 100 mg/mL to about 300 mg/mL, about 100 mg/mL to about 350 mg/mL, about 100 mg/mL to about 400 mg/mL, about 100 mg/mL to about 450 mg/mL, about 100 mg/mL to about 500 mg/mL, about 200 mg/mL to about 300 mg/mL, about 200 mg/mL to about 400 mg/mL, about 200 mg/mL to about 500 mg/mL, about 200 mg/mL to about 600 mg/mL, about 200 mg/mL to about 700 mg/mL, about 200 mg/mL to about 800 mg/mL, about 200 mg/mL to about 900 mg/mL, or about 200 mg/mL to about 1000 mg/mL.

A theobromine may be in an amount suitable for its intended use. In aspects of this embodiment, a pharmaceutical composition comprises a theobromine in an amount of, e.g., about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 14 mg/mL, about 15 mg/mL, about 16 mg/mL, about 17 mg/mL, about 18 mg/mL, about 19 mg/mL, about 20 mg/mL, about 21 mg/mL, about 22 mg/mL, about 23 mg/mL, about 24 mg/mL, about 25 mg/mL, about 26 mg/mL, about 27 mg/mL, about 28 mg/mL, about 29 mg/mL, or about 30 mg/mL In other aspects of this embodiment, a pharmaceutical composition comprises a theobromine in an amount of, e.g., about 10 mg/mL, about 20 mg/mL, about 30 mg/mL, about 40 mg/mL, about 50 mg/mL, about 60 mg/mL, about 70 mg/mL, about 80 mg/mL, about 90 mg/mL, about 100 mg/mL, about 125 mg/mL, about 150 mg/mL, about 175 mg/mL, about 200 mg/mL, about 225 mg/mL, about 250 mg/mL, about 275 mg/mL, about 300 mg/mL, about 325 mg/mL, about 350 mg/mL, about 375 mg/mL, about 400 mg/mL, about 425 mg/mL, about 450 mg/mL, about 475 mg/mL, about 500 mg/mL, about 525 mg/mL, about 550 mg/mL, about 575 mg/mL, about 600 mg/mL, about 625 mg/mL, about 650 mg/mL, about 675 mg/mL, about 700 mg/mL, about 725 mg/mL, about 750 mg/mL, about 775 mg/mL, about 800 mg/mL, about 825 mg/mL, about 850 mg/mL, about 875 mg/mL, about 900 mg/mL, about 925 mg/mL, about 950 mg/mL, about 975 mg/mL, or about 1000 mg/mL.

In other aspects of this embodiment, a pharmaceutical composition comprises a theobromine in an amount of, e.g., at least 0.1 mg/mL, at least 0.2 mg/mL, at least 0.3 mg/mL, at least 0.4 mg/mL, at least 0.5 mg/mL, at least 0.6 mg/mL, at least 0.7 mg/mL, at least 0.8 mg/mL, at least 0.9 mg/mL, at least 1 mg/mL, at least 2 mg/mL, at least 3 mg/mL, at least 4 mg/mL, at least 5 mg/mL, at least 6 mg/mL, at least 7 mg/mL, at least 8 mg/mL, at least 9 mg/mL, at least 10 mg/mL, at least 11 mg/mL, at least 12 mg/mL, at least 13 mg/mL, at least 14 mg/mL, at least 15 mg/mL, at least 16 mg/mL, at least 17 mg/mL, at least 18 mg/mL, at least 19 mg/mL, at least 20 mg/mL, at least 21 mg/mL, at least 22 mg/mL, at least 23 mg/mL, at least 24 mg/mL, at least 25 mg/mL, at least 26 mg/mL, at least 27 mg/mL, at least 28 mg/mL, at least 29 mg/mL, or at least 30 mg/mL In aspects of this embodiment, a pharmaceutical composition comprises theobromine in an amount of, e.g., at least 10 mg/mL, at least 20 mg/mL, at least 30 mg/mL, at least 40 mg/mL, at least 50 mg/mL, at least 60 mg/mL, at least 70 mg/mL, at least 80 mg/mL, at least 90 mg/mL, at least 100 mg/mL, at least 125 mg/mL, at least 150 mg/mL, at least 175 mg/mL, at least 200 mg/mL, at least 225 mg/mL, at least 250 mg/mL, at least 275 mg/mL, at least 300 mg/mL, at least 325 mg/mL, at least 350 mg/mL, at least 375 mg/mL, at least 400 mg/mL, at least 425 mg/mL, at least 450 mg/mL, at least 475 mg/mL, at least 500 mg/mL, at least 525 mg/mL, at least 550 mg/mL, at least 575 mg/mL, at least 600 mg/mL, at least 625 mg/mL, at least 650 mg/mL, at least 675 mg/mL, at least 700 mg/mL, at least 725 mg/mL, at least 750 mg/mL, at least 775 mg/mL, at least 800 mg/mL, at least 825 mg/mL, at least 850 mg/mL, at least 875 mg/mL, at least 900 mg/mL, at least 925 mg/mL, at least 950 mg/mL, at least 975 mg/mL, or at least 1000 mg/mL.

In other aspects of this embodiment, a pharmaceutical composition comprises a theobromine in an amount of, e.g., at most 0.1 mg/mL, at most 0.2 mg/mL, at most 0.3 mg/mL, at most 0.4 mg/mL, at most 0.5 mg/mL, at most 0.6 mg/mL, at most 0.7 mg/mL, at most 0.8 mg/mL, at most 0.9 mg/mL, at most 1 mg/mL, at most 2 mg/mL, at most 3 mg/mL, at most 4 mg/mL, at most 5 mg/mL, at most 6 mg/mL, at most 7 mg/mL, at most 8 mg/mL, at most 9 mg/mL, at most 10 mg/mL, at most 11 mg/mL, at most 12 mg/mL, at most 13 mg/mL, at most 14 mg/mL, at most 15 mg/mL, at most 16 mg/mL, at most 17 mg/mL, at most 18 mg/mL, at most 19 mg/mL, at most 20 mg/mL, at most 21 mg/mL, at most 22 mg/mL, at most 23 mg/mL, at most 24 mg/mL, at most 25 mg/mL, at most 26 mg/mL, at most 27 mg/mL, at most 28 mg/mL, at most 29 mg/mL, or at most 30 mg/mL In yet other aspects of this embodiment, a theobromine is in an amount of, e.g., at most 10 mg/mL, at most 20 mg/mL, at most 30 mg/mL, at most 40 mg/mL, at most 50 mg/mL, at most 60 mg/mL, at most 70 mg/mL, at most 80 mg/mL, at most 90 mg/mL, at most 100 mg/mL, at most 125 mg/mL, at most 150 mg/mL, at most 175 mg/mL, at most 200 mg/mL, at most 225 mg/mL, at most 250 mg/mL, at most 275 mg/mL, at most 300 mg/mL, at most 325 mg/mL, at most 350 mg/mL, at most 375 mg/mL, at most 400 mg/mL, at most 425 mg/mL, at most 450 mg/mL, at most 475 mg/mL, at most 500 mg/mL, at most 525 mg/mL, at most 550 mg/mL, at most 575 mg/mL, at most 600 mg/mL, at most 625 mg/mL, at most 650 mg/mL, at most 675 mg/mL, at most 700 mg/mL, at most 725 mg/mL, at most 750 mg/mL, at most 775 mg/mL, at most 800 mg/mL, at most 825 mg/mL, at most 850 mg/mL, at most 875 mg/mL, at most 900 mg/mL, at most 925 mg/mL, at most 950 mg/mL, at most 975 mg/mL, or at most 1000 mg/mL.

In other aspects of this embodiment, a pharmaceutical composition comprises a theobromine in an amount of, e.g., about 0.1 mg/mL to about 1 mg/mL, about 0.1 mg/mL to about 2 mg/mL, about 0.1 mg/mL to about 3 mg/mL, about 0.1 mg/mL to about 4 mg/mL, about 0.1 mg/mL to about 5 mg/mL, about 0.1 mg/mL to about 6 mg/mL, about 0.1 mg/mL to about 7 mg/mL, about 0.1 mg/mL to about 8 mg/mL, about 0.1 mg/mL to about 9 mg/mL, about 0.1 mg/mL to about 10 mg/mL, about 0.5 mg/mL to about 1 mg/mL, about 0.5 mg/mL to about 2 mg/mL, about 0.5 mg/mL to about 3 mg/mL, about 0.5 mg/mL to about 4 mg/mL, about 0.5 mg/mL to about 5 mg/mL, about 0.5 mg/mL to about 6 mg/mL, about 0.5 mg/mL to about 7 mg/mL, about 0.5 mg/mL to about 8 mg/mL, about 0.5 mg/mL to about 9 mg/mL, about 0.5 mg/mL to about 10 mg/mL, about 1 mg/mL to about 2 mg/mL, about 1 mg/mL to about 3 mg/mL, about 1 mg/mL to about 4 mg/mL, about 1 mg/mL to about 5 mg/mL, about 1 mg/mL to about 6 mg/mL, about 1 mg/mL to about 7 mg/mL, about 1 mg/mL to about 8 mg/mL, about 1 mg/mL to about 9 mg/mL, about 1 mg/mL to about 10 mg/mL, about 1 mg/mL to about 15 mg/mL, about 1 mg/mL to about 20 mg/mL, about 1 mg/mL to about 25 mg/mL, about 1 mg/mL to about 30 mg/mL, about 1 mg/mL to about 35 mg/mL, about 1 mg/mL to about 40 mg/mL, about 1 mg/mL to about 45 mg/mL, about 1 mg/mL to about 50 mg/mL, about 5 mg/mL to about 10 mg/mL, about 5 mg/mL to about 15 mg/mL, about 5 mg/mL to about 20 mg/mL, about 5 mg/mL to about 25 mg/mL, about 5 mg/mL to about 30 mg/mL, about 5 mg/mL to about 35 mg/mL, about 5 mg/mL to about 40 mg/mL, about 5 mg/mL to about 45 mg/mL, about 5 mg/mL to about 50 mg/mL, about 10 mg/mL to about 20 mg/mL, about 10 mg/mL to about 30 mg/mL, about 10 mg/mL to about 40 mg/mL, about 10 mg/mL to about 50 mg/mL, about 10 mg/mL to about 60 mg/mL, about 10 mg/mL to about 70 mg/mL, about 10 mg/mL to about 80 mg/mL, about 10 mg/mL to about 90 mg/mL, about 10 mg/mL to about 100 mg/mL, about 25 mg/mL to about 50 mg/mL, about 25 mg/mL to about 75 mg/mL, about 25 mg/mL to about 100 mg/mL, about 25 mg/mL to about 125 mg/mL, about 25 mg/mL to about 150 mg/mL, about 25 mg/mL to about 175 mg/mL, about 25 mg/mL to about 200 mg/mL, about 25 mg/mL to about 225 mg/mL, about 25 mg/mL to about 250 mg/mL, about 50 mg/mL to about 75 mg/mL, about 50 mg/mL to about 100 mg/mL, about 50 mg/mL to about 125 mg/mL, about 50 mg/mL to about 150 mg/mL, about 50 mg/mL to about 175 mg/mL, about 50 mg/mL to about 200 mg/mL, about 50 mg/mL to about 225 mg/mL, about 50 mg/mL to about 250 mg/mL, about 50 mg/mL to about 275 mg/mL, about 50 mg/mL to about 300 mg/mL, about 50 mg/mL to about 325 mg/mL, about 50 mg/mL to about 350 mg/mL, about 50 mg/mL to about 375 mg/mL, about 50 mg/mL to about 400 mg/mL, about 50 mg/mL to about 425 mg/mL, about 50 mg/mL to about 450 mg/mL, about 50 mg/mL to about 475 mg/mL, about 50 mg/mL to about 500 mg/mL, about 100 mg/mL to about 150 mg/mL, about 100 mg/mL to about 200 mg/mL, about 100 mg/mL to about 250 mg/mL, about 100 mg/mL to about 300 mg/mL, about 100 mg/mL to about 350 mg/mL, about 100 mg/mL to about 400 mg/mL, about 100 mg/mL to about 450 mg/mL, about 100 mg/mL to about 500 mg/mL, about 200 mg/mL to about 300 mg/mL, about 200 mg/mL to about 400 mg/mL, about 200 mg/mL to about 500 mg/mL, about 200 mg/mL to about 600 mg/mL, about 200 mg/mL to about 700 mg/mL, about 200 mg/mL to about 800 mg/mL, about 200 mg/mL to about 900 mg/mL, or about 200 mg/mL to about 1000 mg/mL.

A therapeutic compound disclosed herein may be a non-opiate antitussive agent. As used herein, the term "non-opiate antitussive agent" refers to a class of non-opioid-based therapeutic compounds that act on the central and peripheral nervous systems to suppress the cough reflex. A non-opiate antitussive agent is preferably an NMDA antagonist. Examples of suitable non-opiate antitussive agents include, without limitation, Benproperine, Benzonate, Bibenzonium, Butamirate, Cloperastine, Clofedanol, Dextromethorphan, Dibunate, Dimemorfan, Dropropizine, Fedrilate, Indantadol, Isoaminile, Morclofone, Meprotixol, Nepinalone, Oxolamine, Oxeladin, Piperidione, Pentoxyverine, Prenoxdiazine, and Zipeprol.

A non-opiate antitussive agent may be in an amount suitable for its intended use. In aspects of this embodiment, a pharmaceutical composition comprises a non-opiate antitussive agent in an amount of, e.g., about 0.1 mg/mL, about 0.2 mg/mL, about 0.25 mg/mL, about 0.3 mg/mL, about 0.4 mg/mL, about 0.5 mg/mL, about 0.6 mg/mL, about 0.7 mg/mL, about 0.75 mg/mL, about 0.8 mg/mL, about 0.9 mg/mL, about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 14 mg/mL, about 15 mg/mL, about 16 mg/mL, about 17 mg/mL, about 18 mg/mL, about 19 mg/mL, about 20 mg/mL, about 21 mg/mL, about 22 mg/mL, about 23 mg/mL, about 24 mg/mL, about 25 mg/mL, about 26 mg/mL, about 27 mg/mL, about 28 mg/mL, about 29 mg/mL, or about 30 mg/mL. In other aspects of this embodiment, a pharmaceutical composition comprises a non-opiate antitussive agent in an amount of, e.g., at least 0.1 mg/mL, at least 0.2 mg/mL, at least 0.3 mg/mL, at least 0.4 mg/mL, at least 0.5 mg/mL, at least 0.6 mg/mL, at least 0.7 mg/mL, at least 0.8 mg/mL, at least 0.9 mg/mL, at least 1 mg/mL, at least 2 mg/mL, at least 3 mg/mL, at least 4 mg/mL, at least 5 mg/mL, at least 6 mg/mL, at least 7 mg/mL, at least 8 mg/mL, at least 9 mg/mL, at least 10 mg/mL, at least 11 mg/mL, at least 12 mg/mL, at least 13 mg/mL, at least 14 mg/mL, at least 15 mg/mL, at least 16 mg/mL, at least 17 mg/mL, at least 18 mg/mL, at least 19 mg/mL, at least 20 mg/mL, at least 21 mg/mL, at least 22 mg/mL, at least 23 mg/mL, at least 24 mg/mL, at least 25 mg/mL, at least 26 mg/mL, at least 27 mg/mL, at least 28 mg/mL, at least 29 mg/mL, or at least 30 mg/mL. In yet other aspects of this embodiment, a pharmaceutical composition comprises a non-opiate antitussive agent in an amount of, e.g., at most 0.1 mg/mL, at most 0.2 mg/mL, at most 0.3 mg/mL, at most 0.4 mg/mL, at most 0.5 mg/mL, at most 0.6 mg/mL, at most 0.7 mg/mL, at most 0.8 mg/mL, at most 0.9 mg/mL, at most 1 mg/mL, at most 2 mg/mL, at most 3 mg/mL, at most 4 mg/mL, at most 5 mg/mL, at most 6 mg/mL, at most 7 mg/mL, at most 8 mg/mL, at most 9 mg/mL, at most 10 mg/mL, at most 11 mg/mL, at most 12 mg/mL, at most 13 mg/mL, at most 14 mg/mL, at most 15 mg/mL, at most 16 mg/mL, at most 17 mg/mL, at most 18 mg/mL, at most 19 mg/mL, at most 20 mg/mL, at most 21 mg/mL, at most 22 mg/mL, at most 23 mg/mL, at most 24 mg/mL, at most 25 mg/mL, at most 26 mg/mL, at most 27 mg/mL, at most 28 mg/mL, at most 29 mg/mL, or at most 30 mg/mL In yet other aspects of this embodiment, a pharmaceutical composition comprises a non-opiate antitussive agent in an amount of, e.g., about 0.1 mg/mL to about 1 mg/mL, about 0.1 mg/mL to about 2 mg/mL, about 0.1 mg/mL to about 3 mg/mL, about 0.1 mg/mL to about 4 mg/mL, about 0.1 mg/mL to about 5 mg/mL, about 0.1 mg/mL to about 6 mg/mL, about 0.1 mg/mL to about 7 mg/mL, about 0.1 mg/mL to about 8 mg/mL, about 0.1 mg/mL to about 9 mg/mL, about 0.1 mg/mL to about 10 mg/mL, about 0.25 mg/mL to about 1 mg/mL, about 0.25 mg/mL to about 2 mg/mL, about 0.25 mg/mL to about 3 mg/mL, about 0.25 mg/mL to about 4 mg/mL, about 0.25 mg/mL to about 5 mg/mL, about 0.25 mg/mL to about 6 mg/mL, about 0.25 mg/mL to about 7 mg/mL, about 0.25 mg/mL to about 7.5 mg/mL, about 0.25 mg/mL to about 8 mg/mL, about 0.25 mg/mL to about 9 mg/mL, about 0.25 mg/mL to about 10 mg/mL, about 0.5 mg/mL to about 1 mg/mL, about 0.5 mg/mL to about 2 mg/mL, about 0.5 mg/mL to about 3 mg/mL, about 0.5 mg/mL to about 4 mg/mL, about 0.5 mg/mL to about 5 mg/mL, about 0.5 mg/mL to about 6 mg/mL, about 0.5 mg/mL to about 7 mg/mL, about 0.5 mg/mL to about 7.5 mg/mL, about 0.5 mg/mL to about 8 mg/mL, about 0.5 mg/mL to about 9 mg/mL, about 0.5 mg/mL to about 10 mg/mL, about 0.75 mg/mL to about 1 mg/mL, about 0.75 mg/mL to about 2 mg/mL, about 0.75 mg/mL to about 3 mg/mL, about 0.75 mg/mL to about 4 mg/mL, about 0.75 mg/mL to about 5 mg/mL, about 0.75 mg/mL to about 6 mg/mL, about 0.75 mg/mL to about 7 mg/mL, about 0.75 mg/mL to about 8 mg/mL, about 0.75 mg/mL to about 9 mg/mL, about 0.75 mg/mL to about 10 mg/mL, about 1 mg/mL to about 2 mg/mL, about 1 mg/mL to about 3 mg/mL, about 1 mg/mL to about 4 mg/mL, about 1 mg/mL to about 5 mg/mL, about 1 mg/mL to about 6 mg/mL, about 1 mg/mL to about 7 mg/mL, about 1 mg/mL to about 8 mg/mL, about 1 mg/mL to about 9 mg/mL, about 1 mg/mL to about 10 mg/mL, about 1 mg/mL to about 15 mg/mL, about 1 mg/mL to about 20 mg/mL, about 1 mg/mL to about 25 mg/mL, about 1 mg/mL to about 30 mg/mL, about 5 mg/mL to about 10 mg/mL, about 5 mg/mL to about 15 mg/mL, about 5 mg/mL to about 20 mg/mL, about 5 mg/mL to about 25 mg/mL, about 5 mg/mL to about 30 mg/mL, about 10 mg/mL to about 20 mg/mL, or about 10 mg/mL to about 30 mg/mL.

A therapeutic compound disclosed herein may be an opiate antitussive agent. As used herein, the term "opiate antitussive agent" refers to a class of opioid-based therapeutic compounds that act on the central and peripheral nervous systems to suppress the cough reflex. Examples of suitable opiates include, without limitation, Alfentanil, Alphamethylfentanyl, Buprenorphine, Carfentanyl, Codeine, Diamorphine, Dihydrocodeine, Ethyl Morphine, Etorphine, Fentanyl, Hydrocodone, Hydromorphone, Loperamide, Morphine, Noscapine, Oripavine, Oxymorphone, Oxycodone, Papaverine, Pentazocine, Pethidine, Propoxyphene, Remifentanil, Sufentanil, Thebaine, Tipepidine, and Tramadol.

An opiate antitussive agent may be in an amount suitable for its intended use. In aspects of this embodiment, a pharmaceutical composition comprises an opiate antitussive agent in an amount of, e.g., about 0.1 mg/mL, about 0.2 mg/mL, about 0.25 mg/mL, about 0.3 mg/mL, about 0.4 mg/mL, about 0.5 mg/mL, about 0.6 mg/mL, about 0.7 mg/mL, about 0.75 mg/mL, about 0.8 mg/mL, about 0.9 mg/mL, about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 14 mg/mL, about 15 mg/mL, about 16 mg/mL, about 17 mg/mL, about 18 mg/mL, about 19 mg/mL, about 20 mg/mL, about 21 mg/mL, about 22 mg/mL, about 23 mg/mL, about 24 mg/mL, about 25 mg/mL, about 26 mg/mL, about 27 mg/mL, about 28 mg/mL, about 29 mg/mL, or about 30 mg/mL. In other aspects of this embodiment, a pharmaceutical composition comprises an opiate antitussive agent in an amount of, e.g., at least 0.1 mg/mL, at least 0.2 mg/mL, at least 0.3 mg/mL, at least 0.4 mg/mL, at least 0.5 mg/mL, at least 0.6 mg/mL, at least 0.7 mg/mL, at least 0.8 mg/mL, at least 0.9 mg/mL, at least 1 mg/mL, at least 2 mg/mL, at least 3 mg/mL, at least 4 mg/mL, at least 5 mg/mL, at least 6 mg/mL, at least 7 mg/mL, at least 8 mg/mL, at least 9 mg/mL, at least 10 mg/mL, at least 11 mg/mL, at least 12 mg/mL, at least 13 mg/mL, at least 14 mg/mL, at least 15 mg/mL, at least 16 mg/mL, at least 17 mg/mL, at least 18 mg/mL, at least 19 mg/mL, at least 20 mg/mL, at least 21 mg/mL, at least 22 mg/mL, at least 23 mg/mL, at least 24 mg/mL, at least 25 mg/mL, at least 26 mg/mL, at least 27 mg/mL, at least 28 mg/mL, at least 29 mg/mL, or at least 30 mg/mL. In yet other aspects of this embodiment, a pharmaceutical composition comprises an opiate antitussive agent in an amount of, e.g., at most 0.1 mg/mL, at most 0.2 mg/mL, at most 0.3 mg/mL, at most 0.4 mg/mL, at most 0.5 mg/mL, at most 0.6 mg/mL, at most 0.7 mg/mL, at most 0.8 mg/mL, at most 0.9 mg/mL, at most 1 mg/mL, at most 2 mg/mL, at most 3 mg/mL, at most 4 mg/mL, at most 5 mg/mL, at most 6 mg/mL, at most 7 mg/mL, at most 8 mg/mL, at most 9 mg/mL, at most 10 mg/mL, at most 11 mg/mL, at most 12 mg/mL, at most 13 mg/mL, at most 14 mg/mL, at most 15 mg/mL, at most 16 mg/mL, at most 17 mg/mL, at most 18 mg/mL, at most 19 mg/mL, at most 20 mg/mL, at most 21 mg/mL, at most 22 mg/mL, at most 23 mg/mL, at most 24 mg/mL, at most 25 mg/mL, at most 26 mg/mL, at most 27 mg/mL, at most 28 mg/mL, at most 29 mg/mL, or at most 30 mg/mL In yet other aspects of this embodiment, a pharmaceutical composition comprises an opiate antitussive agent in an amount of, e.g., about 0.1 mg/mL to about 1 mg/mL, about 0.1 mg/mL to about 2 mg/mL, about 0.1 mg/mL to about 3 mg/mL, about 0.1 mg/mL to about 4 mg/mL, about 0.1 mg/mL to about 5 mg/mL, about 0.1 mg/mL to about 6 mg/mL, about 0.1 mg/mL to about 7 mg/mL, about 0.1 mg/mL to about 8 mg/mL, about 0.1 mg/mL to about 9 mg/mL, about 0.1 mg/mL to about 10 mg/mL, about 0.25 mg/mL to about 1 mg/mL, about 0.25 mg/mL to about 2 mg/mL, about 0.25 mg/mL to about 3 mg/mL, about 0.25 mg/mL to about 4 mg/mL, about 0.25 mg/mL to about 5 mg/mL, about 0.25 mg/mL to about 6 mg/mL, about 0.25 mg/mL to about 7 mg/mL, about 0.25 mg/mL to about 7.5 mg/mL, about 0.25 mg/mL to about 8 mg/mL, about 0.25 mg/mL to about 9 mg/mL, about 0.25 mg/mL to about 10 mg/mL, about 0.5 mg/mL to about 1 mg/mL, about 0.5 mg/mL to about 2 mg/mL, about 0.5 mg/mL to about 3 mg/mL, about 0.5 mg/mL to about 4 mg/mL, about 0.5 mg/mL to about 5 mg/mL, about 0.5 mg/mL to about 6 mg/mL, about 0.5 mg/mL to about 7 mg/mL, about 0.5 mg/mL to about 8 mg/mL, about 0.5 mg/mL to about 9 mg/mL, about 0.5 mg/mL to about 10 mg/mL, about 0.75 mg/mL to about 1 mg/mL, about 0.75 mg/mL to about 2 mg/mL, about 0.75 mg/mL to about 3 mg/mL, about 0.75 mg/mL to about 4 mg/mL, about 0.75 mg/mL to about 5 mg/mL, about 0.75 mg/mL to about 6 mg/mL, about 0.75 mg/mL to about 7 mg/mL, about 0.75 mg/mL to about 8 mg/mL, about 0.75 mg/mL to about 9 mg/mL, about 0.75 mg/mL to about 10 mg/mL, about 1 mg/mL to about 5 mg/mL, about 1 mg/mL to about 10 mg/mL, about 1 mg/mL to about 15 mg/mL, about 1 mg/mL to about 20 mg/mL, about 1 mg/mL to about 25 mg/mL, about 1 mg/mL to about 30 mg/mL, about 5 mg/mL to about 10 mg/mL, about 5 mg/mL to about 15 mg/mL, about 5 mg/mL to about 20 mg/mL, about 5 mg/mL to about 25 mg/mL, about 5 mg/mL to about 30 mg/mL, about 10 mg/mL to about 20 mg/mL, or about 10 mg/mL to about 30 mg/mL.

A therapeutic compound disclosed herein may be a decongestant. As used herein, the term "decongestant" refers to a class of therapeutic compounds that promote the secretion, liquefaction, or expulsion of sputum of phlegm or mucus from the respiratory tract. Decongestants act by causing the inflamed blood vessels in the nose and sinuses to constrict, thereby reducing inflammation and mucus formation. A decongestant is preferably an α-adrenergic receptor agonist. Examples of suitable decongestants include, without limitation, Ephedrine, Levmetamfetamine, Naphazoline, Oxymetazoline, Phenylephrine, Phenylpropanolamine, Propylhexedrine, Pseudoephedrine, Synephrine, and Tetrahydrozoline.

A decongestant may be in an amount suitable for its intended use. In aspects of this embodiment, a pharmaceutical composition comprises a decongestant in an amount of, e.g., about 0.1 mg/mL, about 0.2 mg/mL, about 0.25 mg/mL, about 0.3 mg/mL, about 0.4 mg/mL, about 0.5 mg/mL, about 0.6 mg/mL, about 0.7 mg/mL, about 0.75 mg/mL, about 0.8 mg/mL, about 0.9 mg/mL, about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 14 mg/mL, about 15 mg/mL, about 16 mg/mL, about 17 mg/mL, about 18 mg/mL, about 19 mg/mL, about 20 mg/mL, about 21 mg/mL, about 22 mg/mL, about 23 mg/mL, about 24 mg/mL, about 25 mg/mL, about 26 mg/mL, about 27 mg/mL, about 28 mg/mL, about 29 mg/mL, or about 30 mg/mL. In other aspects of this embodiment, a pharmaceutical composition comprises a decongestant in an amount of, e.g., at least 0.1 mg/mL, at least 0.2 mg/mL, at least 0.3 mg/mL, at least 0.4 mg/mL, at least 0.5 mg/mL, at least 0.6 mg/mL, at least 0.7 mg/mL, at least 0.8 mg/mL, at least 0.9 mg/mL, at least 1 mg/mL, at least 2 mg/mL, at least 3 mg/mL, at least 4 mg/mL, at least 5 mg/mL, at least 6 mg/mL, at least 7 mg/mL, at least 8 mg/mL, at least 9 mg/mL, at least 10 mg/mL, at least 11 mg/mL, at least 12 mg/mL, at least 13 mg/mL, at least 14 mg/mL, at least 15 mg/mL, at least 16 mg/mL, at least 17 mg/mL, at least 18 mg/mL, at least 19 mg/mL, at least 20 mg/mL, at least 21 mg/mL, at least 22 mg/mL, at least 23 mg/mL, at least 24 mg/mL, at least 25 mg/mL, at least 26 mg/mL, at least 27 mg/mL, at least 28 mg/mL, at least 29 mg/mL, or at least 30 mg/mL. In yet other aspects of this embodiment, a pharmaceutical composition comprises a decongestant in an amount of, e.g., at most 0.1 mg/mL, at most 0.2 mg/mL, at most 0.3 mg/mL, at most 0.4 mg/mL, at most 0.5 mg/mL, at most 0.6 mg/mL, at most 0.7 mg/mL, at most 0.8 mg/mL, at most 0.9 mg/mL, at most 1 mg/mL, at most 2 mg/mL, at most 3 mg/mL, at most 4 mg/mL, at most 5 mg/mL, at most 6 mg/mL, at most 7 mg/mL, at most 8 mg/mL, at most 9 mg/mL, at most 10 mg/mL, at most 11 mg/mL, at most 12 mg/mL, at most 13 mg/mL, at most 14 mg/mL, at most 15 mg/mL, at most 16 mg/mL, at most 17 mg/mL, at most 18 mg/mL, at most 19 mg/mL, at most 20 mg/mL, at most 21 mg/mL, at most 22 mg/mL, at most 23 mg/mL, at most 24 mg/mL, at most 25 mg/mL, at most 26 mg/mL, at most 27 mg/mL, at most 28 mg/mL, at most 29 mg/mL, or at most 30 mg/mL In yet other aspects of this embodiment, a pharmaceutical composition comprises a decongestant in an amount of, e.g., about 0.1 mg/mL to about 1 mg/mL, about 0.1 mg/mL to about 2 mg/mL, about 0.1 mg/mL to about 3 mg/mL, about 0.1 mg/mL to about 4 mg/mL, about 0.1 mg/mL to about 5 mg/mL, about 0.1 mg/mL to about 6 mg/mL, about 0.1 mg/mL to about 7 mg/mL, about 0.1 mg/mL to about 8 mg/mL, about 0.1 mg/mL to about 9 mg/mL, about 0.1 mg/mL to about 10 mg/mL, about 0.25 mg/mL to about 1 mg/mL, about 0.25 mg/mL to about 2 mg/mL, about 0.25 mg/mL to about 3 mg/mL, about 0.25 mg/mL to about 4 mg/mL, about 0.25 mg/mL to about 5 mg/mL, about 0.25 mg/mL to about 6 mg/mL, about 0.25 mg/mL to about 7 mg/mL, about 0.25 mg/mL to about 7.5 mg/mL, about 0.25 mg/mL to about 8 mg/mL, about 0.25 mg/mL to about 9 mg/mL, about 0.25 mg/mL to about 10 mg/mL, about 0.5 mg/mL to about 1 mg/mL, about 0.5 mg/mL to about 2 mg/mL, about 0.5 mg/mL to about 3 mg/mL, about 0.5 mg/mL to about 4 mg/mL, about 0.5 mg/mL to about 5 mg/mL, about 0.5 mg/mL to about 6 mg/mL, about 0.5 mg/mL to about 7 mg/mL, about 0.5 mg/mL to about 8 mg/mL, about 0.5 mg/mL to about 9 mg/mL, about 0.5 mg/mL to about 10 mg/mL, about 0.75 mg/mL to about 1 mg/mL, about 0.75 mg/mL to about 2 mg/mL, about 0.75 mg/mL to about 3 mg/mL, about 0.75 mg/mL to about 4 mg/mL, about 0.75 mg/mL to about 5 mg/mL, about 0.75 mg/mL to about 6 mg/mL, about 0.75 mg/mL to about 7 mg/mL, about 0.75 mg/mL to about 8 mg/mL, about 0.75 mg/mL to about 9 mg/mL, about 0.75 mg/mL to about 10 mg/mL, about 1 mg/mL to about 5 mg/mL, about 1 mg/mL to about 10 mg/mL, about 1 mg/mL to about 15 mg/mL, about 1 mg/mL to about 20 mg/mL, about 1 mg/mL to about 25 mg/mL, about 1 mg/mL to about 30 mg/mL, about 5 mg/mL to about 10 mg/mL, about 5 mg/mL to about 15 mg/mL, about 5 mg/mL to about 20 mg/mL, about 5 mg/mL to about 25 mg/mL, about 5 mg/mL to about 30 mg/mL, about 10 mg/mL to about 20 mg/mL, or about 10 mg/mL to about 30 mg/mL.

A therapeutic compound disclosed herein may be an expectorant. As used herein, the term "expectorant" refers to a class of therapeutic compounds that promote the secretion, liquefaction, or expulsion of sputum of phlegm or mucus from the respiratory tract. Expectorants work by breaking the bonds between mucoproteins that create the thickness or viscosity of mucus in the respiratory tract, thereby increasing mucus flow and making it easier to remove from the body through coughing. Examples of suitable expectorants include, without limitation, Ambroxol, Ammonium Bicarbonate, Ammonium Carbonate, Bromhexine, Calcium Iodide, Carbocysteine, Guaiacol, Guaiacol Benzoate, Guaiacol Carbonate, Guaiacol Phosphate, Guaifenesin, Guaithylline, Hydriodic Acid, Iodinated Glycerol, Potassium Guaiacolsulfonate, Potassium Iodide, Sodium Citrate, Sodium Iodide, Storax Terebene, Terpin, Trifolium, Althea Root, Antimony Pentasulfide, Creosote, Ipecacuanha (Syrup of Ipecac), Levoverbenone, Senega, and Tyloxapol.

An expectorant may be in an amount suitable for its intended use. In aspects of this embodiment, a pharmaceutical composition comprises an expectorant in an amount of, e.g., about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 14 mg/mL, about 15 mg/mL, about 16 mg/mL, about 17 mg/mL, about 18 mg/mL, about 19 mg/mL, about 20 mg/mL, about 21 mg/mL, about 22 mg/mL, about 23 mg/mL, about 24 mg/mL, about 25 mg/mL, about 26 mg/mL, about 27 mg/mL, about 28 mg/mL, about 29 mg/mL, or about 30 mg/mL. In other aspects of this embodiment, a pharmaceutical composition comprises an expectorant in an amount of, e.g., at least 0.1 mg/mL, at least 0.2 mg/mL, at least 0.3 mg/mL, at least 0.4 mg/mL, at least 0.5 mg/mL, at least 0.6 mg/mL, at least 0.7 mg/mL, at least 0.8 mg/mL, at least 0.9 mg/mL, at least 1 mg/mL, at least 2 mg/mL, at least 3 mg/mL, at least 4 mg/mL, at least 5 mg/mL, at least 6 mg/mL, at least 7 mg/mL, at least 8 mg/mL, at least 9 mg/mL, at least 10 mg/mL, at least 11 mg/mL, at least 12 mg/mL, at least 13 mg/mL, at least 14 mg/mL, at least 15 mg/mL, at least 16 mg/mL, at least 17 mg/mL, at least 18 mg/mL, at least 19 mg/mL, at least 20 mg/mL, at least 21 mg/mL, at least 22 mg/mL, at least 23 mg/mL, at least 24 mg/mL, at least 25 mg/mL, at least 26 mg/mL, at least 27 mg/mL, at least 28 mg/mL, at least 29 mg/mL, or at least 30 mg/mL. In yet other aspects of this embodiment, a pharmaceutical composition comprises an expectorant in an amount of, e.g., at most 0.1 mg/mL, at most 0.2 mg/mL, at most 0.3 mg/mL, at most 0.4 mg/mL, at most 0.5 mg/mL, at most 0.6 mg/mL, at most 0.7 mg/mL, at most 0.8 mg/mL, at most 0.9 mg/mL, at most 1 mg/mL, at most 2 mg/mL, at most 3 mg/mL, at most 4 mg/mL, at most 5 mg/mL, at most 6 mg/mL, at most 7 mg/mL, at most 8 mg/mL, at most 9 mg/mL, at most 10 mg/mL, at most 11 mg/mL, at most 12 mg/mL, at most 13 mg/mL, at most 14 mg/mL, at most 15 mg/mL, at most 16 mg/mL, at most 17 mg/mL, at most 18 mg/mL, at most 19 mg/mL, at most 20 mg/mL, at most 21 mg/mL, at most 22 mg/mL, at most 23 mg/mL, at most 24 mg/mL, at most 25 mg/mL, at most 26 mg/mL, at most 27 mg/mL, at most 28 mg/mL, at most 29 mg/mL, or at most 30 mg/mL In yet other aspects of this embodiment, a pharmaceutical composition comprises an expectorant in an amount of, e.g., about 0.1 mg/mL to about 1 mg/mL, about 0.1 mg/mL to about 2 mg/mL, about 0.1 mg/mL to about 3 mg/mL, about 0.1 mg/mL to about 4 mg/mL, about 0.1 mg/mL to about 5 mg/mL, about 0.1 mg/mL to about 6 mg/mL, about 0.1 mg/mL to about 7 mg/mL, about 0.1 mg/mL to about 8 mg/mL, about 0.1 mg/mL to about 9 mg/mL, about 0.1 mg/mL to about 10 mg/mL, about 0.25 mg/mL to about 1 mg/mL, about 0.25 mg/mL to about 2 mg/mL, about 0.25 mg/mL to about 3 mg/mL, about 0.25 mg/mL to about 4 mg/mL, about 0.25 mg/mL to about 5 mg/mL, about 0.25 mg/mL to about 6 mg/mL, about 0.25 mg/mL to about 7 mg/mL, about 0.25 mg/mL to about 7.5 mg/mL, about 0.25 mg/mL to about 8 mg/mL, about 0.25 mg/mL to about 9 mg/mL, about 0.25 mg/mL to about 10 mg/mL, about 0.5 mg/mL to about 1 mg/mL, about 0.5 mg/mL to about 2 mg/mL, about 0.5 mg/mL to about 3 mg/mL, about 0.5 mg/mL to about 4 mg/mL, about 0.5 mg/mL to about 5 mg/mL, about 0.5 mg/mL to about 6 mg/mL, about 0.5 mg/mL to about 7 mg/mL, about 0.5 mg/mL to about 8 mg/mL, about 0.5 mg/mL to about 9 mg/mL, about 0.5 mg/mL to about 10 mg/mL, about 0.75 mg/mL to about 1 mg/mL, about 0.75 mg/mL to about 2 mg/mL, about 0.75 mg/mL to about 3 mg/mL, about 0.75 mg/mL to about 4 mg/mL, about 0.75 mg/mL to about 5 mg/mL, about 0.75 mg/mL to about 6 mg/mL, about 0.75 mg/mL to about 7 mg/mL, about 0.75 mg/mL to about 8 mg/mL, about 0.75 mg/mL to about 9 mg/mL, about 0.75 mg/mL to about 10 mg/mL, about 1 mg/mL to about 5 mg/mL, about 1 mg/mL to about 10 mg/mL, about 1 mg/mL to about 15 mg/mL, about 1 mg/mL to about 20 mg/mL, about 1 mg/mL to about 25 mg/mL, about 1 mg/mL to about 30 mg/mL, about 5 mg/mL to about 10 mg/mL, about 5 mg/mL to about 15 mg/mL, about 5 mg/mL to about 20 mg/mL, about 5 mg/mL to about 25 mg/mL, about 5 mg/mL to about 30 mg/mL, about 10 mg/mL to about 20 mg/mL, or about 10 mg/mL to about 30 mg/mL.

A therapeutic compound disclosed herein may be a mucolytic agent. As used herein, the term "mucolytic agent" refers to a class of therapeutic compounds that promote the secretion, liquefaction, or expulsion of sputum of phlegm or mucus from the respiratory tract. Examples of suitable mucolytic agents include, without limitation, Acetylcysteine, Bromhexine, Carbocysteine, Domiodol, Erdostine, Letostine, Lysozyme, Mecysteine Hydrochloride, Mesna, Sobrerol, Stepronin, Tiopronin, Tyloxapol, Ambroxol, Ammonium Chloride, Dornase Alfa, Eprazinone, Erdosteine, Letosteine, and Neltenexine.

A mucolytic agent may be in an amount suitable for its intended use. In aspects of this embodiment, a pharmaceutical composition comprises a mucolytic agent in an amount of, e.g., about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 14 mg/mL, about 15 mg/mL, about 16 mg/mL, about 17 mg/mL, about 18 mg/mL, about 19 mg/mL, about 20 mg/mL, about 21 mg/mL, about 22 mg/mL, about 23 mg/mL, about 24 mg/mL, about 25 mg/mL, about 26 mg/mL, about 27 mg/mL, about 28 mg/mL, about 29 mg/mL, or about 30 mg/mL. In other aspects of this embodiment, a pharmaceutical composition comprises a mucolytic agent in an amount of, e.g., at least 0.1 mg/mL, at least 0.2 mg/mL, at least 0.3 mg/mL, at least 0.4 mg/mL, at least 0.5 mg/mL, at least 0.6 mg/mL, at least 0.7 mg/mL, at least 0.8 mg/mL, at least 0.9 mg/mL, at least 1 mg/mL, at least 2 mg/mL, at least 3 mg/mL, at least 4 mg/mL, at least 5 mg/mL, at least 6 mg/mL, at least 7 mg/mL, at least 8 mg/mL, at least 9 mg/mL, at least 10 mg/mL, at least 11 mg/mL, at least 12 mg/mL, at least 13 mg/mL, at least 14 mg/mL, at least 15 mg/mL, at least 16 mg/mL, at least 17 mg/mL, at least 18 mg/mL, at least 19 mg/mL, at least 20 mg/mL, at least 21 mg/mL, at least 22 mg/mL, at least 23 mg/mL, at least 24 mg/mL, at least 25 mg/mL, at least 26 mg/mL, at least 27 mg/mL, at least 28 mg/mL, at least 29 mg/mL, or at least 30 mg/mL. In yet other aspects of this embodiment, a pharmaceutical composition comprises a mucolytic agent in an amount of, e.g., at most 0.1 mg/mL, at most 0.2 mg/mL, at most 0.3 mg/mL, at most 0.4 mg/mL, at most 0.5 mg/mL, at most 0.6 mg/mL, at most 0.7 mg/mL, at most 0.8 mg/mL, at most 0.9 mg/mL, at most 1 mg/mL, at most 2 mg/mL, at most 3 mg/mL, at most 4 mg/mL, at most 5 mg/mL, at most 6 mg/mL, at most 7 mg/mL, at most 8 mg/mL, at most 9 mg/mL, at most 10 mg/mL, at most 11 mg/mL, at most 12 mg/mL, at most 13 mg/mL, at most 14 mg/mL, at most 15 mg/mL, at most 16 mg/mL, at most 17 mg/mL, at most 18 mg/mL, at most 19 mg/mL, at most 20 mg/mL, at most 21 mg/mL, at most 22 mg/mL, at most 23 mg/mL, at most 24 mg/mL, at most 25 mg/mL, at most 26 mg/mL, at most 27 mg/mL, at most 28 mg/mL, at most 29 mg/mL, or at most 30 mg/mL In yet other aspects of this embodiment, a pharmaceutical composition comprises a mucolytic agent in an amount of, e.g., about 0.1 mg/mL to about 1 mg/mL, about 0.1 mg/mL to about 2 mg/mL, about 0.1 mg/mL to about 3 mg/mL, about 0.1 mg/mL to about 4 mg/mL, about 0.1 mg/mL to about 5 mg/mL, about 0.1 mg/mL to about 6 mg/mL, about 0.1 mg/mL to about 7 mg/mL, about 0.1 mg/mL to about 8 mg/mL, about 0.1 mg/mL to about 9 mg/mL, about 0.1 mg/mL to about 10 mg/mL, about 0.25 mg/mL to about 1 mg/mL, about 0.25 mg/mL to about 2 mg/mL, about 0.25 mg/mL to about 3 mg/mL, about 0.25 mg/mL to about 4 mg/mL, about 0.25 mg/mL to about 5 mg/mL, about 0.25 mg/mL to about 6 mg/mL, about 0.25 mg/mL to about 7 mg/mL, about 0.25 mg/mL to about 7.5 mg/mL, about 0.25 mg/mL to about 8 mg/mL, about 0.25 mg/mL to about 9 mg/mL, about 0.25 mg/mL to about 10 mg/mL, about 0.5 mg/mL to about 1 mg/mL, about 0.5 mg/mL to about 2 mg/mL, about 0.5 mg/mL to about 3 mg/mL, about 0.5 mg/mL to about 4 mg/mL, about 0.5 mg/mL to about 5 mg/mL, about 0.5 mg/mL to about 6 mg/mL, about 0.5 mg/mL to about 7 mg/mL, about 0.5 mg/mL to about 8 mg/mL, about 0.5 mg/mL to about 9 mg/mL, about 0.5 mg/mL to about 10 mg/mL, about 0.75 mg/mL to about 1 mg/mL, about 0.75 mg/mL to about 2 mg/mL, about 0.75 mg/mL to about 3 mg/mL, about 0.75 mg/mL to about 4 mg/mL, about 0.75 mg/mL to about 5 mg/mL, about 0.75 mg/mL to about 6 mg/mL, about 0.75 mg/mL to about 7 mg/mL, about 0.75 mg/mL to about 8 mg/mL, about 0.75 mg/mL to about 9 mg/mL, about 0.75 mg/mL to about 10 mg/mL, about 1 mg/mL to about 5 mg/mL, about 1 mg/mL to about 10 mg/mL, about 1 mg/mL to about 15 mg/mL, about 1 mg/mL to about 20 mg/mL, about 1 mg/mL to about 25 mg/mL, about 1 mg/mL to about 30 mg/mL, about 5 mg/mL to about 10 mg/mL, about 5 mg/mL to about 15 mg/mL, about 5 mg/mL to about 20 mg/mL, about 5 mg/mL to about 25 mg/mL, about 5 mg/mL to about 30 mg/mL, about 10 mg/mL to about 20 mg/mL, or about 10 mg/mL to about 30 mg/mL.

A therapeutic compound disclosed herein may be an anti-histamine. As used herein, the term "antihistamine" refers to a class of therapeutic compounds that inhibits the action of histamine via one or more histamine receptors.

Typically, an anti-histamine blocking H1 receptors is used to treat coughing, a cold, and/or an allergic reaction. Examples of suitable antihistamines include, without limitation, Acrivastine, Alimemazine, Astemizole, Azatadine, Bromodiphenhydramine, Brompheniramine, Carbinoxamine, Cetirizine, Chlorpheniramine, Clemastine, Cyproheptadine, Desloratadine, Dexchlorpheniramine, Dextrobrompheniramine, Dimenhydrinate, Diphenhydramine, Doxylamine, Fexofenadine, Hydroxyzine, Levocetirizine, Loratadine, Meclizine, Mizolastine, Quetiapine, Pheniramine, Promethazine, Pyrilamine, Tripelennamine, and Triprolidine.

An antihistamine may be in an amount suitable for its intended use. In aspects of this embodiment, a pharmaceutical composition comprises an antihistamine in an amount of, e.g., about 0.1 mg/mL, about 0.2 mg/mL, about 0.25 mg/mL, about 0.3 mg/mL, about 0.4 mg/mL, about 0.5 mg/mL, about 0.6 mg/mL, about 0.7 mg/mL, about 0.75 mg/mL, about 0.8 mg/mL, about 0.9 mg/mL, about 1 mg/mL, about 1.25 mg/mL, about 1.5 mg/mL, about 1.75 mg/mL, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 14 mg/mL, about 15 mg/mL, about 16 mg/mL, about 17 mg/mL, about 18 mg/mL, about 19 mg/mL, about 20 mg/mL, about 21 mg/mL, about 22 mg/mL, about 23 mg/mL, about 24 mg/mL, about 25 mg/mL, about 26 mg/mL, about 27 mg/mL, about 28 mg/mL, about 29 mg/mL, or about 30 mg/mL. In other aspects of this embodiment, a pharmaceutical composition comprises an antihistamine in an amount of, e.g., at least 0.1 mg/mL, at least 0.2 mg/mL, at least 0.3 mg/mL, at least 0.4 mg/mL, at least 0.5 mg/mL, at least 0.6 mg/mL, at least 0.7 mg/mL, at least 0.8 mg/mL, at least 0.9 mg/mL, at least 1 mg/mL, at least 2 mg/mL, at least 3 mg/mL, at least 4 mg/mL, at least 5 mg/mL, at least 6 mg/mL, at least 7 mg/mL, at least 8 mg/mL, at least 9 mg/mL, at least 10 mg/mL, at least 11 mg/mL, at least 12 mg/mL, at least 13 mg/mL, at least 14 mg/mL, at least 15 mg/mL, at least 16 mg/mL, at least 17 mg/mL, at least 18 mg/mL, at least 19 mg/mL, at least 20 mg/mL, at least 21 mg/mL, at least 22 mg/mL, at least 23 mg/mL, at least 24 mg/mL, at least 25 mg/mL, at least 26 mg/mL, at least 27 mg/mL, at least 28 mg/mL, at least 29 mg/mL, or at least 30 mg/mL. In yet other aspects of this embodiment, a pharmaceutical composition comprises an antihistamine in an amount of, e.g., at most 0.1 mg/mL, at most 0.2 mg/mL, at most 0.3 mg/mL, at most 0.4 mg/mL, at most 0.5 mg/mL, at most 0.6 mg/mL, at most 0.7 mg/mL, at most 0.8 mg/mL, at most 0.9 mg/mL, at most 1 mg/mL, at most 2 mg/mL, at most 3 mg/mL, at most 4 mg/mL, at most 5 mg/mL, at most 6 mg/mL, at most 7 mg/mL, at most 8 mg/mL, at most 9 mg/mL, at most 10 mg/mL, at most 11 mg/mL, at most 12 mg/mL, at most 13 mg/mL, at most 14 mg/mL, at most 15 mg/mL, at most 16 mg/mL, at most 17 mg/mL, at most 18 mg/mL, at most 19 mg/mL, at most 20 mg/mL, at most 21 mg/mL, at most 22 mg/mL, at most 23 mg/mL, at most 24 mg/mL, at most 25 mg/mL, at most 26 mg/mL, at most 27 mg/mL, at most 28 mg/mL, at most 29 mg/mL, or at most 30 mg/mL In yet other aspects of this embodiment, a pharmaceutical composition comprises an antihistamine in an amount of, e.g., about 0.1 mg/mL to about 1 mg/mL, about 0.1 mg/mL to about 2 mg/mL, about 0.1 mg/mL to about 3 mg/mL, about 0.1 mg/mL to about 4 mg/mL, about 0.1 mg/mL to about 5 mg/mL, about 0.1 mg/mL to about 6 mg/mL, about 0.1 mg/mL to about 7 mg/mL, about 0.1 mg/mL to about 8 mg/mL, about 0.1 mg/mL to about 9 mg/mL, about 0.1 mg/mL to about 10 mg/mL, about 0.25 mg/mL to about 1 mg/mL, about 0.25 mg/mL to about 2 mg/mL, about 0.25 mg/mL to about 3 mg/mL, about 0.25 mg/mL to about 4 mg/mL, about 0.25 mg/mL to about 5 mg/mL, about 0.25 mg/mL to about 6 mg/mL, about 0.25 mg/mL to about 7 mg/mL, about 0.25 mg/mL to about 7.5 mg/mL, about 0.25 mg/mL to about 8 mg/mL, about 0.25 mg/mL to about 9 mg/mL, about 0.25 mg/mL to about 10 mg/mL, about 0.5 mg/mL to about 1 mg/mL, about 0.5 mg/mL to about 2 mg/mL, about 0.5 mg/mL to about 3 mg/mL, about 0.5 mg/mL to about 4 mg/mL, about 0.5 mg/mL to about 5 mg/mL, about 0.5 mg/mL to about 6 mg/mL, about 0.5 mg/mL to about 7 mg/mL, about 0.5 mg/mL to about 8 mg/mL, about 0.5 mg/mL to about 9 mg/mL, about 0.5 mg/mL to about 10 mg/mL, about 0.75 mg/mL to about 1 mg/mL, about 0.75 mg/mL to about 2 mg/mL, about 0.75 mg/mL to about 3 mg/mL, about 0.75 mg/mL to about 4 mg/mL, about 0.75 mg/mL to about 5 mg/mL, about 0.75 mg/mL to about 6 mg/mL, about 0.75 mg/mL to about 7 mg/mL, about 0.75 mg/mL to about 8 mg/mL, about 0.75 mg/mL to about 9 mg/mL, about 0.75 mg/mL to about 10 mg/mL, about 1 mg/mL to about 5 mg/mL, about 1 mg/mL to about 10 mg/mL, about 1 mg/mL to about 15 mg/mL, about 1 mg/mL to about 20 mg/mL, about 1 mg/mL to about 25 mg/mL, about 1 mg/mL to about 30 mg/mL, about 5 mg/mL to about 10 mg/mL, about 5 mg/mL to about 15 mg/mL, about 5 mg/mL to about 20 mg/mL, about 5 mg/mL to about 25 mg/mL, about 5 mg/mL to about 30 mg/mL, about 10 mg/mL to about 20 mg/mL, or about 10 mg/mL to about 30 mg/mL.

A therapeutic compound disclosed herein may be a NSAID. As used herein, the term "NSAID" refers to a class of therapeutic compounds with analgesic, anti-inflammatory, and anti-pyretic properties. NSAIDs reduce inflammation by blocking cyclooxygenase. NSAIDs may be classified based on their chemical structure or mechanism of action. Non-limiting examples of NSAIDs include a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclo-oxygenase (COX) inhibitor, a selective cyclooxygenase 1 (COX 1) inhibitor, and a selective cyclooxygenase 2 (COX 2) inhibitor. A NSAID may be a profen. Examples of a suitable salicylate derivative NSAID include, without limitation, Acetylsalicylic acid (asprin), Diflunisal, Hydroxyethyl Salicylate, and Salsalate. Examples of a suitable p-amino phenol derivative NSAID include, without limitation, Paracetamol and Phenacetin. Examples of a suitable propionic acid derivative NSAID include, without limitation, Alminoprofen, Benoxaprofen, Dexketoprofen, Fenoprofen, Flurbiprofen, Ibuprofen, Indoprofen, Ketoprofen, Loxoprofen, Naproxen, Oxaprozin, Pranoprofen, And Suprofen. Examples Of A Suitable Acetic Acid Derivative NSAID Include, Without Limitation, Aceclofenac, Acemetacin, Actarit, Alcofenac, Aloxipirin, Amfenac, Aminophenazone, Antraphenine, Azapropazone, Benorilate, Benzydamine, Butibufen, Chlorthenoxacine, Choline Salicylate, Clometacin, Diclofenac, Emorfazone, Epirizole, Etodolac, Feclobuzone, Felbinac, Fenbufen, Fenclofenac, Glafenine, Indometacin, Ketorolac, Lactyl Phenetidin, Metamizole, Metiazinic Acid, Mofebutazone, Mofezolac, Nabumetone, Nifenazone, Niflumic Acid, Oxametacin, Pipebuzone, Propyphenazone, Proquazone, Protozininc Acid, Salicylamide, Sulindac, Tiaramide, Tinoridine, And Zomepirac. Examples of a suitable enolic acid (Oxicam) derivative NSAID include, without limitation, Droxicam, Isoxicam, Lornoxicam, Meloxicam, Piroxicam, and Tenoxicam. Examples of a suitable fenamic acid derivative NSAID include, without limitation, Flufenamic acid, Mefenamic acid, Meclofenamic acid, and Tolfenamic acid. Examples of a suitable selective COX-2 inhibitors include, without limitation, Celecoxib, Etoricoxib, Firocoxib, Lumiracoxib, Meloxicam, Parecoxib, Rofecoxib, and Valdecoxib.

A NSAID may be in an amount suitable for its intended use. In aspects of this embodiment, a pharmaceutical composition comprises a NSAID in an amount of, e.g., about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 14 mg/mL, about 15 mg/mL, about 16 mg/mL, about 17 mg/mL, about 18 mg/mL, about 19 mg/mL, about 20 mg/mL, about 21 mg/mL, about 22 mg/mL, about 23 mg/mL, about 24 mg/mL, about 25 mg/mL, about 26 mg/mL, about 27 mg/mL, about 28 mg/mL, about 29 mg/mL, or about 30 mg/mL In other aspects of this embodiment, a pharmaceutical composition comprises a NSAID in an amount of, e.g., about 10 mg/mL, about 20 mg/mL, about 30 mg/mL, about 40 mg/mL, about 50 mg/mL, about 60 mg/mL, about 70 mg/mL, about 80 mg/mL, about 90 mg/mL, about 100 mg/mL, about 125 mg/mL, about 150 mg/mL, about 175 mg/mL, about 200 mg/mL, about 225 mg/mL, about 250 mg/mL, about 275 mg/mL, about 300 mg/mL, about 325 mg/mL, about 350 mg/mL, about 375 mg/mL, about 400 mg/mL, about 425 mg/mL, about 450 mg/mL, about 475 mg/mL, about 500 mg/mL, about 525 mg/mL, about 550 mg/mL, about 575 mg/mL, about 600 mg/mL, about 625 mg/mL, about 650 mg/mL, about 675 mg/mL, about 700 mg/mL, about 725 mg/mL, about 750 mg/mL, about 775 mg/mL, about 800 mg/mL, about 825 mg/mL, about 850 mg/mL, about 875 mg/mL, about 900 mg/mL, about 925 mg/mL, about 950 mg/mL, about 975 mg/mL, or about 1000 mg/mL.

In other aspects of this embodiment, a pharmaceutical composition comprises a NSAID in an amount of, e.g., at least 0.1 mg/mL, at least 0.2 mg/mL, at least 0.3 mg/mL, at least 0.4 mg/mL, at least 0.5 mg/mL, at least 0.6 mg/mL, at least 0.7 mg/mL, at least 0.8 mg/mL, at least 0.9 mg/mL, at least 1 mg/mL, at least 2 mg/mL, at least 3 mg/mL, at least 4 mg/mL, at least 5 mg/mL, at least 6 mg/mL, at least 7 mg/mL, at least 8 mg/mL, at least 9 mg/mL, at least 10 mg/mL, at least 11 mg/mL, at least 12 mg/mL, at least 13 mg/mL, at least 14 mg/mL, at least 15 mg/mL, at least 16 mg/mL, at least 17 mg/mL, at least 18 mg/mL, at least 19 mg/mL, at least 20 mg/mL, at least 21 mg/mL, at least 22 mg/mL, at least 23 mg/mL, at least 24 mg/mL, at least 25 mg/mL, at least 26 mg/mL, at least 27 mg/mL, at least 28 mg/mL, at least 29 mg/mL, or at least 30 mg/mL In aspects of this embodiment, a pharmaceutical composition comprises a NSAID in an amount of, e.g., at least 10 mg/mL, at least 20 mg/mL, at least 30 mg/mL, at least 40 mg/mL, at least 50 mg/mL, at least 60 mg/mL, at least 70 mg/mL, at least 80 mg/mL, at least 90 mg/mL, at least 100 mg/mL, at least 125 mg/mL, at least 150 mg/mL, at least 175 mg/mL, at least 200 mg/mL, at least 225 mg/mL, at least 250 mg/mL, at least 275 mg/mL, at least 300 mg/mL, at least 325 mg/mL, at least 350 mg/mL, at least 375 mg/mL, at least 400 mg/mL, at least 425 mg/mL, at least 450 mg/mL, at least 475 mg/mL, at least 500 mg/mL, at least 525 mg/mL, at least 550 mg/mL, at least 575 mg/mL, at least 600 mg/mL, at least 625 mg/mL, at least 650 mg/mL, at least 675 mg/mL, at least 700 mg/mL, at least 725 mg/mL, at least 750 mg/mL, at least 775 mg/mL, at least 800 mg/mL, at least 825 mg/mL, at least 850 mg/mL, at least 875 mg/mL, at least 900 mg/mL, at least 925 mg/mL, at least 950 mg/mL, at least 975 mg/mL, or at least 1000 mg/mL.

In other aspects of this embodiment, a pharmaceutical composition comprises a NSAID in an amount of, e.g., at most 0.1 mg/mL, at most 0.2 mg/mL, at most 0.3 mg/mL, at most 0.4 mg/mL, at most 0.5 mg/mL, at most 0.6 mg/mL, at most 0.7 mg/mL, at most 0.8 mg/mL, at most 0.9 mg/mL, at most 1 mg/mL, at most 2 mg/mL, at most 3 mg/mL, at most 4 mg/mL, at most 5 mg/mL, at most 6 mg/mL, at most 7 mg/mL, at most 8 mg/mL, at most 9 mg/mL, at most 10 mg/mL, at most 11 mg/mL, at most 12 mg/mL, at most 13 mg/mL, at most 14 mg/mL, at most 15 mg/mL, at most 16 mg/mL, at most 17 mg/mL, at most 18 mg/mL, at most 19 mg/mL, at most 20 mg/mL, at most 21 mg/mL, at most 22 mg/mL, at most 23 mg/mL, at most 24 mg/mL, at most 25 mg/mL, at most 26 mg/mL, at most 27 mg/mL, at most 28 mg/mL, at most 29 mg/mL, or at most 30 mg/mL In yet other aspects of this embodiment, a NSAID is in an amount of, e.g., at most 10 mg/mL, at most 20 mg/mL, at most 30 mg/mL, at most 40 mg/mL, at most 50 mg/mL, at most 60 mg/mL, at most 70 mg/mL, at most 80 mg/mL, at most 90 mg/mL, at most 100 mg/mL, at most 125 mg/mL, at most 150 mg/mL, at most 175 mg/mL, at most 200 mg/mL, at most 225 mg/mL, at most 250 mg/mL, at most 275 mg/mL, at most 300 mg/mL, at most 325 mg/mL, at most 350 mg/mL, at most 375 mg/mL, at most 400 mg/mL, at most 425 mg/mL, at most 450 mg/mL, at most 475 mg/mL, at most 500 mg/mL, at most 525 mg/mL, at most 550 mg/mL, at most 575 mg/mL, at most 600 mg/mL, at most 625 mg/mL, at most 650 mg/mL, at most 675 mg/mL, at most 700 mg/mL, at most 725 mg/mL, at most 750 mg/mL, at most 775 mg/mL, at most 800 mg/mL, at most 825 mg/mL, at most 850 mg/mL, at most 875 mg/mL, at most 900 mg/mL, at most 925 mg/mL, at most 950 mg/mL, at most 975 mg/mL, or at most 1000 mg/mL.

In other aspects of this embodiment, a pharmaceutical composition comprises a NSAID in an amount of, e.g., about 0.1 mg/mL to about 1 mg/mL, about 0.1 mg/mL to about 2 mg/mL, about 0.1 mg/mL to about 3 mg/mL, about 0.1 mg/mL to about 4 mg/mL, about 0.1 mg/mL to about 5 mg/mL, about 0.1 mg/mL to about 6 mg/mL, about 0.1 mg/mL to about 7 mg/mL, about 0.1 mg/mL to about 8 mg/mL, about 0.1 mg/mL to about 9 mg/mL, about 0.1 mg/mL to about 10 mg/mL, about 0.25 mg/mL to about 1 mg/mL, about 0.25 mg/mL to about 2 mg/mL, about 0.25 mg/mL to about 3 mg/mL, about 0.25 mg/mL to about 4 mg/mL, about 0.25 mg/mL to about 5 mg/mL, about 0.25 mg/mL to about 6 mg/mL, about 0.25 mg/mL to about 7 mg/mL, about 0.25 mg/mL to about 7.5 mg/mL, about 0.25 mg/mL to about 8 mg/mL, about 0.25 mg/mL to about 9 mg/mL, about 0.25 mg/mL to about 10 mg/mL, about 0.5 mg/mL to about 1 mg/mL, about 0.5 mg/mL to about 2 mg/mL, about 0.5 mg/mL to about 3 mg/mL, about 0.5 mg/mL to about 4 mg/mL, about 0.5 mg/mL to about 5 mg/mL, about 0.5 mg/mL to about 6 mg/mL, about 0.5 mg/mL to about 7 mg/mL, about 0.5 mg/mL to about 8 mg/mL, about 0.5 mg/mL to about 9 mg/mL, about 0.5 mg/mL to about 10 mg/mL, about 1 mg/mL to about 5 mg/mL, about 1 mg/mL to about 10 mg/mL, about 1 mg/mL to about 15 mg/mL, about 1 mg/mL to about 20 mg/mL, about 1 mg/mL to about 25 mg/mL, about 1 mg/mL to about 30 mg/mL, about 1 mg/mL to about 35 mg/mL, about 1 mg/mL to about 40 mg/mL, about 1 mg/mL to about 45 mg/mL, about 1 mg/mL to about 50 mg/mL, about 5 mg/mL to about 10 mg/mL, about 5 mg/mL to about 15 mg/mL, about 5 mg/mL to about 20 mg/mL, about 5 mg/mL to about 25 mg/mL, about 5 mg/mL to about 30 mg/mL, about 5 mg/mL to about 35 mg/mL, about 5 mg/mL to about 40 mg/mL, about 5 mg/mL to about 45 mg/mL, about 5 mg/mL to about 50 mg/mL, about 10 mg/mL to about 20 mg/mL, about 10 mg/mL to about 30 mg/mL, about 10 mg/mL to about 40 mg/mL, about 10 mg/mL to about 50 mg/mL, about 10 mg/mL to about 60 mg/mL, about 10 mg/mL to about 70 mg/mL, about 10 mg/mL to about 80 mg/mL, about 10 mg/mL to about 90 mg/mL, about 10 mg/mL to about 100 mg/mL, about 25 mg/mL to about 50 mg/mL, about 25 mg/mL to about 75 mg/mL, about 25 mg/mL to about 100 mg/mL, about 25 mg/mL to about 125 mg/mL, about 25 mg/mL to about 150 mg/mL, about 25 mg/mL to about 175 mg/mL, about 25 mg/mL to about 200 mg/mL, about 25 mg/mL to about 225 mg/mL, about 25 mg/mL to about 250 mg/mL, about 50 mg/mL to about 75 mg/mL, about 50 mg/mL to about 100 mg/mL, about 50 mg/mL to about 125 mg/mL, about 50 mg/mL to about 150 mg/mL, about 50 mg/mL to about 175 mg/mL, about 50 mg/mL to about 200 mg/mL, about 50 mg/mL to about 225 mg/mL, about 50 mg/mL to about 250 mg/mL, about 50 mg/mL to about 275 mg/mL, about 50 mg/mL to about 300 mg/mL, about 50 mg/mL to about 325 mg/mL, about 50 mg/mL to about 350 mg/mL, about 50 mg/mL to about 375 mg/mL, about 50 mg/mL to about 400 mg/mL, about 50 mg/mL to about 425 mg/mL, about 50 mg/mL to about 450 mg/mL, about 50 mg/mL to about 475 mg/mL, about 50 mg/mL to about 500 mg/mL, about 100 mg/mL to about 150 mg/mL, about 100 mg/mL to about 200 mg/mL, about 100 mg/mL to about 250 mg/mL, about 100 mg/mL to about 300 mg/mL, about 100 mg/mL to about 350 mg/mL, about 100 mg/mL to about 400 mg/mL, about 100 mg/mL to about 450 mg/mL, about 100 mg/mL to about 500 mg/mL, about 200 mg/mL to about 300 mg/mL, about 200 mg/mL to about 400 mg/mL, about 200 mg/mL to about 500 mg/mL, about 200 mg/mL to about 600 mg/mL, about 200 mg/mL to about 700 mg/mL, about 200 mg/mL to about 800 mg/mL, about 200 mg/mL to about 900 mg/mL, or about 200 mg/mL to about 1000 mg/mL.

A therapeutic compound disclosed herein may be a neuropathic pain agent. As used herein, the term "neuropathic pain agent" refers to a class of therapeutic compounds with analgestic, antidepressant, anti-convulsant, anti-epileptic, and/or antispasmodic properties. Neuropathic pain agents are typically, neurotransmitter inhibitors and/or ion channel inhibitors. Examples of suitable neuropathic pain agents include, without limitation, Acetazolamide, Amitriptyline, Amitriptylinoxide, Baclofen, Butriptyline, Carbamazepine, Carisoprodol, Clobazam, Clomipramine, Conotoxins, Cyclobenzaprine, Demexiptiline, Desipramine, Diazepam, Dibenzepin, Dimetacrine, Doxepin, Duloexetine, Ethotoin, Felbamate, Fosphenyloin, Gabapentin, Imipramine, Imipraminoxide, Ketamine, Lamotrigine, Lidocaine, Lignocaine, Lofepramine, Mephenyloin, Melitracen, Metapramine, Metaxalone, Methadone, Methocarbamol, Nitroxazepine, Nortriptyline, Noxiptiline, Oxcarbazepine, Phenobarbital, Phensuximide, Phenyloin, Pipofezine, Pregabalin, Progabide, Propizepine, Protriptyline, Quinupramine, Stiripentol, Tiagabine, Topiramate, Trimethadione, Valproate, Venlafaxine, Vigabatrin, and Zonisamide.

A neuropathic pain agent may be in an amount suitable for its intended use. In aspects of this embodiment, a pharmaceutical composition comprises a neuropathic pain agent in an amount of, e.g., about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 14 mg/mL, about 15 mg/mL, about 16 mg/mL, about 17 mg/mL, about 18 mg/mL, about 19 mg/mL, about 20 mg/mL, about 21 mg/mL, about 22 mg/mL, about 23 mg/mL, about 24 mg/mL, about 25 mg/mL, about 26 mg/mL, about 27 mg/mL, about 28 mg/mL, about 29 mg/mL, or about 30 mg/mL. In other aspects of this embodiment, a pharmaceutical composition comprises a neuropathic pain agent in an amount of, e.g., at least 0.1 mg/mL, at least 0.2 mg/mL, at least 0.3 mg/mL, at least 0.4 mg/mL, at least 0.5 mg/mL, at least 0.6 mg/mL, at least 0.7 mg/mL, at least 0.8 mg/mL, at least 0.9 mg/mL, at least 1 mg/mL, at least 2 mg/mL, at least 3 mg/mL, at least 4 mg/mL, at least 5 mg/mL, at least 6 mg/mL, at least 7 mg/mL, at least 8 mg/mL, at least 9 mg/mL, at least 10 mg/mL, at least 11 mg/mL, at least 12 mg/mL, at least 13 mg/mL, at least 14 mg/mL, at least 15 mg/mL, at least 16 mg/mL, at least 17 mg/mL, at least 18 mg/mL, at least 19 mg/mL, at least 20 mg/mL, at least 21 mg/mL, at least 22 mg/mL, at least 23 mg/mL, at least 24 mg/mL, at least 25 mg/mL, at least 26 mg/mL, at least 27 mg/mL, at least 28 mg/mL, at least 29 mg/mL, or at least 30 mg/mL. In yet other aspects of this embodiment, a pharmaceutical composition comprises a neuropathic pain agent in an amount of, e.g., at most 0.1 mg/mL, at most 0.2 mg/mL, at most 0.3 mg/mL, at most 0.4 mg/mL, at most 0.5 mg/mL, at most 0.6 mg/mL, at most 0.7 mg/mL, at most 0.8 mg/mL, at most 0.9 mg/mL, at most 1 mg/mL, at most 2 mg/mL, at most 3 mg/mL, at most 4 mg/mL, at most 5 mg/mL, at most 6 mg/mL, at most 7 mg/mL, at most 8 mg/mL, at most 9 mg/mL, at most 10 mg/mL, at most 11 mg/mL, at most 12 mg/mL, at most 13 mg/mL, at most 14 mg/mL, at most 15 mg/mL, at most 16 mg/mL, at most 17 mg/mL, at most 18 mg/mL, at most 19 mg/mL, at most 20 mg/mL, at most 21 mg/mL, at most 22 mg/mL, at most 23 mg/mL, at most 24 mg/mL, at most 25 mg/mL, at most 26 mg/mL, at most 27 mg/mL, at most 28 mg/mL, at most 29 mg/mL, or at most 30 mg/mL In yet other aspects of this embodiment, a pharmaceutical composition comprises a neuropathic pain agent in an amount of, e.g., about 0.1 mg/mL to about 1 mg/mL, about 0.1 mg/mL to about 2 mg/mL, about 0.1 mg/mL to about 3 mg/mL, about 0.1 mg/mL to about 4 mg/mL, about 0.1 mg/mL to about 5 mg/mL, about 0.1 mg/mL to about 6 mg/mL, about 0.1 mg/mL to about 7 mg/mL, about 0.1 mg/mL to about 8 mg/mL, about 0.1 mg/mL to about 9 mg/mL, about 0.1 mg/mL to about 10 mg/mL, about 0.25 mg/mL to about 1 mg/mL, about 0.25 mg/mL to about 2 mg/mL, about 0.25 mg/mL to about 3 mg/mL, about 0.25 mg/mL to about 4 mg/mL, about 0.25 mg/mL to about 5 mg/mL, about 0.25 mg/mL to about 6 mg/mL, about 0.25 mg/mL to about 7 mg/mL, about 0.25 mg/mL to about 7.5 mg/mL, about 0.25 mg/mL to about 8 mg/mL, about 0.25 mg/mL to about 9 mg/mL, about 0.25 mg/mL to about 10 mg/mL, about 0.5 mg/mL to about 1 mg/mL, about 0.5 mg/mL to about 2 mg/mL, about 0.5 mg/mL to about 3 mg/mL, about 0.5 mg/mL to about 4 mg/mL, about 0.5 mg/mL to about 5 mg/mL, about 0.5 mg/mL to about 6 mg/mL, about 0.5 mg/mL to about 7 mg/mL, about 0.5 mg/mL to about 8 mg/mL, about 0.5 mg/mL to about 9 mg/mL, about 0.5 mg/mL to about 10 mg/mL, about 0.75 mg/mL to about 1 mg/mL, about 0.75 mg/mL to about 2 mg/mL, about 0.75 mg/mL to about 3 mg/mL, about 0.75 mg/mL to about 4 mg/mL, about 0.75 mg/mL to about 5 mg/mL, about 0.75 mg/mL to about 6 mg/mL, about 0.75 mg/mL to about 7 mg/mL, about 0.75 mg/mL to about 8 mg/mL, about 0.75 mg/mL to about 9 mg/mL, about 0.75 mg/mL to about 10 mg/mL, about 1 mg/mL to about 5 mg/mL, about 1 mg/mL to about 10 mg/mL, about 1 mg/mL to about 15 mg/mL, about 1 mg/mL to about 20 mg/mL, about 1 mg/mL to about 25 mg/mL, about 1 mg/mL to about 30 mg/mL, about 5 mg/mL to about 10 mg/mL, about 5 mg/mL to about 15 mg/mL, about 5 mg/mL to about 20 mg/mL, about 5 mg/mL to about 25 mg/mL, about 5 mg/mL to about 30 mg/mL, about 10 mg/mL to about 20 mg/mL, or about 10 mg/mL to about 30 mg/mL.

A therapeutic compound disclosed herein may be a terpene. As used herein, the term "terpene" refers to a class of therapeutic compounds with analgestic, anti-convulsant, and/or antispasmodic properties. Terpenes appear to function, in part, as a TripM8 calcium channel blocker involved in neurological signaling. A terpene is typically in the form of an oil. Examples of suitable terpenes include, without limitation, camphor oil, citronella, clove oil, eucalyptus oil, ginger oil, horsemint oil, l-menthol, lemon oil, limonene, marjoram oil, mint oil, neroli oil, peppermint oil, pine oil, rose oil, rosemary oil, spearmint oil, tea tree oil, thyme oil, and water mint oil.

A terpene may be in an amount suitable for its intended use. In aspects of this embodiment, a pharmaceutical composition comprises a terpene in an amount of, e.g., about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 14 mg/mL, about 15 mg/mL, about 16 mg/mL, about 17 mg/mL, about 18 mg/mL, about 19 mg/mL, about 20 mg/mL, about 21 mg/mL, about 22 mg/mL, about 23 mg/mL, about 24 mg/mL, about 25 mg/mL, about 26 mg/mL, about 27 mg/mL, about 28 mg/mL, about 29 mg/mL, or about 30 mg/mL. In other aspects of this embodiment, a pharmaceutical composition comprises a terpene in an amount of, e.g., at least 0.1 mg/mL, at least 0.2 mg/mL, at least 0.3 mg/mL, at least 0.4 mg/mL, at least 0.5 mg/mL, at least 0.6 mg/mL, at least 0.7 mg/mL, at least 0.8 mg/mL, at least 0.9 mg/mL, at least 1 mg/mL, at least 2 mg/mL, at least 3 mg/mL, at least 4 mg/mL, at least 5 mg/mL, at least 6 mg/mL, at least 7 mg/mL, at least 8 mg/mL, at least 9 mg/mL, at least 10 mg/mL, at least 11 mg/mL, at least 12 mg/mL, at least 13 mg/mL, at least 14 mg/mL, at least 15 mg/mL, at least 16 mg/mL, at least 17 mg/mL, at least 18 mg/mL, at least 19 mg/mL, at least 20 mg/mL, at least 21 mg/mL, at least 22 mg/mL, at least 23 mg/mL, at least 24 mg/mL, at least 25 mg/mL, at least 26 mg/mL, at least 27 mg/mL, at least 28 mg/mL, at least 29 mg/mL, or at least 30 mg/mL. In yet other aspects of this embodiment, a pharmaceutical composition comprises a terpene in an amount of, e.g., at most 0.1 mg/mL, at most 0.2 mg/mL, at most 0.3 mg/mL, at most 0.4 mg/mL, at most 0.5 mg/mL, at most 0.6 mg/mL, at most 0.7 mg/mL, at most 0.8 mg/mL, at most 0.9 mg/mL, at most 1 mg/mL, at most 2 mg/mL, at most 3 mg/mL, at most 4 mg/mL, at most 5 mg/mL, at most 6 mg/mL, at most 7 mg/mL, at most 8 mg/mL, at most 9 mg/mL, at most 10 mg/mL, at most 11 mg/mL, at most 12 mg/mL, at most 13 mg/mL, at most 14 mg/mL, at most 15 mg/mL, at most 16 mg/mL, at most 17 mg/mL, at most 18 mg/mL, at most 19 mg/mL, at most 20 mg/mL, at most 21 mg/mL, at most 22 mg/mL, at most 23 mg/mL, at most 24 mg/mL, at most 25 mg/mL, at most 26 mg/mL, at most 27 mg/mL, at most 28 mg/mL, at most 29 mg/mL, or at most 30 mg/mL In yet other aspects of this embodiment, a pharmaceutical composition comprises a terpene in an amount of, e.g., about 0.1 mg/mL to about 1 mg/mL, about 0.1 mg/mL to about 2 mg/mL, about 0.1 mg/mL to about 3 mg/mL, about 0.1 mg/mL to about 4 mg/mL, about 0.1 mg/mL to about 5 mg/mL, about 0.1 mg/mL to about 6 mg/mL, about 0.1 mg/mL to about 7 mg/mL, about 0.1 mg/mL to about 8 mg/mL, about 0.1 mg/mL to about 9 mg/mL, about 0.1 mg/mL to about 10 mg/mL, about 0.25 mg/mL to about 1 mg/mL, about 0.25 mg/mL to about 2 mg/mL, about 0.25 mg/mL to about 3 mg/mL, about 0.25 mg/mL to about 4 mg/mL, about 0.25 mg/mL to about 5 mg/mL, about 0.25 mg/mL to about 6 mg/mL, about 0.25 mg/mL to about 7 mg/mL, about 0.25 mg/mL to about 7.5 mg/mL, about 0.25 mg/mL to about 8 mg/mL, about 0.25 mg/mL to about 9 mg/mL, about 0.25 mg/mL to about 10 mg/mL, about 0.5 mg/mL to about 1 mg/mL, about 0.5 mg/mL to about 2 mg/mL, about 0.5 mg/mL to about 3 mg/mL, about 0.5 mg/mL to about 4 mg/mL, about 0.5 mg/mL to about 5 mg/mL, about 0.5 mg/mL to about 6 mg/mL, about 0.5 mg/mL to about 7 mg/mL, about 0.5 mg/mL to about 8 mg/mL, about 0.5 mg/mL to about 9 mg/mL, about 0.5 mg/mL to about 10 mg/mL, about 0.75 mg/mL to about 1 mg/mL, about 0.75 mg/mL to about 2 mg/mL, about 0.75 mg/mL to about 3 mg/mL, about 0.75 mg/mL to about 4 mg/mL, about 0.75 mg/mL to about 5 mg/mL, about 0.75 mg/mL to about 6 mg/mL, about 0.75 mg/mL to about 7 mg/mL, about 0.75 mg/mL to about 8 mg/mL, about 0.75 mg/mL to about 9 mg/mL, about 0.75 mg/mL to about 10 mg/mL, about 1 mg/mL to about 5 mg/mL, about 1 mg/mL to about 10 mg/mL, about 1 mg/mL to about 15 mg/mL, about 1 mg/mL to about 20 mg/mL, about 1 mg/mL to about 25 mg/mL, about 1 mg/mL to about 30 mg/mL, about 5 mg/mL to about 10 mg/mL, about 5 mg/mL to about 15 mg/mL, about 5 mg/mL to about 20 mg/mL, about 5 mg/mL to about 25 mg/mL, about 5 mg/mL to about 30 mg/mL, about 10 mg/mL to about 20 mg/mL, or about 10 mg/mL to about 30 mg/mL.

A therapeutic compound disclosed herein may be an ACE inhibitor. ACE inhibitors reduce the activity of the renin-angiotensin-aldosterone system and are used primarily to treat hypertension, diabetic nephropathy, and congestive heart failure. However, one common side-effect of ACE inhibitors is coughing. Thus, administration of a methylxanthine in conjunction with an ACE inhibitor would be a proactive measure to reduce or prevent the onset of a coughing side-effect produced by the ACE inhibitor. Examples of suitable ACE inhibitors include, without limitation, Captopril, Enalapril, Lisinopril, Meleate, and Ramipril.

An ACE inhibitor may be in an amount suitable for its intended use. In aspects of this embodiment, a pharmaceutical composition comprises an ACE inhibitor in an amount of, e.g., about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 14 mg/mL, about 15 mg/mL, about 16 mg/mL, about 17 mg/mL, about 18 mg/mL, about 19 mg/mL, about 20 mg/mL, about 21 mg/mL, about 22 mg/mL, about 23 mg/mL, about 24 mg/mL, about 25 mg/mL, about 26 mg/mL, about 27 mg/mL, about 28 mg/mL, about 29 mg/mL, or about 30 mg/mL. In other aspects of this embodiment, a pharmaceutical composition comprises an ACE inhibitor in an amount of, e.g., at least 0.1 mg/mL, at least 0.2 mg/mL, at least 0.3 mg/mL, at least 0.4 mg/mL, at least 0.5 mg/mL, at least 0.6 mg/mL, at least 0.7 mg/mL, at least 0.8 mg/mL, at least 0.9 mg/mL, at least 1 mg/mL, at least 2 mg/mL, at least 3 mg/mL, at least 4 mg/mL, at least 5 mg/mL, at least 6 mg/mL, at least 7 mg/mL, at least 8 mg/mL, at least 9 mg/mL, at least 10 mg/mL, at least 11 mg/mL, at least 12 mg/mL, at least 13 mg/mL, at least 14 mg/mL, at least 15 mg/mL, at least 16 mg/mL, at least 17 mg/mL, at least 18 mg/mL, at least 19 mg/mL, at least 20 mg/mL, at least 21 mg/mL, at least 22 mg/mL, at least 23 mg/mL, at least 24 mg/mL, at least 25 mg/mL, at least 26 mg/mL, at least 27 mg/mL, at least 28 mg/mL, at least 29 mg/mL, or at least 30 mg/mL. In yet other aspects of this embodiment, a pharmaceutical composition comprises an ACE inhibitor in an amount of, e.g., at most 0.1 mg/mL, at most 0.2 mg/mL, at most 0.3 mg/mL, at most 0.4 mg/mL, at most 0.5 mg/mL, at most 0.6 mg/mL, at most 0.7 mg/mL, at most 0.8 mg/mL, at most 0.9 mg/mL, at most 1 mg/mL, at most 2 mg/mL, at most 3 mg/mL, at most 4 mg/mL, at most 5 mg/mL, at most 6 mg/mL, at most 7 mg/mL, at most 8 mg/mL, at most 9 mg/mL, at most 10 mg/mL, at most 11 mg/mL, at most 12 mg/mL, at most 13 mg/mL, at most 14 mg/mL, at most 15 mg/mL, at most 16 mg/mL, at most 17 mg/mL, at most 18 mg/mL, at most 19 mg/mL, at most 20 mg/mL, at most 21 mg/mL, at most 22 mg/mL, at most 23 mg/mL, at most 24 mg/mL, at most 25 mg/mL, at most 26 mg/mL, at most 27 mg/mL, at most 28 mg/mL, at most 29 mg/mL, or at most 30 mg/mL In yet other aspects of this embodiment, a pharmaceutical composition comprises an ACE inhibitor in an amount of, e.g., about 0.1 mg/mL to about 1 mg/mL, about 0.1 mg/mL to about 2 mg/mL, about 0.1 mg/mL to about 3 mg/mL, about 0.1 mg/mL to about 4 mg/mL, about 0.1 mg/mL to about 5 mg/mL, about 0.1 mg/mL to about 6 mg/mL, about 0.1 mg/mL to about 7 mg/mL, about 0.1 mg/mL to about 8 mg/mL, about 0.1 mg/mL to about 9 mg/mL, about 0.1 mg/mL to about 10 mg/mL, about 0.25 mg/mL to about 1 mg/mL, about 0.25 mg/mL to about 2 mg/mL, about 0.25 mg/mL to about 3 mg/mL, about 0.25 mg/mL to about 4 mg/mL, about 0.25 mg/mL to about 5 mg/mL, about 0.25 mg/mL to about 6 mg/mL, about 0.25 mg/mL to about 7 mg/mL, about 0.25 mg/mL to about 7.5 mg/mL, about 0.25 mg/mL to about 8 mg/mL, about 0.25 mg/mL to about 9 mg/mL, about 0.25 mg/mL to about 10 mg/mL, about 0.5 mg/mL to about 1 mg/mL, about 0.5 mg/mL to about 2 mg/mL, about 0.5 mg/mL to about 3 mg/mL, about 0.5 mg/mL to about 4 mg/mL, about 0.5 mg/mL to about 5 mg/mL, about 0.5 mg/mL to about 6 mg/mL, about 0.5 mg/mL to about 7 mg/mL, about 0.5 mg/mL to about 8 mg/mL, about 0.5 mg/mL to about 9 mg/mL, about 0.5 mg/mL to about 10 mg/mL, about 0.75 mg/mL to about 1 mg/mL, about 0.75 mg/mL to about 2 mg/mL, about 0.75 mg/mL to about 3 mg/mL, about 0.75 mg/mL to about 4 mg/mL, about 0.75 mg/mL to about 5 mg/mL, about 0.75 mg/mL to about 6 mg/mL, about 0.75 mg/mL to about 7 mg/mL, about 0.75 mg/mL to about 8 mg/mL, about 0.75 mg/mL to about 9 mg/mL, about 0.75 mg/mL to about 10 mg/mL, about 1 mg/mL to about 5 mg/mL, about 1 mg/mL to about 10 mg/mL, about 1 mg/mL to about 15 mg/mL, about 1 mg/mL to about 20 mg/mL, about 1 mg/mL to about 25 mg/mL, about 1 mg/mL to about 30 mg/mL, about 5 mg/mL to about 10 mg/mL, about 5 mg/mL to about 15 mg/mL, about 5 mg/mL to about 20 mg/mL, about 5 mg/mL to about 25 mg/mL, about 5 mg/mL to about 30 mg/mL, about 10 mg/mL to about 20 mg/mL, or about 10 mg/mL to about 30 mg/mL.

A therapeutic compound disclosed herein may be an angiotensin II receptor antagonist. Angiotensin II receptor antagonist modulate the activity of the renin-angiotensin-aldosterone system and are used primarily to treat hypertension, diabetic nephropathy, and congestive heart failure. However, one common side-effect of angiotensin II receptor antagonists is coughing. Thus, administration of a methylxanthine in conjunction with an angiotensin II receptor antagonist would be a proactive measure to reduce or prevent the onset of a coughing side-effect produced by the angiotensin II receptor antagonist. Examples of suitable angiotensin II receptor antagonists include, without limitation, Azilsartan, Candesartan, Eprosartan, Irbesartan, Losartan, Olmesartan, Telmisartan, and Valsartan.

An angiotensin II receptor antagonist may be in an amount suitable for its intended use. In aspects of this embodiment, a pharmaceutical composition comprises an angiotensin II receptor antagonist in an amount of, e.g., about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 14 mg/mL, about 15 mg/mL, about 16 mg/mL, about 17 mg/mL, about 18 mg/mL, about 19 mg/mL, about 20 mg/mL, about 21 mg/mL, about 22 mg/mL, about 23 mg/mL, about 24 mg/mL, about 25 mg/mL, about 26 mg/mL, about 27 mg/mL, about 28 mg/mL, about 29 mg/mL, or about 30 mg/mL. In other aspects of this embodiment, a pharmaceutical composition comprises an angiotensin II receptor antagonist in an amount of, e.g., at least 0.1 mg/mL, at least 0.2 mg/mL, at least 0.3 mg/mL, at least 0.4 mg/mL, at least 0.5 mg/mL, at least 0.6 mg/mL, at least 0.7 mg/mL, at least 0.8 mg/mL, at least 0.9 mg/mL, at least 1 mg/mL, at least 2 mg/mL, at least 3 mg/mL, at least 4 mg/mL, at least 5 mg/mL, at least 6 mg/mL, at least 7 mg/mL, at least 8 mg/mL, at least 9 mg/mL, at least 10 mg/mL, at least 11 mg/mL, at least 12 mg/mL, at least 13 mg/mL, at least 14 mg/mL, at least 15 mg/mL, at least 16 mg/mL, at least 17 mg/mL, at least 18 mg/mL, at least 19 mg/mL, at least 20 mg/mL, at least 21 mg/mL, at least 22 mg/mL, at least 23 mg/mL, at least 24 mg/mL, at least 25 mg/mL, at least 26 mg/mL, at least 27 mg/mL, at least 28 mg/mL, at least 29 mg/mL, or at least 30 mg/mL. In yet other aspects of this embodiment, a pharmaceutical composition comprises an angiotensin II receptor antagonist in an amount of, e.g., at most 0.1 mg/mL, at most 0.2 mg/mL, at most 0.3 mg/mL, at most 0.4 mg/mL, at most 0.5 mg/mL, at most 0.6 mg/mL, at most 0.7 mg/mL, at most 0.8 mg/mL, at most 0.9 mg/mL, at most 1 mg/mL, at most 2 mg/mL, at most 3 mg/mL, at most 4 mg/mL, at most 5 mg/mL, at most 6 mg/mL, at most 7 mg/mL, at most 8 mg/mL, at most 9 mg/mL, at most 10 mg/mL, at most 11 mg/mL, at most 12 mg/mL, at most 13 mg/mL, at most 14 mg/mL, at most 15 mg/mL, at most 16 mg/mL, at most 17 mg/mL, at most 18 mg/mL, at most 19 mg/mL, at most 20 mg/mL, at most 21 mg/mL, at most 22 mg/mL, at most 23 mg/mL, at most 24 mg/mL, at most 25 mg/mL, at most 26 mg/mL, at most 27 mg/mL, at most 28 mg/mL, at most 29 mg/mL, or at most 30 mg/mL In yet other aspects of this embodiment, a pharmaceutical composition comprises an angiotensin II receptor antagonist in an amount of, e.g., about 0.1 mg/mL to about 1 mg/mL, about 0.1 mg/mL to about 2 mg/mL, about 0.1 mg/mL to about 3 mg/mL, about 0.1 mg/mL to about 4 mg/mL, about 0.1 mg/mL to about 5 mg/mL, about 0.1 mg/mL to about 6 mg/mL, about 0.1 mg/mL to about 7 mg/mL, about 0.1 mg/mL to about 8 mg/mL, about 0.1 mg/mL to about 9 mg/mL, about 0.1 mg/mL to about 10 mg/mL, about 0.25 mg/mL to about 1 mg/mL, about 0.25 mg/mL to about 2 mg/mL, about 0.25 mg/mL to about 3 mg/mL, about 0.25 mg/mL to about 4 mg/mL, about 0.25 mg/mL to about 5 mg/mL, about 0.25 mg/mL to about 6 mg/mL, about 0.25 mg/mL to about 7 mg/mL, about 0.25 mg/mL to about 7.5 mg/mL, about 0.25 mg/mL to about 8 mg/mL, about 0.25 mg/mL to about 9 mg/mL, about 0.25 mg/mL to about 10 mg/mL, about 0.5 mg/mL to about 1 mg/mL, about 0.5 mg/mL to about 2 mg/mL, about 0.5 mg/mL to about 3 mg/mL, about 0.5 mg/mL to about 4 mg/mL, about 0.5 mg/mL to about 5 mg/mL, about 0.5 mg/mL to about 6 mg/mL, about 0.5 mg/mL to about 7 mg/mL, about 0.5 mg/mL to about 8 mg/mL, about 0.5 mg/mL to about 9 mg/mL, about 0.5 mg/mL to about 10 mg/mL, about 0.75 mg/mL to about 1 mg/mL, about 0.75 mg/mL to about 2 mg/mL, about 0.75 mg/mL to about 3 mg/mL, about 0.75 mg/mL to about 4 mg/mL, about 0.75 mg/mL to about 5 mg/mL, about 0.75 mg/mL to about 6 mg/mL, about 0.75 mg/mL to about 7 mg/mL, about 0.75 mg/mL to about 8 mg/mL, about 0.75 mg/mL to about 9 mg/mL, about 0.75 mg/mL to about 10 mg/mL, about 1 mg/mL to about 5 mg/mL, about 1 mg/mL to about 10 mg/mL, about 1 mg/mL to about 15 mg/mL, about 1 mg/mL to about 20 mg/mL, about 1 mg/mL to about 25 mg/mL, about 1 mg/mL to about 30 mg/mL, about 5 mg/mL to about 10 mg/mL, about 5 mg/mL to about 15 mg/mL, about 5 mg/mL to about 20 mg/mL, about 5 mg/mL to about 25 mg/mL, about 5 mg/mL to about 30 mg/mL, about 10 mg/mL to about 20 mg/mL, or about 10 mg/mL to about 30 mg/mL.

A pharmaceutical composition disclosed herein may optionally include a pharmaceutically-acceptable carrier that facilitates processing of an active ingredient into pharmaceutically-acceptable compositions. As used herein, the term "pharmacologically-acceptable carrier" is synonymous with "pharmacological carrier" and means any carrier that has substantially no long term or permanent detrimental effect when administered and encompasses terms such as "pharmacologically acceptable vehicle, stabilizer, diluent, additive, auxiliary or excipient." Such a carrier generally is mixed with an active compound or permitted to dilute or enclose the active compound and can be a solid, semi-solid, or liquid agent. It is understood that the active ingredients can be soluble or can be delivered as a suspension in the desired carrier or diluent. Any of a variety of pharmaceutically acceptable carriers can be used including, without limitation, aqueous media such as, e.g., water, saline, glycine, hyaluronic acid and the like; solid carriers such as, e.g., mannitol, lactose, starch, magnesium stearate, sodium saccharin, talcum, cellulose, glucose, sucrose, magnesium carbonate, and the like; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active ingredient, its use in pharmaceutically acceptable compositions is contemplated. Non-limiting examples of specific uses of such pharmaceutical carriers can be found in Pharmaceutical Dosage Forms and Drug Delivery Systems (Howard C. Ansel et al., eds., Lippincott Williams & Wilkins Publishers, 7th ed. 1999); REMINGTON: THE SCIENCE AND PRACTICE OF PHARMACY (Alfonso R. Gennaro ed., Lippincott, Williams & Wilkins, 20th ed. 2000); Goodman & Gilman's The Pharmacological Basis of Therapeutics (Joel G. Hardman et al., eds., McGraw-Hill Professional, 10th ed. 2001); and Handbook of Pharmaceutical Excipients (Raymond C. Rowe et al., APhA Publications, 4th edition 2003). These protocols are routine procedures and any modifications are well within the scope of one skilled in the art and from the teaching herein.

A pharmaceutical composition disclosed herein can optionally include, without limitation, other pharmaceutically acceptable components (or pharmaceutical components), including, without limitation, buffers, preservatives, tonicity adjusters, salts, antioxidants, osmolality adjusting agents, physiological substances, pharmacological substances, bulking agents, emulsifying agents, wetting agents, flavoring agents, coloring agents, and the like. Various buffers and means for adjusting pH can be used to prepare a pharmaceutical composition disclosed herein, provided that the resulting preparation is pharmaceutically acceptable. Such buffers include, without limitation, acetate buffers, citrate buffers, phosphate buffers, neutral buffered saline, phosphate buffered saline and borate buffers. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole and butylated hydroxytoluene. Useful preservatives include, without limitation, benzalkonium chloride, chlorobutanol, thimerosal, phenylmercuric acetate, phenylmercuric nitrate, a stabilized oxy chloro composition and chelants, such as, e.g., DTPA or DTPA-bisamide, calcium DTPA, and CaNaDTPA-bisamide. Tonicity adjustors useful in a pharmaceutical composition include, without limitation, salts such as, e.g., sodium chloride, potassium chloride, mannitol or glycerin and other pharmaceutically acceptable tonicity adjustor. The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. It is understood that these and other substances known in the art of pharmacology can be included in a pharmaceutical composition.

A therapeutic compound disclosed herein, or a composition comprising such a therapeutic compound, may be formulated for either local or systemic delivery using topical, enteral or parenteral routes of administration. Additionally, a therapeutic compound disclosed herein may be formulated by itself in a pharmaceutical composition, or may be formulated together with one or more other therapeutic compounds disclosed herein in a single pharmaceutical composition.

A therapeutic compound disclosed herein, or a composition comprising such a therapeutic compound, may be made into an inhaled formulation. Inhaled formulations suitable for enteral or parenteral administration include, without limitation, aerosols, dry powders. A therapeutic compound or composition disclosed herein intended for such administration may be prepared according to any method known to the art for the manufacture of pharmaceutical compositions.

In such inhaled dosage forms, the therapeutic compound may be prepared for delivery as an aerosol in a liquid propellant for use in a pressurised (PDI) or other metered dose inhaler (MDI). Propellants suitable for use in a PDI or MDI include, without limitation, CFC-12, HFA-134a, HFA- 227, HCFC-22 (difluorochloromethane), HFA-152 (difluoroethane and isobutane). A therapeutic compound may also be delivered using a nebulisers or other aerosol delivery system. A therapeutic compound may be prepared for delivery as a dry powder for use in a dry powder inhaler (DPI). A dry powder for use in the inhalers will usually have a mass median aerodynamic diameter of less than 30 pm, preferably less than 20 pm and more preferably less than 10 pm. Microparticles having aerodynamic diameters in the range of about 5 pm to about 0.5 pm will generally be deposited in the respiratory bronchioles, whereas smaller particles, having aerodynamic diameters in the range of about 2 pm to about 0.05 pm, are likely to be deposited in the alveoli. A DPI may be a passive delivery mechanism, which relies on the individual's inspiration to introduce the particles into the lungs, or an active delivery mechanism, requiring a mechanism for delivering the powder to the individual. As disclosed herein, an equivalent antitussive effect for inhaled methylxanthine requires only one-third the dose of the same methylxanthine administered orally. In inhalatory formulations, a therapeutically effective amount of a therapeutic compound disclosed herein for an inhaled formulation may be between about 0.0001% (w/v) to about 60% (w/v), about 0.001% (w/v) to about 40.0% (w/v), or about 0.01% (w/v) to about 20.0% (w/v). In inhalatory formulations, a therapeutically effective amount of a therapeutic compound disclosed herein for an inhaled formulation may also be between about 0.0001% (w/w) to about 60% (w/w), about 0.001% (w/w) to about 40.0% (w/w), or about 0.01% (w/w) to about 20.0% (w/w).

A therapeutic compound disclosed herein, or a composition comprising such a therapeutic compound, may be made into a solid formulation. Solid formulations suitable for enteral or parenteral administration include, without limitation, capsules, tablets, pills, troches, lozenges, powders and granules suitable for inhalation or for reconstitution into sterile injectable solutions or dispersions. A therapeutic compound or composition disclosed herein intended for such administration may be prepared according to any method known to the art for the manufacture of pharmaceutical compositions. In such solid dosage forms, the therapeutic compound may be admixed with (a) at least one inert customary excipient (or carrier), such as, e.g., sodium citrate or dicalcium phosphate or (b) fillers or extenders, as for example, starch, lactose, sucrose, glucose, mannitol, isomalt, and silicic acid, (c) binders, such as, e.g., carboxymethylcellulose, alignates, gelatin, polyvinylpyrrolidone, sucrose and acacia, (d) humectants, such as, e.g., glycerol, (e) disintegrating agents, such as, e.g., agar-agar, calcium carbonate, corn starch, potato starch, tapioca starch, alginic acid, certain complex silicates and sodium carbonate, (f) solution retarders, such as, e.g., paraffin, (g) absorption accelerators, such as, e.g., quaternary ammonium compounds, (h) wetting agents, such as, e.g., cetyl alcohol and glycerol monostearate, (i) adsorbents, such as, e.g., kaolin and bentonite, (j) lubricants, such as, e.g., talc, stearic acid, calcium stearate, magnesium stearate, solid polyethylene glycols, sodium lauryl sulfate or mixtures thereof, and (k) buffering agents. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. In solid formulations, a therapeutically effective amount of a therapeutic compound disclosed herein typically may be between about 0.0001% (w/w) to about 60% (w/w), about 0.001% (w/w) to about 40.0% (w/w), or about 0.01% (w/w) to about 20.0% (w/w).

A therapeutic compound disclosed herein, or a composition comprising such a therapeutic compound, may be made into a semi-solid formulation. Semi-solid formulations suitable for topical administration include, without limitation, ointments, creams, salves, and gels. A therapeutic compound or composition disclosed herein intended for such administration may be prepared according to any method known to the art for the manufacture of pharmaceutical compositions. In semi-solid formulations, a therapeutically effective amount of a therapeutic compound disclosed herein typically may be between about 0.0001% (w/v) to about 60% (w/v), about 0.001% (w/v) to about 40.0% (w/v), or about 0.01% (w/v) to about 20.0% (w/v). In semi-solid formulations, a therapeutically effective amount of a therapeutic compound disclosed herein typically may also be between about 0.0001% (w/w) to about 60% (w/w), about 0.001% (w/w) to about 40.0% (w/w), or about 0.01% (w/w) to about 20.0% (w/w).

A therapeutic compound disclosed herein, or a composition comprising such a therapeutic compound, may be made into a liquid formulation. Liquid formulations suitable for enteral or parenteral administration include, without limitation, solutions, syrups, elixirs, dispersions, emulsions, and suspensions. A therapeutic compound or composition disclosed herein intended for such administration may be prepared according to any method known to the art for the manufacture of pharmaceutical compositions. In such liquid dosage forms, a therapeutic compound or composition disclosed herein may be admixed with (a) suitable aqueous and nonaqueous carriers, (b) diluents, (c) solvents, such as, e.g., water, ethanol, propylene glycol, polyethyleneglycol, glycerol, vegetable oils, such as, e.g., rapeseed oil and olive oil, and injectable organic esters such as ethyl oleate; and/or fluidity agents, such as, e.g., surfactants or coating agents like lecithin. In the case of dispersions and suspensions, fluidity can also be controlled by maintaining a particular particle size. In liquid formulations, a therapeutically effective amount of a therapeutic compound disclosed herein typically may be between about 0.0001% (w/v) to about 60% (w/v), about 0.001% (w/v) to about 40.0% (w/v), or about 0.01% (w/v) to about 20.0% (w/v).

Syrups and elixirs may be formulated with sweetening agents, for example glycerol, propylene glycol, sorbitol or sucrose. Such formulations may also contain a demulcent, a preservative, flavoring agents, and coloring agents.

Liquid suspensions may be formulated by suspending a therapeutic compound disclosed herein in admixture with excipients suitable for the manufacture of aqueous suspensions. Such excipients are suspending agents, for example sodium carboxymethylcellulose, methylcellulose, hydroxypropylmethylcellulose, sodium alginate, pectin, polyvinyl pyrrolidone, polyvinyl alcohol, natural gum, agar, gum tragacanth and gum acacia; dispersing or wetting agents may be a naturally occurring phosphatide, for example lecithin, or condensation products of an alkylene oxide with fatty acids, for example polyoxyethylene stearate, or condensation products of ethylene oxide with long-chain aliphatic alcohols, for example heptadecaethyleneoxycetanol, or condensation products of ethylene oxide with partial esters derived from fatty acids, for example polyoxyethylene sorbitan monooleate.

Oily suspensions may be formulated by suspending a therapeutic compound disclosed herein in admixture with (a) vegetable oils, such as, e.g., almond oil, arachis oil, avocado oil, canola oil, castor oil, coconut oil, corn oil, cottonseed oil, grape seed oil, hazelnut oil, hemp oil, linseed oil, olive oil, palm oil, peanut oil, rapeseed oil, rice bran oil, safflower oil, sesame oil, soybean oil, soya oil, sunflower oil, walnut oil, wheat germ oil, or a combination thereof, (b) a saturated fatty acid, an unsaturated fatty acid, or a combination thereof, such as, e.g., palmitic acid, stearic acid, oleic acid, linoleic acid, linolenic acid, or a combination thereof, (c) mineral oil such as, e.g., liquid paraffin, (d) surfactants or detergents. The oily suspensions may contain a thickening agent, for example beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the combined therapeutic compounds in admixture with a dispersing or wetting agent, suspending agent and one or more preservatives.

A therapeutic compound disclosed herein may be in the form of oil-in-water emulsions. The oily phase may be a vegetable oil as disclosed herein or a mineral oil as disclosed herein or mixtures thereof. Suitable emulsifying agents may be naturally occurring gums, such as, e.g., gum acacia or gum tragacanth, naturally occurring phosphatides, for example soya bean, lecithin, and esters or partial esters derived from fatty acids and hexitol anhydrides, for example sorbitan monooleate and condensation products of the said partial esters with ethylene oxide, for example polyoxyethylene sorbitan monooleate.

A therapeutic compound disclosed herein, or a composition comprising such a therapeutic compound, may also be incorporated into a drug delivery platform in order to achieve a controlled release profile over time. Such a drug delivery platform comprises a therapeutic compound disclosed herein dispersed within a polymer matrix, typically a biodegradable, bioerodible, and/or bioresorbable polymer matrix. As used herein, the term "polymer" refers to synthetic homo- or copolymers, naturally occurring homo- or copolymers, as well as synthetic modifications or derivatives thereof having a linear, branched or star structure. Copolymers can be arranged in any form, such as, e.g., random, block, segmented, tapered blocks, graft, or triblock. Polymers are generally condensation polymers. Polymers can be further modified to enhance their mechanical or degradation properties by introducing cross-linking agents or changing the hydrophobicity of the side residues. If crosslinked, polymers are usually less than 5% crosslinked, usually less than 1% crosslinked.

Suitable polymers include, without limitation, alginates, aliphatic polyesters, polyalkylene oxalates, polyamides, polyamidoesters, polyanhydrides, polycarbonates, polyesters, polyethylene glycol, polyhydroxyaliphatic carboxylic acids, polyorthoesters, polyoxaesters, polypeptides, polyphosphazenes, polysaccharides, and polyurethanes. The polymer usually comprises at least about 10% (w/w), at least about 20% (w/w), at least about 30% (w/w), at least about 40% (w/w), at least about 50% (w/w), at least about 60% (w/w), at least about 70% (w/w), at least about 80% (w/w), or at least about 90% (w/w) of the drug delivery platform. Examples of biodegradable, bioerodible, and/or bioresorbable polymers and methods useful to make a drug delivery platform are described in, e.g., Drost, et. al., Controlled Release Formulation, U.S. Pat. No. 4,756,911; Smith, et. al., Sustained Release Drug Delivery Devices, U.S. Pat. No. 5,378,475; Wong and Kochinke, Formulation for Controlled Release of Drugs by Combining Hyrophilic and Hydrophobic Agents, U.S. Pat. No. 7,048,946; Hughes, et. al., Compositions and Methods for Localized Therapy of the Eye, U.S. Patent Publication 2005/0181017; Hughes, Hypotensive Lipid-Containing Biodegradable Intraocular Implants and Related Methods, U.S. Patent Publication 2005/0244464; Altman, et al., Silk Fibroin Hydrogels and Uses Thereof, U.S. Patent Publication 2011/0008437; each of which is incorporated by reference in its entirety.

In aspects of this embodiment, a polymer composing the matrix is a polypeptide such as, e.g., silk fibroin, keratin, or collagen. In other aspects of this embodiment, a polymer composing the matrix is a polysaccharide such as, e.g., cellulose, agarose, elastin, chitosan, chitin, or a glycosaminoglycan like chondroitin sulfate, dermatan sulfate, keratan sulfate, or hyaluronic acid. In yet other aspects of this embodiment, a polymer composing the matrix is a polyester such as, e.g., D-lactic acid, L-lactic acid, racemic lactic acid, glycolic acid, caprolactone, and combinations thereof.

One of ordinary skill in the art appreciates that the selection of a suitable polymer for forming a suitable disclosed drug delivery platform depends on several factors. The more relevant factors in the selection of the appropriate polymer(s), include, without limitation, compatibility of polymer with drug, desired release kinetics of drug, desired biodegradation kinetics of platform at implantation site, desired bioerodible kinetics of platform at implantation site, desired bioresorbable kinetics of platform at implantation site, in vivo mechanical performance of platform, processing temperatures, biocompatibility of platform, and patient tolerance. Other relevant factors that, to some extent, dictate the in vitro and in vivo behavior of the polymer include the chemical composition, spatial distribution of the constituents, the molecular weight of the polymer and the degree of crystallinity.

A drug delivery platform includes both a sustained release drug delivery platform and an extended release drug delivery platform. As used herein, the term "sustained release" refers to the release of a therapeutic compound disclosed herein over a period of about seven days or more. As used herein, the term "extended release" refers to the release of a therapeutic compound disclosed herein over a period of time of less than about seven days.

In aspects of this embodiment, a sustained release drug delivery platform releases a therapeutic compound disclosed herein with substantially zero order release kinetics over a period of, e.g., about 7 days after administration, about 15 days after administration, about 30 days after administration, about 45 days after administration, about 60 days after administration, about 75 days after administration, or about 90 days after administration. In other aspects of this embodiment, a sustained release drug delivery platform releases a therapeutic compound disclosed herein with substantially zero order release kinetics over a period of, e.g., at least 7 days after administration, at least 15 days after administration, at least 30 days after administration, at least 45 days after administration, at least 60 days after administration, at least 75 days after administration, or at least 90 days after administration.

In aspects of this embodiment, a sustained release drug delivery platform releases a therapeutic compound disclosed herein with substantially first order release kinetics over a period of, e.g., about 7 days after administration, about 15 days after administration, about 30 days after administration, about 45 days after administration, about 60 days after administration, about 75 days after administration, or about 90 days after administration. In other aspects of this embodiment, a sustained release drug delivery platform releases a therapeutic compound disclosed herein with substantially first order release kinetics over a period of, e.g., at least 7 days after administration, at least 15 days after administration, at least 30 days after administration, at least 45 days after administration, at least 60 days after administration, at least 75 days after administration, or at least 90 days after administration.

In aspects of this embodiment, a drug delivery platform releases a therapeutic compound disclosed herein with substantially zero order release kinetics over a period of, e.g., about 1 day after administration, about 2 days after administration, about 3 days after administration, about 4 days after administration, about 5 days after administration, or about 6 days after administration. In other aspects of this embodiment, a drug delivery platform releases a therapeutic compound disclosed herein with substantially zero order release kinetics over a period of, e.g., at most 1 day after administration, at most 2 days after administration, at most 3 days after administration, at most 4 days after administration, at most 5 days after administration, or at most 6 days after administration.

In aspects of this embodiment, a drug delivery platform releases a therapeutic compound disclosed herein with substantially first order release kinetics over a period of, e.g., about 1 day after administration, about 2 days after administration, about 3 days after administration, about 4 days after administration, about 5 days after administration, or about 6 days after administration. In other aspects of this embodiment, a drug delivery platform releases a therapeutic compound disclosed herein with substantially first order release kinetics over a period of, e.g., at most 1 day after administration, at most 2 days after administration, at most 3 days after administration, at most 4 days after administration, at most 5 days after administration, or at most 6 days after administration.

Aspects of the present specification disclose, in part, a method of treating an individual with a coughing condition. In one embodiment, the method comprises the step of administering to an individual in need thereof a pharmaceutical composition disclosed herein, wherein administration reduces a symptom associated with the coughing condition, thereby treating the individual.

A coughing condition refers to a vagal nerve-based disorder where an individual has a sudden reflex (the cough reflex), which may occur repetitively, physiologically designed to clear the large breathing passages from any of various irritants, particles, microbes or other organisms, secretions, etc., and which is usually accompanied by a distinctive sound. A cough comprises an inhalation, a forced exhalation against a closed glottis, and a release of air from the lungs which immediately follows opening of the glottis. The cough reflex is initiated by stimulating two types of afferent nerves, the myelinated rapidly adapting receptors and the nonmyelinated C-fibers with endings in the lungs.

A cough can be classified by its duration, character, quality, and timing. For example, a cough may be classified as an acute cough, a subacute cough, or a chronic cough. An acute cough is one where there is a sudden onset of a cough and such coughing is present in an individual for three weeks or less. A subacute cough is one where the coughing is present in an individual for between about three weeks to about eight weeks. A chronic cough is one where the coughing is present in an individual for about eight weeks or more.

A cough may also be classified as a non-productive (dry) cough or a productive cough. A non-productive cough is one where no phlegm or sputum is expelled from the respiratory system during a cough. A productive cough is one where no phlegm or sputum is expelled from the respiratory system during a cough. A cough may also be classified based on occurrence such as when occurring only at night, occurring during both night and day, or occurring during the day only.

A cough can initially be brought on by many factors, including without limitation, asthma; bronchitis; aspiration or choking; gastroesophageal reflux disease (GERD); infection of the respiratory tract by bacteria, viruses, or other parasites; inflammation; some medications, such as, e.g., ACE inhibitors; pollution; post-nasal drip; smoking; vagal nerve irritation; diseases of the external auditory canal; lung disease, such as bronchiectasis, cystic fibrosis, interstitial lung disease and sarcoidosis; tumors or other cancer in the lungs; habit (habit cough); a tic or other disorders such as Tourette syndrome (tic cough); and, cardiovascular diseases such as heart failure, pulmonary infarction and aortic aneurysm.

Where a cough is the result of an infection of the respiratory tract, some such infections include without limitation a cold, croup, pertussis, pneumonia, and tuberculosis. Asthma is a common cause of chronic cough. Where a cough is the only symptom of the asthma (besides bronchial hyperresponsiveness and reversibility), the asthma is termed cough-variant asthma. Atopic cough is a cough which occurs in individuals who have a family history of allergic hypersensitivity (atopy) and a high number of eosinophils in the sputum, but normal airway function. A psychogenic cough may arise without a physical initiating factor, potentially due to emotional or psychological issues. A post-infectious cough, as used herein, refers to a cough that persists after the infection or other factor that initially brought on the cough has cleared. A post-infectious cough is typically is a non-productive cough accompanied by a ticklish feeling in the lungs, chest or throat, and can persist for weeks after removal of the initiating factor. The actual cause of the post-infectious cough may be inflammation due to the initiating factor, which in turn produces discomfort or the ticklish feeling, which produces more coughing. Ironically then, the post-infectious cough itself serves as the cause of the cough.

Aspects of the present specification disclose, in part, treating an individual suffering from a coughing condition. As used herein, the term "treating," refers to reducing or eliminating in an individual a clinical symptom of a coughing condition; or delaying or preventing in an individual the onset of a clinical symptom of a coughing condition. For example, the term "treating" can mean reducing a symptom of a condition characterized by a coughing condition by, e.g., at least 20%, at least 25%, at least 30%, at least 35%, at least 40%, at least 45%, at least 50%, at least 55%, at least 60%, at least 65%, at least 70%, at least 75%, at least 80%, at least 85%, at least 90% at least 95%, or at least 100%. As another example, the term "treating" can mean controlling a cough such as, e.g., reducing the number of coughs per given time period and/or the severity of cough. The actual symptoms associated with a coughing condition are well known and can be determined by a person of ordinary skill in the art by taking into account factors, including, without limitation, the location of the coughing condition, the cause of the coughing condition, the severity of the coughing condition, and/or the tissue or organ affected by the coughing condition. Those of skill in the art will know the appropriate symptoms or indicators associated with a specific type of coughing condition and will know how to determine if an individual is a candidate for treatment as disclosed herein.

Coughing condition symptoms include, without limitation, coughing, hoarseness, sore throat, breathing difficulty, respiratory congestion, respiratory constriction, respiratory inflammation, phlegm production, fainting, insomnia, vomiting, subconjunctival hemorrhage (red eye), cough defecation, cough urination, abdominal hernia, pelvic hernia, costochondritis, and lower rib fractures. The actual symptoms associated with a coughing condition are well known and can be determined by a person of ordinary skill in the art by taking into account factors, including, without limitation, the location of the coughing condition, the cause of the coughing condition, the severity of the coughing condition, the tissue or organ affected by the coughing condition.

In one embodiment, a coughing condition comprises an acute coughing condition.

In another embodiment, a coughing condition comprises a subacute coughing condition.

In another embodiment, a coughing condition comprises a chronic coughing condition.

In another embodiment, a coughing condition comprises a non-productive coughing condition.

In another embodiment, a coughing condition comprises a productive coughing condition.

In another embodiment, a coughing condition comprises a cough associated with a disease or disorder. In aspects of this embodiment, the disease or disorder includes an asthma, an atopic cough a bronchitis, a gastroesophageal reflux disease (GERD), an infection of the respiratory tract, an inflammation, a medication, a pollutant, a post-nasal drip, a smoking event, a vagal nerve irritation, a diseases of the external auditory canal, a lung disease, a lung tumor, a habit cough, a tic, a Tourette syndrome, a cardiovascular disease, a post-infectious cough. In an aspect of this embodiment, the lung disease includes, without limitation, a bronchiectasis, a cystic fibrosis, an interstitial lung disease, a sarcoidosis, a COPD. In another aspect of this embodiment, the cardiovascular disease includes, without limitation, a heart failure, a pulmonary infarction and an aortic aneurysm. In yet another aspect of this embodiment, the infection of the respiratory tract includes, without limitation, a cold, croup, pertussis, pneumonia, and tuberculosis.

A composition or compound is administered to an individual. An individual is typically a human being. Typically, any individual who is a candidate for a conventional coughing condition treatment is a candidate for a coughing condition treatment disclosed herein. Pre-operative evaluation typically includes routine history and physical examination in addition to thorough informed consent disclosing all relevant risks and benefits of the procedure.

A pharmaceutical composition disclosed herein may comprise a therapeutic compound in a therapeutically effective amount. As used herein, the term "effective amount" is synonymous with "therapeutically effective amount", "effective dose", or "therapeutically effective dose" and when used in reference to treating a coughing condition refers to the minimum dose of a therapeutic compound disclosed herein necessary to achieve the desired therapeutic effect and includes a dose sufficient to reduce a symptom associated with a coughing condition. The effectiveness of a therapeutic compound disclosed herein in treating a coughing condition can be determined by observing an improvement in an individual based upon one or more clinical symptoms, and/or physiological indicators associated with the coughing condition. An improvement in a coughing condition also can be indicated by a reduced need for a concurrent therapy.

The appropriate effective amount of a therapeutic compound disclosed herein to be administered to an individual for a particular coughing condition can be determined by a person of ordinary skill in the art by taking into account factors, including, without limitation, the type of coughing condition, the location of the coughing condition, the cause of the coughing condition, the severity of the coughing condition, the degree of relief desired, the duration of relief desired, the particular therapeutic compound used, the rate of excretion of the therapeutic compound used, the pharmacodynamics of the therapeutic compound used, the nature of the other compounds to be included in the composition, the particular route of administration, the particular characteristics, history and risk factors of the patient, such as, e.g., age, weight, general health and the like, or any combination thereof. Additionally, where repeated administration of a therapeutic compound is used, an effective amount of a therapeutic compound will further depend upon factors, including, without limitation, the frequency of administration, the half-life of the therapeutic compound, or any combination thereof. In is known by a person of ordinary skill in the art that an effective amount of a therapeutic compound disclosed herein can be extrapolated from in vitro assays and in vivo administration studies using animal models prior to administration to humans.

Wide variations in the necessary effective amount are to be expected in view of the differing efficiencies of the various routes of administration. For instance, oral administration of a therapeutic compound disclosed herein generally would be expected to require higher dosage levels than administration by inhalation. Similarly, systemic administration of a therapeutic compound disclosed herein would be expected to require higher dosage levels than a local administration. Variations in these dosage levels can be adjusted using standard empirical routines of optimization, which are well-known to a person of ordinary skill in the art. The precise therapeutically effective dosage levels and patterns are preferably determined by the attending physician in consideration of the above-identified factors. One skilled in the art will recognize that the condition of the individual can be monitored throughout the course of therapy and that the effective amount of a therapeutic compound disclosed herein that is administered can be adjusted accordingly.

In aspects of this embodiment, a therapeutically effective amount of a therapeutic compound disclosed herein reduces a symptom associated with a coughing condition by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 100%. In other aspects of this embodiment, a therapeutically effective amount of a therapeutic compound disclosed herein reduces a symptom associated with a coughing condition by, e.g., at most 10%, at most 15%, at most 20%, at most 25%, at most 30%, at most 35%, at most 40%, at most 45%, at most 50%, at most 55%, at most 60%, at most 65%, at most 70%, at most 75%, at most 80%, at most 85%, at most 90%, at most 95% or at most 100%. In yet other aspects of this embodiment, a therapeutically effective amount of a therapeutic compound disclosed herein reduces a symptom associated with a coughing condition by, e.g., about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 20%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%.

In other aspects of this embodiment, a therapeutically effective amount of a therapeutic compound disclosed herein generally is in the range of about 0.001 mg/kg/day to about 100 mg/kg/day. In aspects of this embodiment, an effective amount of a therapeutic compound disclosed herein may be, e.g., at least 0.001 mg/kg/day, at least 0.01 mg/kg/day, at least 0.1 mg/kg/day, at least 1.0 mg/kg/day, at least 5.0 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, or at least 50 mg/kg/day. In other aspects of this embodiment, an effective amount of a therapeutic compound disclosed herein may be in the range of, e.g., about 0.001 mg/kg/day to about 10 mg/kg/day, about 0.001 mg/kg/day to about 15 mg/kg/day, about 0.001 mg/kg/day to about 20 mg/kg/day, about 0.001 mg/kg/day to about 25 mg/kg/day, about 0.001 mg/kg/day to about 30 mg/kg/day, about 0.001 mg/kg/day to about 35 mg/kg/day, about 0.001 mg/kg/day to about 40 mg/kg/day, about 0.001 mg/kg/day to about 45 mg/kg/day, about 0.001 mg/kg/day to about 50 mg/kg/day, about 0.001 mg/kg/day to about 75 mg/kg/day, or about 0.001 mg/kg/day to about 100 mg/kg/day. In yet other aspects of this embodiment, an effective amount of a therapeutic compound disclosed herein may be in the range of, e.g., about 0.01 mg/kg/day to about 10 mg/kg/day, about 0.01 mg/kg/day to about 15 mg/kg/day, about 0.01 mg/kg/day to about 20 mg/kg/day, about 0.01 mg/kg/day to about 25 mg/kg/day, about 0.01 mg/kg/day to about 30 mg/kg/day, about 0.01 mg/kg/day to about 35 mg/kg/day, about 0.01 mg/kg/day to about 40 mg/kg/day, about 0.01 mg/kg/day to about 45 mg/kg/day, about 0.01 mg/kg/day to about 50 mg/kg/day, about 0.01 mg/kg/day to about 75 mg/kg/day, or about 0.01 mg/kg/day to about 100 mg/kg/day. In still other aspects of this embodiment, an effective amount of a therapeutic compound disclosed herein may be in the range of, e.g., about 0.1 mg/kg/day to about 10 mg/kg/day, about 0.1 mg/kg/day to about 15 mg/kg/day, about 0.1 mg/kg/day to about 20 mg/kg/day, about 0.1 mg/kg/day to about 25 mg/kg/day, about 0.1 mg/kg/day to about 30 mg/kg/day, about 0.1 mg/kg/day to about 35 mg/kg/day, about 0.1 mg/kg/day to about 40 mg/kg/day, about 0.1 mg/kg/day to about 45 mg/kg/day, about 0.1 mg/kg/day to about 50 mg/kg/day, about 0.1 mg/kg/day to about 75 mg/kg/day, or about 0.1 mg/kg/day to about 100 mg/kg/day.

In other aspects of this embodiment, an effective amount of a therapeutic compound disclosed herein may be in the range of, e.g., about 1 mg/kg/day to about 10 mg/kg/day, about 1 mg/kg/day to about 15 mg/kg/day, about 1 mg/kg/day to about 20 mg/kg/day, about 1 mg/kg/day to about 25 mg/kg/day, about 1 mg/kg/day to about 30 mg/kg/day, about 1 mg/kg/day to about 35 mg/kg/day, about 1 mg/kg/day to about 40 mg/kg/day, about 1 mg/kg/day to about 45 mg/kg/day, about 1 mg/kg/day to about 50 mg/kg/day, about 1 mg/kg/day to about 75 mg/kg/day, or about 1 mg/kg/day to about 100 mg/kg/day. In yet other aspects of this embodiment, an effective amount of a therapeutic compound disclosed herein may be in the range of, e.g., about 5 mg/kg/day to about 10 mg/kg/day, about 5 mg/kg/day to about 15 mg/kg/day, about 5 mg/kg/day to about 20 mg/kg/day, about 5 mg/kg/day to about 25 mg/kg/day, about 5 mg/kg/day to about 30 mg/kg/day, about 5 mg/kg/day to about 35 mg/kg/day, about 5 mg/kg/day to about 40 mg/kg/day, about 5 mg/kg/day to about 45 mg/kg/day, about 5 mg/kg/day to about 50 mg/kg/day, about 5 mg/kg/day to about 75 mg/kg/day, or about 5 mg/kg/day to about 100 mg/kg/day.

In other aspects of this embodiment, a therapeutically effective amount of a therapeutic compound disclosed herein generally is in the range of about 1 mg/day to about 3,000 mg/day. In aspects of this embodiment, an effective amount of a therapeutic compound disclosed herein may be, e.g., at least 40 mg/day, at least 50 mg/day, at least 60 mg/day, at least 70 mg/day, at least 80 mg/day, at least 90 mg/day, at least 100 mg/day, at least 110 mg/day, at least 120 mg/day, at least 130 mg/day, at least 140 mg/day, at least 150 mg/day, at least 160 mg/day, at least 170 mg/day, at least 180 mg/day, at least 190 mg/day, at least 200 mg/day, at least 210 mg/day, at least 220 mg/day, at least 230 mg/day, at least 240 mg/day, at least 250 mg/day, at least 300 mg/day, at least 350 mg/day, at least 400 mg/day, at least 450 mg/day, at least 500 mg/day, at least 550 mg/day, at least 600 mg/day, at least 650 mg/day, at least 700 mg/day, at least 750 mg/day, at least 800 mg/day, at least 850 mg/day, at least 900 mg/day, at least 950 mg/day, at least 1,000 mg/day, at least 1,50 mg/day, at least 1,100 mg/day, at least 1,150 mg/day, at least 1,200 mg/day, at least 1,250 mg/day, at least 1,300 mg/day, at least 1,350 mg/day, at least 1,400 mg/day, at least 1,450 mg/day, at least 1,500 mg/day, at least 1,600 mg/day, at least 1,700 mg/day, at least 1,800 mg/day, at least 1,900 mg/day, at least 2,000 mg/day, at least 2,100 mg/day, at least 2,200 mg/day, at least 2,300 mg/day, at least 2,400 mg/day, at least 2,500 mg/day, at least 2,600 mg/day, at least 2,700 mg/day, at least 2,800 mg/day, at least 2,900 mg/day, or at least 3,000 mg/day. In yet aspects of this embodiment, an effective amount of a therapeutic compound disclosed herein may be, e.g., at most 40 mg/day, at most 50 mg/day, at most 60 mg/day, at most 70 mg/day, at most 80 mg/day, at most 90 mg/day, at most 100 mg/day, at most 110 mg/day, at most 120 mg/day, at most 130 mg/day, at most 140 mg/day, at most 150 mg/day, at most 160 mg/day, at most 170 mg/day, at most 180 mg/day, at most 190 mg/day, at most 200 mg/day, at most 210 mg/day, at most 220 mg/day, at most 230 mg/day, at most 240 mg/day, at most 250 mg/day, at most 300 mg/day, at most 350 mg/day, at most 400 mg/day, at most 450 mg/day, at most 500 mg/day, at most 550 mg/day, at most 600 mg/day, at most 650 mg/day, at most 700 mg/day, at most 750 mg/day, at most 800 mg/day, at most 850 mg/day, at most 900 mg/day, at most 950 mg/day, at most 1,000 mg/day, at most 1,50 mg/day, at most 1,100 mg/day, at most 1,150 mg/day, at most 1,200 mg/day, at most 1,250 mg/day, at most 1,300 mg/day, at most 1,350 mg/day, at most 1,400 mg/day, at most 1,450 mg/day, at most 1,500 mg/day, at most 1,600 mg/day, at most 1,700 mg/day, at most 1,800 mg/day, at most 1,900 mg/day, at most 2,000 mg/day, at most 2,100 mg/day, at most 2,200 mg/day, at most 2,300 mg/day, at most 2,400 mg/day, at most 2,500 mg/day, at most 2,600 mg/day, at most 2,700 mg/day, at most 2,800 mg/day, at most 2,900 mg/day, or at most 3,000 mg/day.

In still other aspects of this embodiment, an effective amount of a therapeutic compound disclosed herein may be between, e.g., about 40 mg/day to about 250 mg/day, about 50 mg/day to about 250 mg/day, about 60 mg/day to about 250 mg/day, about 70 mg/day to about 250 mg/day, about 80 mg/day to about 250 mg/day, about 90 mg/day to about 250 mg/day, about 100 mg/day to about 250 mg/day, about 40 mg/day to about 500 mg/day, about 50 mg/day to about 500 mg/day, about 60 mg/day to about 500 mg/day, about 70 mg/day to about 500 mg/day, about 80 mg/day to about 500 mg/day, about 90 mg/day to about 500 mg/day, about 100 mg/day to about 500 mg/day, about 40 mg/day to about 750 mg/day, about 50 mg/day to about 750 mg/day, about 60 mg/day to about 750 mg/day, about 70 mg/day to about 750 mg/day, about 80 mg/day to about 750 mg/day, about 90 mg/day to about 750 mg/day, about 100 mg/day to about 750 mg/day, about 50 mg/day to about 1,000 mg/day, about 100 mg/day to about 1,000 mg/day, about 150 mg/day to about 1,000 mg/day, about 200 mg/day to about 1,000 mg/day, about 250 mg/day to about 1,000 mg/day, about 300 mg/day to about 1,000 mg/day, about 350 mg/day to about 1,000 mg/day, about 400 mg/day to about 1,000 mg/day, about 450 mg/day to about 1,000 mg/day, about 500 mg/day to about 1,000 mg/day, about 50 mg/day to about 1,500 mg/day, about 100 mg/day to about 1,500 mg/day, about 150 mg/day to about 1,500 mg/day, about 200 mg/day to about 1,500 mg/day, about 250 mg/day to about 1,500 mg/day, about 300 mg/day to about 1,500 mg/day, about 350 mg/day to about 1,500 mg/day, about 400 mg/day to about 1,500 mg/day, about 450 mg/day to about 1,500 mg/day, about 500 mg/day to about 1,500 mg/day, about 1,000 mg/day to about 3,000 mg/day, about 1,100 mg/day to about 3,000 mg/day, about 1,200 mg/day to about 3,000 mg/day, about 1,3000 mg/day to about 3,000 mg/day, about 1,400 mg/day to about 3,000 mg/day, about 1,500 mg/day to about 3,000 mg/day, about 1,600 mg/day to about 3,000 mg/day, about 1,700 mg/day to about 3,000 mg/day, about 1,800 mg/day to about 3,000 mg/day, about 1,900 mg/day to about 3,000 mg/day, or about 2,000 mg/day to about 3,000 mg/day.

In other aspects of this embodiment, a therapeutically effective amount of a methylxanthine disclosed herein generally is in the range of about 0.001 mg/kg/day to about 100 mg/kg/day. In aspects of this embodiment, an effective amount of a methylxanthine disclosed herein may be, e.g., at least 0.001 mg/kg/day, at least 0.01 mg/kg/day, at least 0.1 mg/kg/day, at least 1.0 mg/kg/day, at least 5.0 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, or at least 50 mg/kg/day. In other aspects of this embodiment, an effective amount of a methylxanthine disclosed herein may be in the range of, e.g., about 0.001 mg/kg/day to about 10 mg/kg/day, about 0.001 mg/kg/day to about 15 mg/kg/day, about 0.001 mg/kg/day to about 20 mg/kg/day, about 0.001 mg/kg/day to about 25 mg/kg/day, about 0.001 mg/kg/day to about 30 mg/kg/day, about 0.001 mg/kg/day to about 35 mg/kg/day, about 0.001 mg/kg/day to about 40 mg/kg/day, about 0.001 mg/kg/day to about 45 mg/kg/day, about 0.001 mg/kg/day to about 50 mg/kg/day, about 0.001 mg/kg/day to about 75 mg/kg/day, or about 0.001 mg/kg/day to about 100 mg/kg/day. In yet other aspects of this embodiment, an effective amount of a methylxanthine disclosed herein may be in the range of, e.g., about 0.01 mg/kg/day to about 10 mg/kg/day, about 0.01 mg/kg/day to about 15 mg/kg/day, about 0.01 mg/kg/day to about 20 mg/kg/day, about 0.01 mg/kg/day to about 25 mg/kg/day, about 0.01 mg/kg/day to about 30 mg/kg/day, about 0.01 mg/kg/day to about 35 mg/kg/day, about 0.01 mg/kg/day to about 40 mg/kg/day, about 0.01 mg/kg/day to about 45 mg/kg/day, about 0.01 mg/kg/day to about 50 mg/kg/day, about 0.01 mg/kg/day to about 75 mg/kg/day, or about 0.01 mg/kg/day to about 100 mg/kg/day. In still other aspects of this embodiment, an effective amount of a methylxanthine disclosed herein may be in the range of, e.g., about 0.1 mg/kg/day to about 10 mg/kg/day, about 0.1 mg/kg/day to about 15 mg/kg/day, about 0.1 mg/kg/day to about 20 mg/kg/day, about 0.1 mg/kg/day to about 25 mg/kg/day, about 0.1 mg/kg/day to about 30 mg/kg/day, about 0.1 mg/kg/day to about 35 mg/kg/day, about 0.1 mg/kg/day to about 40 mg/kg/day, about 0.1 mg/kg/day to about 45 mg/kg/day, about 0.1 mg/kg/day to about 50 mg/kg/day, about 0.1 mg/kg/day to about 75 mg/kg/day, or about 0.1 mg/kg/day to about 100 mg/kg/day.

In other aspects of this embodiment, an effective amount of a methylxanthine disclosed herein may be in the range of, e.g., about 1 mg/kg/day to about 10 mg/kg/day, about 1 mg/kg/day to about 15 mg/kg/day, about 1 mg/kg/day to about 20 mg/kg/day, about 1 mg/kg/day to about 25 mg/kg/day, about 1 mg/kg/day to about 30 mg/kg/day, about 1 mg/kg/day to about 35 mg/kg/day, about 1 mg/kg/day to about 40 mg/kg/day, about 1 mg/kg/day to about 45 mg/kg/day, about 1 mg/kg/day to about 50 mg/kg/day, about 1 mg/kg/day to about 75 mg/kg/day, or about 1 mg/kg/day to about 100 mg/kg/day. In yet other aspects of this embodiment, an effective amount of a methylxanthine disclosed herein may be in the range of, e.g., about 5 mg/kg/day to about 10 mg/kg/day, about 5 mg/kg/day to about 15 mg/kg/day, about 5 mg/kg/day to about 20 mg/kg/day, about 5 mg/kg/day to about 25 mg/kg/day, about 5 mg/kg/day to about 30 mg/kg/day, about 5 mg/kg/day to about 35 mg/kg/day, about 5 mg/kg/day to about 40 mg/kg/day, about 5 mg/kg/day to about 45 mg/kg/day, about 5 mg/kg/day to about 50 mg/kg/day, about 5 mg/kg/day to about 75 mg/kg/day, or about 5 mg/kg/day to about 100 mg/kg/day.

In other aspects of this embodiment, a therapeutically effective amount of a methylxanthine disclosed herein generally is in the range of about 1 mg/day to about 3,000 mg/day. In aspects of this embodiment, an effective amount of a methylxanthine disclosed herein may be, e.g., at least 40 mg/day, at least 50 mg/day, at least 60 mg/day, at least 70 mg/day, at least 80 mg/day, at least 90 mg/day, at least 100 mg/day, at least 110 mg/day, at least 120 mg/day, at least 130 mg/day, at least 140 mg/day, at least 150 mg/day, at least 160 mg/day, at least 170 mg/day, at least 180 mg/day, at least 190 mg/day, at least 200 mg/day, at least 210 mg/day, at least 220 mg/day, at least 230 mg/day, at least 240 mg/day, at least 250 mg/day, at least 300 mg/day, at least 350 mg/day, at least 400 mg/day, at least 450 mg/day, at least 500 mg/day, at least 550 mg/day, at least 600 mg/day, at least 650 mg/day, at least 700 mg/day, at least 750 mg/day, at least 800 mg/day, at least 850 mg/day, at least 900 mg/day, at least 950 mg/day, at least 1,000 mg/day, at least 1,50 mg/day, at least 1,100 mg/day, at least 1,150 mg/day, at least 1,200 mg/day, at least 1,250 mg/day, at least 1,300 mg/day, at least 1,350 mg/day, at least 1,400 mg/day, at least 1,450 mg/day, at least 1,500 mg/day, at least 1,600 mg/day, at least 1,700 mg/day, at least 1,800 mg/day, at least 1,900 mg/day, at least 2,000 mg/day, at least 2,100 mg/day, at least 2,200 mg/day, at least 2,300 mg/day, at least 2,400 mg/day, at least 2,500 mg/day, at least 2,600 mg/day, at least 2,700 mg/day, at least 2,800 mg/day, at least 2,900 mg/day, or at least 3,000 mg/day. In yet aspects of this embodiment, an effective amount of a methylxanthine disclosed herein may be, e.g., at most 10 mg/day, at most 20 mg/day, at most 30 mg/day, at most 40 mg/day, at most 50 mg/day, at most 60 mg/day, at most 70 mg/day, at most 80 mg/day, at most 90 mg/day, at most 100 mg/day, at most 110 mg/day, at most 120 mg/day, at most 130 mg/day, at most 140 mg/day, at most 150 mg/day, at most 160 mg/day, at most 170 mg/day, at most 180 mg/day, at most 190 mg/day, at most 200 mg/day, at most 210 mg/day, at most 220 mg/day, at most 230 mg/day, at most 240 mg/day, at most 250 mg/day, at most 300 mg/day, at most 350 mg/day, at most 400 mg/day, at most 450 mg/day, at most 500 mg/day, at most 550 mg/day, at most 600 mg/day, at most 650 mg/day, at most 700 mg/day, at most 750 mg/day, at most 800 mg/day, at most 850 mg/day, at most 900 mg/day, at most 950 mg/day, at most 1,000 mg/day, at most 1,50 mg/day, at most 1,100 mg/day, at most 1,150 mg/day, at most 1,200 mg/day, at most 1,250 mg/day, at most 1,300 mg/day, at most 1,350 mg/day, at most 1,400 mg/day, at most 1,450 mg/day, at most 1,500 mg/day, at most 1,600 mg/day, at most 1,700 mg/day, at most 1,800 mg/day, at most 1,900 mg/day, at most 2,000 mg/day, at most 2,100 mg/day, at most 2,200 mg/day, at most 2,300 mg/day, at most 2,400 mg/day, at most 2,500 mg/day, at most 2,600 mg/day, at most 2,700 mg/day, at most 2,800 mg/day, at most 2,900 mg/day, or at most 3,000 mg/day.

In still other aspects of this embodiment, an effective amount of a methylxanthine disclosed herein may be between, e.g., about 5 mg/day to about 100 mg/day, about 5 mg/day to about 125 mg/day, about 5 mg/day to about 150 mg/day, about 5 mg/day to about 175 mg/day, about 5 mg/day to about 200 mg/day, about 5 mg/day to about 225 mg/day, about 5 mg/day to about 250 mg/day, about 10 mg/day to about 100 mg/day, about 10 mg/day to about 125 mg/day, about 10 mg/day to about 150 mg/day, about 10 mg/day to about 175 mg/day, about 10 mg/day to about 200 mg/day, about 10 mg/day to about 225 mg/day, about 10 mg/day to about 250 mg/day, about 10 mg/day to about 275 mg/day, about 10 mg/day to about 300 mg/day, about 25 mg/day to about 100 mg/day, about 25 mg/day to about 125 mg/day, about 25 mg/day to about 150 mg/day, about 25 mg/day to about 175 mg/day, about 25 mg/day to about 200 mg/day, about 25 mg/day to about 225 mg/day, about 25 mg/day to about 250 mg/day, about 25 mg/day to about 275 mg/day, about 25 mg/day to about 300 mg/day, about 40 mg/day to about 100 mg/day, about 40 mg/day to about 125 mg/day, about 40 mg/day to about 150 mg/day, about 40 mg/day to about 175 mg/day, about 40 mg/day to about 200 mg/day, about 40 mg/day to about 225 mg/day, about 40 mg/day to about 250 mg/day, about 40 mg/day to about 275 mg/day, about 40 mg/day to about 300 mg/day, about 50 mg/day to about 100 mg/day, about 50 mg/day to about 125 mg/day, about 50 mg/day to about 150 mg/day, about 50 mg/day to about 175 mg/day, about 50 mg/day to about 200 mg/day, about 50 mg/day to about 225 mg/day, about 50 mg/day to about 250 mg/day, about 50 mg/day to about 275 mg/day, about 50 mg/day to about 300 mg/day, about 75 mg/day to about 100 mg/day, about 75 mg/day to about 125 mg/day, about 75 mg/day to about 150 mg/day, about 75 mg/day to about 175 mg/day, about 75 mg/day to about 200 mg/day, about 75 mg/day to about 225 mg/day, about 75 mg/day to about 250 mg/day, about 75 mg/day to about 275 mg/day, about 75 mg/day to about 300 mg/day, about 75 mg/day to about 325 mg/day, about 75 mg/day to about 350 mg/day, about 75 mg/day to about 375 mg/day, about 75 mg/day to about 400 mg/day, about 75 mg/day to about 425 mg/day, about 75 mg/day to about 450 mg/day, about 75 mg/day to about 475 mg/day, about 75 mg/day to about 500 mg/day, about 75 mg/day to about 525 mg/day, about 75 mg/day to about 550 mg/day, about 75 mg/day to about 575 mg/day, about 75 mg/day to about 600 mg/day, about 100 mg/day to about 150 mg/day, about 100 mg/day to about 200 mg/day, about 100 mg/day to about 250 mg/day, about 100 mg/day to about 300 mg/day, about 100 mg/day to about 350 mg/day, about 100 mg/day to about 400 mg/day, about 100 mg/day to about 450 mg/day, about 100 mg/day to about 500 mg/day, about 100 mg/day to about 550 mg/day, about 100 mg/day to about 600 mg/day, about 100 mg/day to about 650 mg/day, about 100 mg/day to about 700 mg/day, about 100 mg/day to about 750 mg/day, about 150 mg/day to about 200 mg/day, about 150 mg/day to about 250 mg/day, about 150 mg/day to about 300 mg/day, about 150 mg/day to about 350 mg/day, about 150 mg/day to about 400 mg/day, about 150 mg/day to about 450 mg/day, about 150 mg/day to about 500 mg/day, about 150 mg/day to about 550 mg/day, about 150 mg/day to about 600 mg/day, about 150 mg/day to about 650 mg/day, about 150 mg/day to about 700 mg/day, about 150 mg/day to about 750 mg/day, about 200 mg/day to about 250 mg/day, about 200 mg/day to about 300 mg/day, about 200 mg/day to about 350 mg/day, about 200 mg/day to about 400 mg/day, about 200 mg/day to about 450 mg/day, about 200 mg/day to about 500 mg/day, about 200 mg/day to about 550 mg/day, about 200 mg/day to about 600 mg/day, about 200 mg/day to about 650 mg/day, about 200 mg/day to about 700 mg/day, about 200 mg/day to about 750 mg/day, about 200 mg/day to about 800 mg/day, about 250 mg/day to about 300 mg/day, about 250 mg/day to about 350 mg/day, about 250 mg/day to about 400 mg/day, about 250 mg/day to about 450 mg/day, about 250 mg/day to about 500 mg/day, about 250 mg/day to about 550 mg/day, about 250 mg/day to about 600 mg/day, about 250 mg/day to about 650 mg/day, about 250 mg/day to about 700 mg/day, about 250 mg/day to about 750 mg/day, about 250 mg/day to about 800 mg/day, about 250 mg/day to about 850 mg/day, about 250 mg/day to about 900 mg/day, about 250 mg/day to about 950 mg/day, about 250 mg/day to about 1000 mg/day, about 50 mg/day to about 1,000 mg/day, about 100 mg/day to about 1,000 mg/day, about 150 mg/day to about 1,000 mg/day, about 200 mg/day to about 1,000 mg/day, about 250 mg/day to about 1,000 mg/day, about 300 mg/day to about 1,000 mg/day, about 350 mg/day to about 1,000 mg/day, about 400 mg/day to about 1,000 mg/day, about 450 mg/day to about 1,000 mg/day, about 500 mg/day to about 1,000 mg/day, about 50 mg/day to about 1,500 mg/day, about 100 mg/day to about 1,500 mg/day, about 150 mg/day to about 1,500 mg/day, about 200 mg/day to about 1,500 mg/day, about 250 mg/day to about 1,500 mg/day, about 300 mg/day to about 1,500 mg/day, about 350 mg/day to about 1,500 mg/day, about 400 mg/day to about 1,500 mg/day, about 450 mg/day to about 1,500 mg/day, about 500 mg/day to about 1,500 mg/day, about 1,000 mg/day to about 3,000 mg/day, about 1,100 mg/day to about 3,000 mg/day, about 1,200 mg/day to about 3,000 mg/day, about 1,3000 mg/day to about 3,000 mg/day, about 1,400 mg/day to about 3,000 mg/day, about 1,500 mg/day to about 3,000 mg/day, about 1,600 mg/day to about 3,000 mg/day, about 1,700 mg/day to about 3,000 mg/day, about 1,800 mg/day to about 3,000 mg/day, about 1,900 mg/day to about 3,000 mg/day, or about 2,000 mg/day to about 3,000 mg/day.

In aspects of this embodiment, in conjunction with a methylxanthine, a therapeutically effective amount of a non-opiate antitussive disclosed herein generally is in the range of about 0.01 mg/kg/day to about 50 mg/kg/day. In other aspects of this embodiment, in conjunction with a methylxanthine, an effective amount of a non-opiate antitussive disclosed herein may be, e.g., at least 0.01 mg/kg/day, at least 0.025 mg/kg/day, at least 0.05 mg/kg/day, at least 0.075 mg/kg/day, at least 0.1 mg/kg/day, at least 0.25 mg/kg/day, at least 0.5 mg/kg/day, at least 0.75 mg/kg/day, at least 1.0 mg/kg/day, at least 2.5 mg/kg/day, at least 5.0 mg/kg/day, at least 7.5 mg/kg/day, at least 10 mg/kg/day, at least 25 mg/kg/day, or at least 50 mg/kg/day. In yet other aspects of this embodiment, in conjunction with a methylxanthine, an effective amount of a non-opiate antitussive disclosed herein may be, e.g., at least 0.1 mg/kg/day, at least 0.2 mg/kg/day, at least 0.3 mg/kg/day, at least 0.4 mg/kg/day, at least 0.5 mg/kg/day, at least 0.6 mg/kg/day, at least 0.7 mg/kg/day, at least 0.8 mg/kg/day, at least 0.9 mg/kg/day, at least 1.0 mg/kg/day, at least 1.25 mg/kg/day, at least 1.5 mg/kg/day, at least 1.75 mg/kg/day, at least 2.0 mg/kg/ day, at least 2.25 mg/kg/day, at least 2.5 mg/kg/day, at least 2.75 mg/kg/day, at least 3.0 mg/kg/day, at least 3.25 mg/kg/day, at least 3.5 mg/kg/day, at least 3.75 mg/kg/day, at least 4.0 mg/kg/day, at least 4.25 mg/kg/day, at least 4.5 mg/kg/day, at least 4.75 mg/kg/day, or at least 5.0 mg/kg/day. In yet other aspects of this embodiment, in conjunction with a methylxanthine, an effective amount of a non-opiate antitussive disclosed herein may be, e.g., about 0.01 mg/kg/day to about 0.1 mg/kg/day, about 0.01 mg/kg/day to about 0.5 mg/kg/day, about 0.01 mg/kg/day to about 1 mg/kg/day, about 0.01 mg/kg/day to about 5 mg/kg/day, about 0.01 mg/kg/day to about 10 mg/kg/day, about 0.1 mg/kg/day to about 0.1 mg/kg/day, about 0.1 mg/kg/day to about 0.5 mg/kg/day, about 0.1 mg/kg/day to about 1 mg/kg/day, about 0.1 mg/kg/day to about 5 mg/kg/day, or about 0.1 mg/kg/day to about 10 mg/kg/day.

In aspects of this embodiment, in conjunction with a methylxanthine, a therapeutically effective amount of a non-opiate antitussive disclosed herein generally is in the range of about 1 mg/day to about 500 mg/day. In other aspects of this embodiment, in conjunction with a methylxanthine, an effective amount of a non-opiate antitussive disclosed herein may be, e.g., at least 1 mg/day, at least 5 mg/day, at least 10 mg/day, at least 15 mg/day, at least 20 mg/day, at least 25 mg/day, at least 30 mg/day, at least 35 mg/day, at least 40 mg/day, at least 45 mg/day, at least 50 mg/day, at least 55 mg/day at least 60 mg/day at least 65 mg/day at least 70 mg/day at least 75 mg/day, at least 100 mg/day, at least 150 mg/day, at least 200 mg/day, at least 250 mg/day, at least 300 mg/day, at least 350 mg/day, at least 400 mg/day, at least 450 mg/day, or at least 500 mg/day. In yet other aspects of this embodiment, in conjunction with a methylxanthine, an effective amount of a non-opiate antitussive disclosed herein may be, e.g., at most 1 mg/day, at most 5 mg/day, at most 10 mg/day, at most 15 mg/day, at most 20 mg/day, at most 25 mg/day, at most 30 mg/day, at most 35 mg/day, at most 40 mg/day, at most 45 mg/day, at most 50 mg/day, at most 55 mg/day, at most 60 mg/day, at most 65 mg/day, at most 70 mg/day, at most 75 mg/day, at most 80 mg/day, at most 85 mg/day, at most 90 mg/day, at most 95 mg/day, at most 100 mg/day, at most 110 mg/day, at most 120 mg/day, at most 130 mg/day, at most 140 mg/day, at most 150 mg/day, at most 160 mg/day, at most 170 mg/day, at most 180 mg/day, at most 190 mg/day, at most 200 mg/day, at most 250 mg/day, at most 300 mg/day, at most 350 mg/day, at most 400 mg/day, at most 450 mg/day, or at most 500 mg/day.

In still other aspects of this embodiment, in conjunction with a methylxanthine, an effective amount of a non-opiate antitussive disclosed herein may be, e.g., about 1 mg/day to about 100 mg/day, about 1 mg/day to about 150 mg/day, about 1 mg/day to about 200 mg/day, about 1 mg/day to about 250 mg/day, about 1 mg/day to about 300 mg/day, about 1 mg/day to about 350 mg/day, about 1 mg/day to about 400 mg/day, about 1 mg/day to about 450 mg/day, about 1 mg/day to about 500 mg/day, about 10 mg/day to about 100 mg/day, about 10 mg/day to about 125 mg/day, about 10 mg/day to about 150 mg/day, about 10 mg/day to about 175 mg/day, about 10 mg/day to about 200 mg/day, about 10 mg/day to about 250 mg/day, about 10 mg/day to about 300 mg/day, about 10 mg/day to about 350 mg/day, about 10 mg/day to about 400 mg/day, about 10 mg/day to about 450 mg/day, about 10 mg/day to about 500 mg/day, about 20 mg/day to about 100 mg/day, about 20 mg/day to about 125 mg/day, about 20 mg/day to about 150 mg/day, about 20 mg/day to about 175 mg/day, about 20 mg/day to about 200 mg/day, about 20 mg/day to about 250 mg/day, about 20 mg/day to about 300 mg/day, about 20 mg/day to about 350 mg/day, about 20 mg/day to about 400 mg/day, about 20 mg/day to about 450 mg/day, about 20 mg/day to about 500 mg/day, about 30 mg/day to about 100 mg/day, about 30 mg/day to about 120 mg/day, about 30 mg/day to about 125 mg/day, about 30 mg/day to about 150 mg/day, about 30 mg/day to about 175 mg/day, about 30 mg/day to about 200 mg/day, about 30 mg/day to about 250 mg/day, about 30 mg/day to about 300 mg/day, about 30 mg/day to about 350 mg/day, about 30 mg/day to about 400 mg/day, about 30 mg/day to about 450 mg/day, or about 30 mg/day to about 500 mg/day.

In aspects of this embodiment, in conjunction with a methylxanthine, a therapeutically effective amount of an opiate antitussive disclosed herein generally is in the range of about 0.01 mg/kg/day to about 10 mg/kg/day. In other aspects of this embodiment, in conjunction with a methylxanthine, an effective amount of an opiate antitussive disclosed herein may be, e.g., at least 0.01 mg/kg/day, at least 0.025 mg/kg/day, at least 0.05 mg/kg/day, at least 0.075 mg/kg/day, at least 0.1 mg/kg/day, at least 0.25 mg/kg/day, at least 0.5 mg/kg/day, at least 0.75 mg/kg/day, at least 1.0 mg/kg/day, at least 2.5 mg/kg/day, at least 5.0 mg/kg/day, at least 7.5 mg/kg/day, or at least 10 mg/kg/day. In yet other aspects of this embodiment, in conjunction with a methylxanthine, an effective amount of an opiate antitussive disclosed herein may be, e.g., about 0.01 mg/kg/day to about 0.1 mg/kg/day, about 0.01 mg/kg/day to about 0.5 mg/kg/day, about 0.01 mg/kg/day to about 1 mg/kg/day, about 0.01 mg/kg/day to about 5 mg/kg/day, about 0.01 mg/kg/day to about 10 mg/kg/day, about 0.1 mg/kg/day to about 0.1 mg/kg/day, about 0.1 mg/kg/day to about 0.5 mg/kg/day, about 0.1 mg/kg/day to about 1 mg/kg/day, about 0.1 mg/kg/day to about 5 mg/kg/day, or about 0.1 mg/kg/day to about 10 mg/kg/day.

In aspects of this embodiment, in conjunction with a methylxanthine, a therapeutically effective amount of an opiate antitussive disclosed herein generally is in the range of about 0.1 mg/day to about 100 mg/day. In other aspects of this embodiment, in conjunction with a methylxanthine, an effective amount of an opiate antitussive disclosed herein may be, e.g., at least 0.1 mg/day, at least 0.5 mg/day, at least 1 mg/day, at least 2 mg/day, at least 3 mg/day, at least 4 mg/day, at least 5 mg/day, at least 6 mg/day, at least 7 mg/day, at least 8 mg/day, at least 9 mg/day, at least 10 mg/day, at least 15 mg/day, at least 20 mg/day, at least 25 mg/day, at least 30 mg/day, at least 40 mg/day, at least 50 mg/day, at least 60 mg/day, at least 70 mg/day, at least 80 mg/day, at least 90 mg/day, or at least 100 mg/day. In yet other aspects of this embodiment, in conjunction with a methylxanthine, an effective amount of an opiate antitussive disclosed herein may be, e.g., at most 0.1 mg/day, at most 0.5 mg/day, at most 1 mg/day, at most 2 mg/day, at most 3 mg/day, at most 4 mg/day, at most 5 mg/day, at most 6 mg/day, at most 7 mg/day, at most 8 mg/day, at most 9 mg/day, at most 10 mg/day, at most 15 mg/day, at most 20 mg/day, at most 25 mg/day, at most 30 mg/day, at most 40 mg/day, at most 50 mg/day, at most 60 mg/day, at most 70 mg/day, at most 80 mg/day, at most 90 mg/day, or at most 100 mg/day.

In still other aspects of this embodiment, in conjunction with a methylxanthine, an effective amount of an opiate antitussive disclosed herein may be, e.g., about 0.1 mg/day to about 5 mg/day, about 0.1 mg/day to about 10 mg/day, about 0.1 mg/day to about 15 mg/day, about 0.1 mg/day to about 20 mg/day, about 0.1 mg/day to about 25 mg/day, about 0.1 mg/day to about 30 mg/day, about 0.1 mg/day to about 40 mg/day, about 0.1 mg/day to about 60 mg/day, about 0.1 mg/day to about 80 mg/day, about 0.1 mg/day to about 100 mg/day, about 0.5 mg/day to about 5 mg/day, about 0.5 mg/day to about 10 mg/day, about 0.5 mg/day to about 15 mg/day, about 0.5 mg/day to about 20 mg/day, about 0.5 mg/day to about 25 mg/day, about 0.5 mg/day to about 30 mg/day, about 0.5 mg/day to about 40 mg/day, about 0.5 mg/day to about 60 mg/day, about 0.5 mg/day to about 80 mg/day, about 0.5 mg/day to about 100 mg/day, about 1 mg/day to about 5 mg/day, about 1 mg/day to about 10 mg/day, about 1 mg/day to about 15 mg/day, about 1 mg/day to about 20 mg/day, about 1 mg/day to about 25 mg/day, about 1 mg/day to about 30 mg/day, about 1 mg/day to about 40 mg/day, about 1 mg/day to about 60 mg/day, about 1 mg/day to about 80 mg/day, about 1 mg/day to about 100 mg/day, about 2.5 mg/day to about 10 mg/day, about 2.5 mg/day to about 20 mg/day, about 2.5 mg/day to about 40 mg/day, about 2.5 mg/day to about 60 mg/day, about 2.5 mg/day to about 80 mg/day, or about 2.5 mg/day to about 100 mg/day.

In other aspects of this embodiment, in conjunction with a methylxanthine, a therapeutically effective amount of a decongestant, an expectorant, and/or a mucolytic agent disclosed herein generally is in the range of about 0.001 mg/kg/day to about 100 mg/kg/day. In aspects of this embodiment, in conjunction with a methylxanthine, a therapeutically effective amount of a decongestant, an expectorant, and/or a mucolytic agent disclosed herein may be, e.g., at least 0.001 mg/kg/day, at least 0.01 mg/kg/day, at least 0.1 mg/kg/day, at least 1.0 mg/kg/day, at least 5.0 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, or at least 50 mg/kg/day. In other aspects of this embodiment, in conjunction with a methylxanthine, a therapeutically effective amount of a decongestant, an expectorant, and/or a mucolytic agent disclosed herein may be in the range of, e.g., about 0.001 mg/kg/day to about 10 mg/kg/day, about 0.001 mg/kg/day to about 15 mg/kg/day, about 0.001 mg/kg/day to about 20 mg/kg/day, about 0.001 mg/kg/day to about 25 mg/kg/day, about 0.001 mg/kg/day to about 30 mg/kg/day, about 0.001 mg/kg/day to about 35 mg/kg/day, about 0.001 mg/kg/day to about 40 mg/kg/day, about 0.001 mg/kg/day to about 45 mg/kg/day, about 0.001 mg/kg/day to about 50 mg/kg/day, about 0.001 mg/kg/day to about 75 mg/kg/day, or about 0.001 mg/kg/day to about 100 mg/kg/day. In yet other aspects of this embodiment, in conjunction with a methylxanthine, a therapeutically effective amount of a decongestant, an expectorant, and/or a mucolytic agent disclosed herein may be in the range of, e.g., about 0.01 mg/kg/day to about 10 mg/kg/day, about 0.01 mg/kg/day to about 15 mg/kg/day, about 0.01 mg/kg/day to about 20 mg/kg/day, about 0.01 mg/kg/day to about 25 mg/kg/day, about 0.01 mg/kg/day to about 30 mg/kg/day, about 0.01 mg/kg/day to about 35 mg/kg/day, about 0.01 mg/kg/day to about 40 mg/kg/day, about 0.01 mg/kg/day to about 45 mg/kg/day, about 0.01 mg/kg/day to about 50 mg/kg/day, about 0.01 mg/kg/day to about 75 mg/kg/day, or about 0.01 mg/kg/day to about 100 mg/kg/day. In still other aspects of this embodiment, in conjunction with a methylxanthine, a therapeutically effective amount of a decongestant, an expectorant, and/or a mucolytic agent disclosed herein may be in the range of, e.g., about 0.1 mg/kg/day to about 10 mg/kg/day, about 0.1 mg/kg/day to about 15 mg/kg/day, about 0.1 mg/kg/day to about 20 mg/kg/day, about 0.1 mg/kg/day to about 25 mg/kg/day, about 0.1 mg/kg/day to about 30 mg/kg/day, about 0.1 mg/kg/day to about 35 mg/kg/day, about 0.1 mg/kg/day to about 40 mg/kg/day, about 0.1 mg/kg/day to about 45 mg/kg/day, about 0.1 mg/kg/day to about 50 mg/kg/day, about 0.1 mg/kg/day to about 75 mg/kg/day, or about 0.1 mg/kg/day to about 100 mg/kg/day.

In other aspects of this embodiment, in conjunction with a methylxanthine, a therapeutically effective amount of a decongestant, an expectorant, and/or a mucolytic agent disclosed herein may be in the range of, e.g., about 1 mg/kg/day to about 10 mg/kg/day, about 1 mg/kg/day to about 15 mg/kg/day, about 1 mg/kg/day to about 20 mg/kg/day, about 1 mg/kg/day to about 25 mg/kg/day, about 1 mg/kg/day to about 30 mg/kg/day, about 1 mg/kg/day to about 35 mg/kg/day, about 1 mg/kg/day to about 40 mg/kg/day, about 1 mg/kg/day to about 45 mg/kg/day, about 1 mg/kg/day to about 50 mg/kg/day, about 1 mg/kg/day to about 75 mg/kg/day, or about 1 mg/kg/day to about 100 mg/kg/day. In yet other aspects of this embodiment, in conjunction with a methylxanthine, a therapeutically effective amount of a decongestant, an expectorant, and/or a mucolytic agent disclosed herein may be in the range of, e.g., about 5 mg/kg/day to about 10 mg/kg/day, about 5 mg/kg/day to about 15 mg/kg/day, about 5 mg/kg/day to about 20 mg/kg/day, about 5 mg/kg/day to about 25 mg/kg/day, about 5 mg/kg/day to about 30 mg/kg/day, about 5 mg/kg/day to about 35 mg/kg/day, about 5 mg/kg/day to about 40 mg/kg/day, about 5 mg/kg/day to about 45 mg/kg/day, about 5 mg/kg/day to about 50 mg/kg/day, about 5 mg/kg/day to about 75 mg/kg/day, or about 5 mg/kg/day to about 100 mg/kg/day.

In aspects of this embodiment, in conjunction with a methylxanthine, a therapeutically effective amount of a decongestant, an expectorant, and/or a mucolytic agent disclosed herein generally is in the range of about 0.1 mg/day to about 6,000 mg/day. In other aspects of this embodiment, in conjunction with a methylxanthine, a therapeutically effective amount of a decongestant, an expectorant, and/or a mucolytic agent disclosed herein may be, e.g., at least 0.1 mg/day, at least 0.5 mg/day, at least 1 mg/day, at least 2 mg/day, at least 3 mg/day, at least 4 mg/day, at least 5 mg/day, at least 6 mg/day, at least 7 mg/day, at least 8 mg/day, at least 9 mg/day, at least 10 mg/day, at least 15 mg/day, at least 20 mg/day, at least 25 mg/day, at least 30 mg/day, at least 40 mg/day, at least 50 mg/day, at least 100 mg/day, at least 150 mg/day, at least 200 mg/day, at least 250 mg/day, at least 300 mg/day, at least 350 mg/day, at least 400 mg/day, at least 450 mg/day, at least 500 mg/day, at least 550 mg/day, at least 600 mg/day, at least 650 mg/day, at least 700 mg/day, at least 750 mg/day, at least 800 mg/day, at least 850 mg/day, at least 900 mg/day, at least 950 mg/day, at least 1,000 mg/day, at least 1,50 mg/day, at least 1,100 mg/day, at least 1,150 mg/day, at least 1,200 mg/day, at least 1,250 mg/day, at least 1,300 mg/day, at least 1,350 mg/day, at least 1,400 mg/day, at least 1,450 mg/day, at least 1,500 mg/day, at least 1,600 mg/day, at least 1,700 mg/day, at least 1,800 mg/day, at least 1,900 mg/day, at least 2,000 mg/day, at least 2,100 mg/day, at least 2,200 mg/day, at least 2,300 mg/day, at least 2,400 mg/day, at least 2,500 mg/day, at least 2,600 mg/day, at least 2,700 mg/day, at least 2,800 mg/day, at least 2,900 mg/day, at least 3,000 mg/day, at least 3,500 mg/day, at least 4,000 mg/day, at least 4,500 mg/day, at least 5,000 mg/day, at least 5,500 mg/day, or at least 6,000 mg/day. In yet other aspects of this embodiment, in conjunction with a methylxanthine, a therapeutically effective amount of a decongestant, an expectorant, and/or a mucolytic agent disclosed herein may be, e.g., at most 0.1 mg/day, at most 0.5 mg/day, at most 1 mg/day, at most 2 mg/day, at most 3 mg/day, at most 4 mg/day, at most 5 mg/day, at most 6 mg/day, at most 7 mg/day, at most 8 mg/day, at most 9 mg/day, at most 10 mg/day, at most 15 mg/day, at most 20 mg/day, at most 25 mg/day, at most 30 mg/day, at most 40 mg/day, at most 50 mg/day, at most 100 mg/day, at most 150 mg/day, at most 200 mg/day, at most 250 mg/day, at most 300 mg/day, at most 350 mg/day, at most 400 mg/day, at most 450 mg/day, at most 500 mg/day, at most 550 mg/day, at most 600 mg/day, at most 650 mg/day, at most 700 mg/day, at most 750 mg/day, at most 800 mg/day, at most 850 mg/day, at most 900 mg/day, at most 950 mg/day, at most 1,000 mg/day, at most 1,50 mg/day, at most 1,100 mg/day, at most 1,150 mg/day, at most 1,200 mg/day, at most 1,250 mg/day, at most 1,300 mg/day, at most 1,350 mg/day, at most 1,400 mg/day, at most 1,450 mg/day, at most 1,500 mg/day, at most 1,600 mg/day, at most 1,700 mg/day, at most 1,800 mg/day, at most 1,900 mg/day, at most 2,000 mg/day, at most 2,100 mg/day, at most 2,200 mg/day, at most 2,300 mg/day, at most 2,400 mg/day, at most 2,500 mg/day, at most 2,600 mg/day, at most 2,700 mg/day, at most 2,800 mg/day, at most 2,900 mg/day, at most 3,000 mg/day, at most 3,500 mg/day, at most 4,000 mg/day, at most 4,500 mg/day, at most 5,000 mg/day, at most 5,500 mg/day, or at most 6,000 mg/day.

In still other aspects of this embodiment, in conjunction with a methylxanthine, a therapeutically effective amount of a decongestant, an expectorant, and/or a mucolytic agent disclosed herein may be between, e.g., about 1 mg/day to about 30 mg/day, about 5 mg/day to about 30 mg/day, about 10 mg/day to about 30 mg/day, about 15 mg/day to about 30 mg/day, about 1 mg/day to about 50 mg/day, about 5 mg/day to about 50 mg/day, about 15 mg/day to about 50 mg/day, about 20 mg/day to about 50 mg/day, about 25 mg/day to about 50 mg/day, about 1 mg/day to about 60 mg/day, about 5 mg/day to about 60 mg/day, about 15 mg/day to about 60 mg/day, about 25 mg/day to about 60 mg/day, about 30 mg/day to about 60 mg/day, about 40 mg/day to about 60 mg/day, about 50 mg/day to about 60 mg/day, about 1 mg/day to about 75 mg/day, about 5 mg/day to about 75 mg/day, about 15 mg/day to about 75 mg/day, about 20 mg/day to about 75 mg/day, about 25 mg/day to about 75 mg/day, about 30 mg/day to about 75 mg/day, about 40 mg/day to about 75 mg/day, about 50 mg/day to about 75 mg/day, about 1 mg/day to about 100 mg/day, about 25 mg/day to about 100 mg/day, about 50 mg/day to about 100 mg/day, about 75 mg/day to about 100 mg/day, about 1 mg/day to about 250 mg/day, about 25 mg/day to about 250 mg/day, about 50 mg/day to about 250 mg/day, about 100 mg/day to about 250 mg/day, about 150 mg/day to about 250 mg/day, about 200 mg/day to about 250 mg/day, about 1 mg/day to about 500 mg/day, about 25 mg/day to about 500 mg/day, about 50 mg/day to about 500 mg/day, about 100 mg/day to about 500 mg/day, about 150 mg/day to about 500 mg/day, about 200 mg/day to about 500 mg/day, about 250 mg/day to about 500 mg/day, about 300 mg/day to about 500 mg/day, about 350 mg/day to about 500 mg/day, about 400 mg/day to about 500 mg/day, about 450 mg/day to about 500 mg/day, about 1 mg/day to about 1,000 mg/day, about 25 mg/day to about 1,000 mg/day, about 50 mg/day to about 1,000 mg/day, about 100 mg/day to about 1,000 mg/day, about 150 mg/day to about 1,000 mg/day, about 200 mg/day to about 1,000 mg/day, about 250 mg/day to about 1,000 mg/day, about 300 mg/day to about 1,000 mg/day, about 350 mg/day to about 1,000 mg/day, about 400 mg/day to about 1,000 mg/day, about 450 mg/day to about 1,000 mg/day, about 500 mg/day to about 1,000 mg/day, about 50 mg/day to about 1,500 mg/day, about 100 mg/day to about 1,500 mg/day, about 150 mg/day to about 1,500 mg/day, about 200 mg/day to about 1,500 mg/day, about 250 mg/day to about 1,500 mg/day, about 300 mg/day to about 1,500 mg/day, about 350 mg/day to about 1,500 mg/day, about 400 mg/day to about 1,500 mg/day, about 450 mg/day to about 1,500 mg/day, about 500 mg/day to about 1,500 mg/day, about 1,000 mg/day to about 3,000 mg/day, about 1,100 mg/day to about 3,000 mg/day, about 1,200 mg/day to about 3,000 mg/day, about 1,3000 mg/day to about 3,000 mg/day, about 1,400 mg/day to about 3,000 mg/day, about 1,500 mg/day to about 3,000 mg/day, about 1,600 mg/day to about 3,000 mg/day, about 1,700 mg/day to about 3,000 mg/day, about 1,800 mg/day to about 3,000 mg/day, about 1,900 mg/day to about 3,000 mg/day, about 2,000 mg/day to about 3,000 mg/day, about 1,000 mg/day to about 4,000 mg/day, about 1,100 mg/day to about 4,000 mg/day, about 1,200 mg/day to about 4,000 mg/day, about 1,3000 mg/day to about 4,000 mg/day, about 1,400 mg/day to about 4,000 mg/day, about 1,500 mg/day to about 4,000 mg/day, about 1,600 mg/day to about 4,000 mg/day, about 1,700 mg/day to about 4,000 mg/day, about 1,800 mg/day to about 4,000 mg/day, about 1,900 mg/day to about 4,000 mg/day, about 2,000 mg/day to about 4,000 mg/day, about 2,500 mg/day to about 4,000 mg/day, about 3,000 mg/day to about 4,000 mg/day, about 1,000 mg/day to about 5,000 mg/day, about 1,100 mg/day to about 5,000 mg/day, about 1,200 mg/day to about 5,000 mg/day, about 1,3000 mg/day to about 5,000 mg/day, about 1,400 mg/day to about 5,000 mg/day, about 1,500 mg/day to about 5,000 mg/day, about 1,600 mg/day to about 5,000 mg/day, about 1,700 mg/day to about 5,000 mg/day, about 1,800 mg/day to about 5,000 mg/day, about 1,900 mg/day to about 5,000 mg/day, about 2,000 mg/day to about 5,000 mg/day, about 2,500 mg/day to about 5,000 mg/day, about 3,000 mg/day to about 5,000 mg/day, about 3,500 mg/day to about 5,000 mg/day, about 4,000 mg/day to about 5,000 mg/day, about 1,000 mg/day to about 6,000 mg/day, about 1,100 mg/day to about 6,000 mg/day, about 1,200 mg/day to about 6,000 mg/day, about 1,3000 mg/day to about 6,000 mg/day, about 1,400 mg/day to about 6,000 mg/day, about 1,500 mg/day to about 6,000 mg/day, about 1,600 mg/day to about 6,000 mg/day, about 1,700 mg/day to about 6,000 mg/day, about 1,800 mg/day to about 6,000 mg/day, about 1,900 mg/day to about 6,000 mg/day, about 2,000 mg/day to about 6,000 mg/day, about 2,500 mg/day to about 6,000 mg/day, about 3,000 mg/day to about 6,000 mg/day, about 3,500 mg/day to about 6,000 mg/day, about 4,000 mg/day to about 6,000 mg/day, about 4,500 mg/day to about 6,000 mg/day, or about 5,000 mg/day to about 6,000 mg/day.

In aspects of this embodiment, in conjunction with a methylxanthine, a therapeutically effective amount of an antihistamine disclosed herein generally is in the range of about 0.001 mg/kg/day to about 50 mg/kg/day. In other aspects of this embodiment, in conjunction with a methylxanthine, an effective amount of an antihistamine disclosed herein may be, e.g., at least 0.001 mg/kg/day, at least 0.0025 mg/kg/day, at least 0.005 mg/kg/day, at least 0.0075 mg/kg/day, at least 0.01 mg/kg/day, at least 0.025 mg/kg/day, at least 0.05 mg/kg/day, at least 0.075 mg/kg/day, at least 0.1 mg/kg/day, at least 0.25 mg/kg/day, at least 0.5 mg/kg/day, at least 0.75 mg/kg/day, at least 1.0 mg/kg/day, at least 2.5 mg/kg/day, at least 5.0 mg/kg/day, at least 7.5 mg/kg/day, at least 10 mg/kg/day, at least 25 mg/kg/day, or at least 50 mg/kg/day. In yet other aspects of this embodiment, in conjunction with a methylxanthine, an effective amount of an antihistamine disclosed herein may be, e.g., at least 0.1 mg/kg/day, at least 0.2 mg/kg/day, at least 0.3 mg/kg/day, at least 0.4 mg/kg/day, at least 0.5 mg/kg/day, at least 0.6 mg/kg/day, at least 0.7 mg/kg/day, at least 0.8 mg/kg/day, at least 0.9 mg/kg/day, at least 1.0 mg/kg/day, at least 1.25 mg/kg/day, at least 1.5 mg/kg/day, at least 1.75 mg/kg/day, at least 2.0 mg/kg/day, at least 2.25 mg/kg/day, at least 2.5 mg/kg/day, at least 2.75 mg/kg/day, at least 3.0 mg/kg/day, at least 3.25 mg/kg/day, at least 3.5 mg/kg/day, at least 3.75 mg/kg/day, at least 4.0 mg/kg/day, at least 4.25 mg/kg/day, at least 4.5 mg/kg/day, at least 4.75 mg/kg/day, or at least 5.0 mg/kg/day. In yet other aspects of this embodiment, in conjunction with a methylxanthine, an effective amount of an antihistamine disclosed herein may be, e.g., about 0.001 mg/kg/day to about 0.1 mg/kg/day, about 0.001 mg/kg/day to about 0.5 mg/kg/day, about 0.001 mg/kg/day to about 1 mg/kg/day, about 0.001 mg/kg/day to about 5 mg/kg/day, about 0.001 mg/kg/day to about 10 mg/kg/day, about 0.01 mg/kg/day to about 0.1 mg/kg/day, about 0.01 mg/kg/day to about 0.5 mg/kg/day, about 0.01 mg/kg/day to about 1 mg/kg/day, about 0.01 mg/kg/day to about 5 mg/kg/day, about 0.01 mg/kg/day to about 10 mg/kg/day, about 0.1 mg/kg/day to about 0.1 mg/kg/day, about 0.1 mg/kg/day to about 0.5 mg/kg/day, about 0.1 mg/kg/day to about 1 mg/kg/day, about 0.1 mg/kg/day to about 5 mg/kg/day, or about 0.1 mg/kg/day to about 10 mg/kg/day.

In aspects of this embodiment, in conjunction with a methylxanthine, a therapeutically effective amount of an antihistamine disclosed herein generally is in the range of about 1 mg/day to about 500 mg/day. In other aspects of this embodiment, in conjunction with a methylxanthine, an effective amount of an antihistamine disclosed herein may be, e.g., at least 1 mg/day, at least 5 mg/day, at least 10 mg/day, at least 15 mg/day, at least 20 mg/day, at least 25 mg/day, at least 30 mg/day, at least 35 mg/day, at least 40 mg/day, at least 45 mg/day, at least 50 mg/day, at least 55 mg/day at least 60 mg/day at least 65 mg/day at least 70 mg/day at least 75 mg/day, at least 100 mg/day, at least 150 mg/day, at least 200 mg/day, at least 250 mg/day, at least 300 mg/day, at least 350 mg/day, at least 400 mg/day, at least 450 mg/day, or at least 500 mg/day. In yet other aspects of this embodiment, in conjunction with a methylxanthine, an effective amount of an antihistamine disclosed herein may be, e.g., at most 1 mg/day, at most 5 mg/day, at most 10 mg/day, at most 15 mg/day, at most 20 mg/day, at most 25 mg/day, at most 30 mg/day, at most 35 mg/day, at most 40 mg/day, at most 45 mg/day, at most 50 mg/day, at most 55 mg/day, at most 60 mg/day, at most 65 mg/day, at most 70 mg/day, at most 75 mg/day, at most 80 mg/day, at most 85 mg/day, at most 90 mg/day, at most 95 mg/day, at most 100 mg/day, at most 110 mg/day, at most 120 mg/day, at most 130 mg/day, at most 140 mg/day, at most 150 mg/day, at most 160 mg/day, at most 170 mg/day, at most 180 mg/day, at most 190 mg/day, at most 200 mg/day, at most 250 mg/day, at most 300 mg/day, at most 350 mg/day, at most 400 mg/day, at most 450 mg/day, or at most 500 mg/day.

In still other aspects of this embodiment, in conjunction with a methylxanthine, an effective amount of an antihistamine disclosed herein may be, e.g., about 1 mg/day to about 100 mg/day, about 1 mg/day to about 150 mg/day, about 1 mg/day to about 200 mg/day, about 1 mg/day to about 250 mg/day, about 1 mg/day to about 300 mg/day, about 1 mg/day to about 350 mg/day, about 1 mg/day to about 400 mg/day, about 1 mg/day to about 450 mg/day, about 1 mg/day to about 500 mg/day, about 10 mg/day to about 100 mg/day, about 10 mg/day to about 125 mg/day, about 10 mg/day to about 150 mg/day, about 10 mg/day to about 175 mg/day, about 10 mg/day to about 200 mg/day, about 10 mg/day to about 250 mg/day, about 10 mg/day to about 300 mg/day, about 10 mg/day to about 350 mg/day, about 10 mg/day to about 400 mg/day, about 10 mg/day to about 450 mg/day, about 10 mg/day to about 500 mg/day, about 20 mg/day to about 100 mg/day, about 20 mg/day to about 125 mg/day, about 20 mg/day to about 150 mg/day, about 20 mg/day to about 175 mg/day, about 20 mg/day to about 200 mg/day, about 20 mg/day to about 250 mg/day, about 20 mg/day to about 300 mg/day, about 20 mg/day to about 350 mg/day, about 20 mg/day to about 400 mg/day, about 20 mg/day to about 450 mg/day, about 20 mg/day to about 500 mg/day, about 30 mg/day to about 100 mg/day, about 30 mg/day to about 120 mg/day, about 30 mg/day to about 125 mg/day, about 30 mg/day to about 150 mg/day, about 30 mg/day to about 175 mg/day, about 30 mg/day to about 200 mg/day, about 30 mg/day to about 250 mg/day, about 30 mg/day to about 300 mg/day, about 30 mg/day to about 350 mg/day, about 30 mg/day to about 400 mg/day, about 30 mg/day to about 450 mg/day, about 30 mg/day to about 500 mg/day, about 37.5 mg/day to about 100 mg/day, about 37.5 mg/day to about 120 mg/day, about 37.5 mg/day to about 125 mg/day, about 37.5 mg/day to about 150 mg/day, about 37.5 mg/day to about 175 mg/day, about 37.5 mg/day to about 200 mg/day, about 37.5 mg/day to about 250 mg/day, about 37.5 mg/day to about 300 mg/day, about 37.5 mg/day to about 350 mg/day, about 37.5 mg/day to about 400 mg/day, about 37.5 mg/day to about 450 mg/day, or about 37.5 mg/day to about 500 mg/day.

In other aspects of this embodiment, in conjunction with a methylxanthine, a therapeutically effective amount of a NSAID disclosed herein generally is in the range of about 0.001 mg/kg/day to about 100 mg/kg/day. In aspects of this embodiment, an effective amount of a methylxanthine disclosed herein may be, e.g., at least 0.001 mg/kg/day, at least 0.01 mg/kg/day, at least 0.1 mg/kg/day, at least 1.0 mg/kg/day, at least 5.0 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, or at least 50 mg/kg/day. In other aspects of this embodiment, in conjunction with a methylxanthine, a therapeutically effective amount of a NSAID disclosed herein may be in the range of, e.g., about 0.001 mg/kg/day to about 10 mg/kg/day, about 0.001 mg/kg/day to about 15 mg/kg/day, about 0.001 mg/kg/day to about 20 mg/kg/day, about 0.001 mg/kg/day to about 25 mg/kg/day, about 0.001 mg/kg/day to about 30 mg/kg/day, about 0.001 mg/kg/day to about 35 mg/kg/day, about 0.001 mg/kg/day to about 40 mg/kg/day, about 0.001 mg/kg/day to about 45 mg/kg/day, about 0.001 mg/kg/day to about 50 mg/kg/day, about 0.001 mg/kg/day to about 75 mg/kg/day, or about 0.001 mg/kg/day to about 100 mg/kg/day. In yet other aspects of this embodiment, in conjunction with a methylxanthine, a therapeutically effective amount of a NSAID disclosed herein may be in the range of, e.g., about 0.01 mg/kg/day to about 10 mg/kg/day, about 0.01 mg/kg/day to about 15 mg/kg/day, about 0.01 mg/kg/day to about 20 mg/kg/day, about 0.01 mg/kg/day to about 25 mg/kg/day, about 0.01 mg/kg/day to about 30 mg/kg/day, about 0.01 mg/kg/day to about 35 mg/kg/day, about 0.01 mg/kg/day to about 40 mg/kg/day, about 0.01 mg/kg/day to about 45 mg/kg/day, about 0.01 mg/kg/day to about 50 mg/kg/day, about 0.01 mg/kg/day to about 75 mg/kg/day, or about 0.01 mg/kg/day to about 100 mg/kg/day. In still other aspects of this embodiment, in conjunction with a methylxanthine, a therapeutically effective amount of a NSAID disclosed herein may be in the range of, e.g., about 0.1 mg/kg/day to about 10 mg/kg/day, about 0.1 mg/kg/day to about 15 mg/kg/day, about 0.1 mg/kg/day to about 20 mg/kg/day, about 0.1 mg/kg/day to about 25 mg/kg/day, about 0.1 mg/kg/day to about 30 mg/kg/day, about 0.1 mg/kg/day to about 35 mg/kg/day, about 0.1 mg/kg/day to about 40 mg/kg/day, about 0.1 mg/kg/day to about 45 mg/kg/day, about 0.1 mg/kg/day to about 50 mg/kg/day, about 0.1 mg/kg/day to about 75 mg/kg/day, or about 0.1 mg/kg/day to about 100 mg/kg/day.

In other aspects of this embodiment, in conjunction with a methylxanthine, a therapeutically effective amount of a NSAID disclosed herein may be in the range of, e.g., about 1 mg/kg/day to about 10 mg/kg/day, about 1 mg/kg/day to about 15 mg/kg/day, about 1 mg/kg/day to about 20 mg/kg/day, about 1 mg/kg/day to about 25 mg/kg/day, about 1 mg/kg/day to about 30 mg/kg/day, about 1 mg/kg/day to about 35 mg/kg/day, about 1 mg/kg/day to about 40 mg/kg/day, about 1 mg/kg/day to about 45 mg/kg/day, about 1 mg/kg/day to about 50 mg/kg/day, about 1 mg/kg/day to about 75 mg/kg/day, or about 1 mg/kg/day to about 100 mg/kg/day. In yet other aspects of this embodiment, in conjunction with a methylxanthine, a therapeutically effective amount of a NSAID disclosed herein may be in the range of, e.g., about 5 mg/kg/day to about 10 mg/kg/day, about 5 mg/kg/day to about 15 mg/kg/day, about 5 mg/kg/day to about 20 mg/kg/day, about 5 mg/kg/day to about 25 mg/kg/day, about 5 mg/kg/day to about 30 mg/kg/day, about 5 mg/kg/day to about 35 mg/kg/day, about 5 mg/kg/day to about 40 mg/kg/day, about 5 mg/kg/day to about 45 mg/kg/day, about 5 mg/kg/day to about 50 mg/kg/day, about 5 mg/kg/day to about 75 mg/kg/day, or about 5 mg/kg/day to about 100 mg/kg/day.

In other aspects of this embodiment, in conjunction with a methylxanthine, a therapeutically effective amount of a NSAID disclosed herein generally is in the range of about 1 mg/day to about 1,200 mg/day. In aspects of this embodiment, in conjunction with a methylxanthine, a therapeutically effective amount of a NSAID disclosed herein may be, e.g., at least 50 mg/day, at least 100 mg/day, at least 150 mg/day, at least 200 mg/day, at least 250 mg/day, at least 300 mg/day, at least 350 mg/day, at least 400 mg/day, at least 450 mg/day, at least 500 mg/day, at least 550 mg/day, at least 600 mg/day, at least 650 mg/day, at least 700 mg/day, at least 750 mg/day, at least 800 mg/day, at least 850 mg/day, at least 900 mg/day, at least 950 mg/day, at least 1,000 mg/day, at least 1,050 mg/day, at least 1,100 mg/day, at least 1,150 mg/day, or at least 1,200 mg/day. In aspects of this embodiment, in conjunction with a methylxanthine, a therapeutically effective amount of a NSAID disclosed herein may be, e.g., at most 50 mg/day, at most 100 mg/day, at most 150 mg/day, at most 200 mg/day, at most 250 mg/day, at most 300 mg/day, at most 350 mg/day, at most 400 mg/day, at most 450 mg/day, at most 500 mg/day, at most 550 mg/day, at most 600 mg/day, at most 650 mg/day, at most 700 mg/day, at most 750 mg/day, at most 800 mg/day, at most 850 mg/day, at most 900 mg/day, at most 950 mg/day, at most 1,000 mg/day, at most 1,050 mg/day, at most 1,100 mg/day, at most 1,150 mg/day, or at most 1,200 mg/day.

In still other aspects of this embodiment, in conjunction with a methylxanthine, a therapeutically effective amount of a NSAID disclosed herein may be between, e.g., about 50 mg/day to about 800 mg/day, about 100 mg/day to about 800 mg/day, about 150 mg/day to about 800 mg/day, about 200 mg/day to about 800 mg/day, about 250 mg/day to about 800 mg/day, about 300 mg/day to about 800 mg/day, about 350 mg/day to about 800 mg/day, about 400 mg/day to about 800 mg/day, about 450 mg/day to about 800 mg/day, about 500 mg/day to about 800 mg/day, about 50 mg/day to about 1,000 mg/day, about 100 mg/day to about 1,000 mg/day, about 150 mg/day to about 1,000 mg/day, about 200 mg/day to about 1,000 mg/day, about 250 mg/day to about 1,000 mg/day, about 300 mg/day to about 1,000 mg/day, about 350 mg/day to about 1,000 mg/day, about 400 mg/day to about 1,000 mg/day, about 450 mg/day to about 1,000 mg/day, about 500 mg/day to about 1,000 mg/day, about 50 mg/day to about 1,200 mg/day, about 100 mg/day to about 1,200 mg/day, about 150 mg/day to about 1,200 mg/day, about 200 mg/day to about 1,200 mg/day, about 250 mg/day to about 1,200 mg/day, about 300 mg/day to about 1,200 mg/day, about 350 mg/day to about 1,200 mg/day, about 400 mg/day to about 1,200 mg/day, about 450 mg/day to about 1,200 mg/day, about 500 mg/day to about 1,200 mg/day.

In other aspects of this embodiment, in conjunction with a methylxanthine, a therapeutically effective amount of a neuropathic pain agent disclosed herein generally is in the range of about 0.001 mg/kg/day to about 100 mg/kg/day. In aspects of this embodiment, in conjunction with a methylxanthine, a therapeutically effective amount of a neuropathic pain agent disclosed herein may be, e.g., at least 0.001 mg/kg/day, at least 0.01 mg/kg/day, at least 0.1 mg/kg/day, at least 1.0 mg/kg/day, at least 5.0 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, or at least 50 mg/kg/day. In other aspects of this embodiment, in conjunction with a methylxanthine, a therapeutically effective amount of a neuropathic pain agent disclosed herein may be in the range of, e.g., about 0.001 mg/kg/day to about 10 mg/kg/day, about 0.001 mg/kg/day to about 15 mg/kg/day, about 0.001 mg/kg/day to about 20 mg/kg/day, about 0.001 mg/kg/day to about 25 mg/kg/day, about 0.001 mg/kg/day to about 30 mg/kg/day, about 0.001 mg/kg/day to about 35 mg/kg/day, about 0.001 mg/kg/day to about 40 mg/kg/day, about 0.001 mg/kg/day to about 45 mg/kg/day, about 0.001 mg/kg/day to about 50 mg/kg/day, about 0.001 mg/kg/day to about 75 mg/kg/day, or about 0.001 mg/kg/day to about 100 mg/kg/day. In yet other aspects of this embodiment, in conjunction with a methylxanthine, a therapeutically effective amount of a neuropathic pain agent disclosed herein may be in the range of, e.g., about 0.01 mg/kg/day to about 10 mg/kg/day, about 0.01 mg/kg/day to about 15 mg/kg/day, about 0.01 mg/kg/day to about 20 mg/kg/day, about 0.01 mg/kg/day to about 25 mg/kg/day, about 0.01 mg/kg/day to about 30 mg/kg/day, about 0.01 mg/kg/day to about 35 mg/kg/day, about 0.01 mg/kg/day to about 40 mg/kg/day, about 0.01 mg/kg/day to about 45 mg/kg/day, about 0.01 mg/kg/day to about 50 mg/kg/day, about 0.01 mg/kg/day to about 75 mg/kg/day, or about 0.01 mg/kg/day to about 100 mg/kg/day. In still other aspects of this embodiment, in conjunction with a methylxanthine, a therapeutically effective amount of a neuropathic pain agent disclosed herein may be in the range of, e.g., about 0.1 mg/kg/day to about 10 mg/kg/day, about 0.1 mg/kg/day to about 15 mg/kg/day, about 0.1 mg/kg/day to about 20 mg/kg/day, about 0.1 mg/kg/day to about 25 mg/kg/day, about 0.1 mg/kg/day to about 30 mg/kg/day, about 0.1 mg/kg/day to about 35 mg/kg/day, about 0.1 mg/kg/day to about 40 mg/kg/day, about 0.1 mg/kg/day to about 45 mg/kg/day, about 0.1 mg/kg/day to about 50 mg/kg/day, about 0.1 mg/kg/day to about 75 mg/kg/day, or about 0.1 mg/kg/day to about 100 mg/kg/day.

In other aspects of this embodiment, in conjunction with a methylxanthine, a therapeutically effective amount of a neuropathic pain agent disclosed herein may be in the range of, e.g., about 1 mg/kg/day to about 10 mg/kg/day, about 1 mg/kg/day to about 15 mg/kg/day, about 1 mg/kg/day to about 20 mg/kg/day, about 1 mg/kg/day to about 25 mg/kg/ day, about 1 mg/kg/day to about 30 mg/kg/day, about 1 mg/kg/day to about 35 mg/kg/day, about 1 mg/kg/day to about 40 mg/kg/day, about 1 mg/kg/day to about 45 mg/kg/day, about 1 mg/kg/day to about 50 mg/kg/day, about 1 mg/kg/day to about 75 mg/kg/day, or about 1 mg/kg/day to about 100 mg/kg/day. In yet other aspects of this embodiment, in conjunction with a methylxanthine, a therapeutically effective amount of a neuropathic pain agent disclosed herein may be in the range of, e.g., about 5 mg/kg/day to about 10 mg/kg/day, about 5 mg/kg/day to about 15 mg/kg/day, about 5 mg/kg/day to about 20 mg/kg/day, about 5 mg/kg/day to about 25 mg/kg/day, about 5 mg/kg/day to about 30 mg/kg/day, about 5 mg/kg/day to about 35 mg/kg/day, about 5 mg/kg/day to about 40 mg/kg/day, about 5 mg/kg/day to about 45 mg/kg/day, about 5 mg/kg/day to about 50 mg/kg/day, about 5 mg/kg/day to about 75 mg/kg/day, or about 5 mg/kg/day to about 100 mg/kg/day.

In aspects of this embodiment, in conjunction with a methylxanthine, a therapeutically effective amount of a neuropathic pain agent disclosed herein generally is in the range of about 0.1 mg/day to about 6,000 mg/day. In other aspects of this embodiment, in conjunction with a methylxanthine, a therapeutically effective amount of a neuropathic pain agent disclosed herein may be, e.g., at least 0.1 mg/day, at least 0.5 mg/day, at least 1 mg/day, at least 2 mg/day, at least 3 mg/day, at least 4 mg/day, at least 5 mg/day, at least 6 mg/day, at least 7 mg/day, at least 8 mg/day, at least 9 mg/day, at least 10 mg/day, at least 15 mg/day, at least 20 mg/day, at least 25 mg/day, at least 30 mg/day, at least 40 mg/day, at least 50 mg/day, at least 100 mg/day, at least 150 mg/day, at least 200 mg/day, at least 250 mg/day, at least 300 mg/day, at least 350 mg/day, at least 400 mg/day, at least 450 mg/day, at least 500 mg/day, at least 550 mg/day, at least 600 mg/day, at least 650 mg/day, at least 700 mg/day, at least 750 mg/day, at least 800 mg/day, at least 850 mg/day, at least 900 mg/day, at least 950 mg/day, at least 1,000 mg/day, at least 1,50 mg/day, at least 1,100 mg/day, at least 1,150 mg/day, at least 1,200 mg/day, at least 1,250 mg/day, at least 1,300 mg/day, at least 1,350 mg/day, at least 1,400 mg/day, at least 1,450 mg/day, at least 1,500 mg/day, at least 1,600 mg/day, at least 1,700 mg/day, at least 1,800 mg/day, at least 1,900 mg/day, at least 2,000 mg/day, at least 2,100 mg/day, at least 2,200 mg/day, at least 2,300 mg/day, at least 2,400 mg/day, at least 2,500 mg/day, at least 2,600 mg/day, at least 2,700 mg/day, at least 2,800 mg/day, at least 2,900 mg/day, at least 3,000 mg/day, at least 3,500 mg/day, at least 4,000 mg/day, at least 4,500 mg/day, at least 5,000 mg/day, at least 5,500 mg/day, at least 6,000 mg/day, at least 6,500 mg/day, at least 7,000 mg/day, at least 7,500 mg/day, or at least 8,000 mg/day. In yet other aspects of this embodiment, in conjunction with a methylxanthine, a therapeutically effective amount of a neuropathic pain agent disclosed herein may be, e.g., at most 50 mg/day, at most 100 mg/day, at most 150 mg/day, at most 200 mg/day, at most 250 mg/day, at most 300 mg/day, at most 350 mg/day, at most 400 mg/day, at most 450 mg/day, at most 500 mg/day, at most 550 mg/day, at most 600 mg/day, at most 650 mg/day, at most 700 mg/day, at most 750 mg/day, at most 800 mg/day, at most 850 mg/day, at most 900 mg/day, at most 950 mg/day, at most 1,000 mg/day, at most 1,50 mg/day, at most 1,100 mg/day, at most 1,150 mg/day, at most 1,200 mg/day, at most 1,250 mg/day, at most 1,300 mg/day, at most 1,350 mg/day, at most 1,400 mg/day, at most 1,450 mg/day, at most 1,500 mg/day, at most 1,600 mg/day, at most 1,700 mg/day, at most 1,800 mg/day, at most 1,900 mg/day, at most 2,000 mg/day, at most 2,100 mg/day, at most 2,200 mg/day, at most 2,300 mg/day, at most 2,400 mg/day, at most 2,500 mg/day, at most 2,600 mg/day, at most 2,700 mg/day, at most 2,800 mg/day, at most 2,900 mg/day, at most 3,000 mg/day, at most 3,500 mg/day, at most 4,000 mg/day, at most 4,500 mg/day, at most 5,000 mg/day, at most 5,500 mg/day, at most 6,000 mg/day, at most 6,500 mg/day, at most 7,000 mg/day, at most 7,500 mg/day, or at most 8,000 mg/day.

In still other aspects of this embodiment, in conjunction with a methylxanthine, a therapeutically effective amount of a neuropathic pain agent disclosed herein may be between, e.g., about 1 mg/day to about 30 mg/day, about 5 mg/day to about 30 mg/day, about 10 mg/day to about 30 mg/day, about 15 mg/day to about 30 mg/day, about 1 mg/day to about 50 mg/day, about 5 mg/day to about 50 mg/day, about 15 mg/day to about 50 mg/day, about 20 mg/day to about 50 mg/day, about 25 mg/day to about 50 mg/day, about 1 mg/day to about 60 mg/day, about 5 mg/day to about 60 mg/day, about 15 mg/day to about 60 mg/day, about 25 mg/day to about 60 mg/day, about 30 mg/day to about 60 mg/day, about 40 mg/day to about 60 mg/day, about 50 mg/day to about 60 mg/day, about 1 mg/day to about 75 mg/day, about 5 mg/day to about 75 mg/day, about 15 mg/day to about 75 mg/day, about 20 mg/day to about 75 mg/day, about 25 mg/day to about 75 mg/day, about 30 mg/day to about 75 mg/day, about 40 mg/day to about 75 mg/day, about 50 mg/day to about 75 mg/day, about 1 mg/day to about 100 mg/day, about 25 mg/day to about 100 mg/day, about 50 mg/day to about 100 mg/day, about 75 mg/day to about 100 mg/day, about 1 mg/day to about 250 mg/day, about 25 mg/day to about 250 mg/day, about 50 mg/day to about 250 mg/day, about 100 mg/day to about 250 mg/day, about 150 mg/day to about 250 mg/day, about 200 mg/day to about 250 mg/day, about 1 mg/day to about 500 mg/day, about 25 mg/day to about 500 mg/day, about 50 mg/day to about 500 mg/day, about 100 mg/day to about 500 mg/day, about 150 mg/day to about 500 mg/day, about 200 mg/day to about 500 mg/day, about 250 mg/day to about 500 mg/day, about 300 mg/day to about 500 mg/day, about 350 mg/day to about 500 mg/day, about 400 mg/day to about 500 mg/day, about 450 mg/day to about 500 mg/day, about 1 mg/day to about 1,000 mg/day, about 25 mg/day to about 1,000 mg/day, about 50 mg/day to about 1,000 mg/day, about 100 mg/day to about 1,000 mg/day, about 150 mg/day to about 1,000 mg/day, about 200 mg/day to about 1,000 mg/day, about 250 mg/day to about 1,000 mg/day, about 300 mg/day to about 1,000 mg/day, about 350 mg/day to about 1,000 mg/day, about 400 mg/day to about 1,000 mg/day, about 450 mg/day to about 1,000 mg/day, about 500 mg/day to about 1,000 mg/day, about 50 mg/day to about 1,500 mg/day, about 100 mg/day to about 1,500 mg/day, about 150 mg/day to about 1,500 mg/day, about 200 mg/day to about 1,500 mg/day, about 250 mg/day to about 1,500 mg/day, about 300 mg/day to about 1,500 mg/day, about 350 mg/day to about 1,500 mg/day, about 400 mg/day to about 1,500 mg/day, about 450 mg/day to about 1,500 mg/day, about 500 mg/day to about 1,500 mg/day, about 1,000 mg/day to about 3,000 mg/day, about 1,100 mg/day to about 3,000 mg/day, about 1,200 mg/day to about 3,000 mg/day, about 1,3000 mg/day to about 3,000 mg/day, about 1,400 mg/day to about 3,000 mg/day, about 1,500 mg/day to about 3,000 mg/day, about 1,600 mg/day to about 3,000 mg/day, about 1,700 mg/day to about 3,000 mg/day, about 1,800 mg/day to about 3,000 mg/day, about 1,900 mg/day to about 3,000 mg/day, about 2,000 mg/day to about 3,000 mg/day, about 1,000 mg/day to about 4,000 mg/day, about 1,100 mg/day to about 4,000 mg/day, about 1,200 mg/day to about 4,000 mg/day, about 1,3000 mg/day to about 4,000 mg/day, about 1,400 mg/day to about 4,000 mg/day, about 1,500 mg/day to about 4,000 mg/day, about 1,600 mg/day to about 4,000 mg/day, about 1,700 mg/day to about 4,000 mg/day, about 1,800 mg/day to about 4,000 mg/day, about 1,900 mg/day to about 4,000 mg/day, about 2,000 mg/day to about 4,000 mg/day, about 2,500 mg/day to about 4,000 mg/day, about 3,000 mg/day to about 4,000 mg/day, about 1,000 mg/day to about 5,000 mg/day, about 1,100 mg/day to about 5,000 mg/day, about 1,200 mg/day to about 5,000 mg/day, about 1,3000 mg/day to about 5,000 mg/day, about 1,400 mg/day to about 5,000 mg/day, about 1,500 mg/day to about 5,000 mg/day, about 1,600 mg/day to about 5,000 mg/day, about 1,700 mg/day to about 5,000 mg/day, about 1,800 mg/day to about 5,000 mg/day, about 1,900 mg/day to about 5,000 mg/day, about 2,000 mg/day to about 5,000 mg/day, about 2,500 mg/day to about 5,000 mg/day, about 3,000 mg/day to about 5,000 mg/day, about 3,500 mg/day to about 5,000 mg/day, about 4,000 mg/day to about 5,000 mg/day, about 1,000 mg/day to about 6,000 mg/day, about 1,100 mg/day to about 6,000 mg/day, about 1,200 mg/day to about 6,000 mg/day, about 1,3000 mg/day to about 6,000 mg/day, about 1,400 mg/day to about 6,000 mg/day, about 1,500 mg/day to about 6,000 mg/day, about 1,600 mg/day to about 6,000 mg/day, about 1,700 mg/day to about 6,000 mg/day, about 1,800 mg/day to about 6,000 mg/day, about 1,900 mg/day to about 6,000 mg/day, about 2,000 mg/day to about 6,000 mg/day, about 2,500 mg/day to about 6,000 mg/day, about 3,000 mg/day to about 6,000 mg/day, about 3,500 mg/day to about 6,000 mg/day, about 4,000 mg/day to about 6,000 mg/day, about 4,500 mg/day to about 6,000 mg/day, or about 5,000 mg/day to about 6,000 mg/day, about 2,000 mg/day to about 7,000 mg/day, about 2,500 mg/day to about 7,000 mg/day, about 3,000 mg/day to about 7,000 mg/day, about 3,500 mg/day to about 7,000 mg/day, about 4,000 mg/day to about 7,000 mg/day, about 4,500 mg/day to about 7,000 mg/day, about 5,000 mg/day to about 7,000 mg/day, about 5,500 mg/day to about 7,000 mg/day, or about 6,000 mg/day to about 7,000 mg/day, about 2,000 mg/day to about 8,000 mg/day, about 2,500 mg/day to about 8,000 mg/day, about 3,000 mg/day to about 8,000 mg/day, about 3,500 mg/day to about 8,000 mg/day, about 4,000 mg/day to about 8,000 mg/day, about 4,500 mg/day to about 8,000 mg/day, about 5,000 mg/day to about 8,000 mg/day, about 5,500 mg/day to about 8,000 mg/day, about 6,000 mg/day to about 8,000 mg/day, about 6,500 mg/day to about 8,000 mg/day, or about 7,000 mg/day to about 8,000 mg/day.

In aspects of this embodiment, in conjunction with a methylxanthine, a therapeutically effective amount of a terpene disclosed herein generally is in the range of about 0.001 mg/kg/day to about 10 mg/kg/day. In other aspects of this embodiment, in conjunction with a methylxanthine, an effective amount of a terpene disclosed herein may be, e.g., at least 0.001 mg/kg/day, at least 0.0025 mg/kg/day, at least 0.005 mg/kg/day, at least 0.0075 mg/kg/day, at least 0.01 mg/kg/day, at least 0.025 mg/kg/day, at least 0.05 mg/kg/day, at least 0.075 mg/kg/day, at least 0.1 mg/kg/day, at least 0.25 mg/kg/day, at least 0.5 mg/kg/day, at least 0.75 mg/kg/day, at least 1.0 mg/kg/day, at least 2.5 mg/kg/day, at least 5.0 mg/kg/day, at least 7.5 mg/kg/day, or at least 10 mg/kg/day. In yet other aspects of this embodiment, in conjunction with a methylxanthine, an effective amount of a terpene disclosed herein may be, e.g., about 0.001 mg/kg/day to about 0.1 mg/kg/day, about 0.001 mg/kg/day to about 0.5 mg/kg/day, about 0.001 mg/kg/day to about 1 mg/kg/day, about 0.001 mg/kg/day to about 5 mg/kg/day, about 0.001 mg/kg/day to about 10 mg/kg/day, about 0.01 mg/kg/day to about 0.1 mg/kg/day, about 0.01 mg/kg/day to about 0.5 mg/kg/day, about 0.01 mg/kg/day to about 1 mg/kg/day, about 0.01 mg/kg/day to about 5 mg/kg/day, about 0.01 mg/kg/day to about 10 mg/kg/day, about 0.1 mg/kg/day to about 0.1 mg/kg/day, about 0.1 mg/kg/day to about 0.5 mg/kg/day, about 0.1 mg/kg/day to about 1 mg/kg/day, about 0.1 mg/kg/day to about 5 mg/kg/day, or about 0.1 mg/kg/day to about 10 mg/kg/day.

In aspects of this embodiment, in conjunction with a methylxanthine, a therapeutically effective amount of a terpene disclosed herein generally is in the range of about 0.1 mg/day to about 500 mg/day. In other aspects of this embodiment, in conjunction with a methylxanthine, an effective amount of a terpene disclosed herein may be, e.g., at least 0.1 mg/day, at least 0.5 mg/day, at least 1 mg/day, at least 5 mg/day, at least 10 mg/day, at least 20 mg/day, at least 30 mg/day, at least 40 mg/day, at least 50 mg/day, at least 60 mg/day, at least 70 mg/day, at least 80 mg/day, at least 90 mg/day, at least 100 mg/day, at least 150 mg/day, at least 200 mg/day, at least 250 mg/day, at least 300 mg/day, at least 350 mg/day, at least 400 mg/day, at least 450 mg/day, or at least 500 mg/day. In yet other aspects of this embodiment, in conjunction with a methylxanthine, an effective amount of a terpene disclosed herein may be, e.g., at most 0.1 mg/day, at most 0.5 mg/day, at most 1 mg/day, at most 5 mg/day, at most 10 mg/day, at most 20 mg/day, at most 30 mg/day, at most 40 mg/day, at most 50 mg/day, at most 60 mg/day, at most 70 mg/day, at most 80 mg/day, at most 90 mg/day, at most 100 mg/day, at most 150 mg/day, at most 200 mg/day, at most 250 mg/day, at most 300 mg/day, at most 350 mg/day, at most 400 mg/day, at most 450 mg/day, or at most 500 mg/day.

In still other aspects of this embodiment, in conjunction with a methylxanthine, an effective amount of a terpene disclosed herein may be, e.g., about 0.1 mg/day to about 10 mg/day, about 0.1 mg/day to about 20 mg/day, about 0.1 mg/day to about 40 mg/day, about 0.1 mg/day to about 60 mg/day, about 0.1 mg/day to about 80 mg/day, about 0.1 mg/day to about 100 mg/day, about 1 mg/day to about 10 mg/day, about 1 mg/day to about 20 mg/day, about 1 mg/day to about 40 mg/day, about 1 mg/day to about 60 mg/day, about 1 mg/day to about 80 mg/day, about 1 mg/day to about 100 mg/day, about 1 mg/day to about 150 mg/day, about 1 mg/day to about 200 mg/day, about 1 mg/day to about 250 mg/day, about 1 mg/day to about 300 mg/day, about 1 mg/day to about 350 mg/day, about 1 mg/day to about 400 mg/day, about 1 mg/day to about 450 mg/day, about 1 mg/day to about 500 mg/day, about 2.5 mg/day to about 10 mg/day, about 2.5 mg/day to about 20 mg/day, about 2.5 mg/day to about 40 mg/day, about 2.5 mg/day to about 60 mg/day, about 2.5 mg/day to about 80 mg/day, about 2.5 mg/day to about 100 mg/day, about 2.5 mg/day to about 100 mg/day, about 2.5 mg/day to about 150 mg/day, about 2.5 mg/day to about 200 mg/day, about 2.5 mg/day to about 250 mg/day, about 2.5 mg/day to about 300 mg/day, about 2.5 mg/day to about 350 mg/day, about 2.5 mg/day to about 400 mg/day, about 2.5 mg/day to about 450 mg/day, about 2.5 mg/day to about 500 mg/day, about 10 mg/day to about 100 mg/day, about 10 mg/day to about 150 mg/day, about 10 mg/day to about 200 mg/day, about 10 mg/day to about 250 mg/day, about 10 mg/day to about 300 mg/day, about 10 mg/day to about 350 mg/day, about 10 mg/day to about 400 mg/day, about 10 mg/day to about 450 mg/day, or about 10 mg/day to about 500 mg/day.

In aspects of this embodiment, in conjunction with a methylxanthine, a therapeutically effective amount of an ACE inhibitor and/or an angiotensin II receptor antagonist disclosed herein generally is in the range of about 0.01 mg/kg/day to about 10 mg/kg/day. In other aspects of this embodiment, in conjunction with a methylxanthine, an effective amount of an ACE inhibitor and/or an angiotensin II receptor antagonist disclosed herein may be, e.g., at least 0.01 mg/kg/day, at least 0.025 mg/kg/day, at least 0.05 mg/kg/day, at least 0.075 mg/kg/day, at least 0.1 mg/kg/day, at least 0.25 mg/kg/day, at least 0.5 mg/kg/day, at least 0.75 mg/kg/day, at least 1.0 mg/kg/day, at least 2.5 mg/kg/day, at least 5.0 mg/kg/day, at least 7.5 mg/kg/day, or at least 10 mg/kg/day. In yet other aspects of this embodiment, in conjunction with a methylxanthine, an effective amount of an ACE inhibitor and/or an angiotensin II receptor antagonist disclosed herein may be, e.g., about 0.01 mg/kg/day to about 0.1 mg/kg/day, about 0.01 mg/kg/day to about 0.5 mg/kg/day, about 0.01 mg/kg/day to about 1 mg/kg/day, about 0.01 mg/kg/day to about 5 mg/kg/day, about 0.01 mg/kg/day to about 10 mg/kg/day, about 0.1 mg/kg/day to about 0.1 mg/kg/day, about 0.1 mg/kg/day to about 0.5 mg/kg/day, about 0.1 mg/kg/day to about 1 mg/kg/day, about 0.1 mg/kg/day to about 5 mg/kg/day, or about 0.1 mg/kg/day to about 10 mg/kg/day.

In aspects of this embodiment, in conjunction with a methylxanthine, a therapeutically effective amount of an ACE inhibitor and/or an angiotensin II receptor antagonist disclosed herein generally is in the range of about 1 mg/day to about 500 mg/day. In other aspects of this embodiment, in conjunction with a methylxanthine, an effective amount of an ACE inhibitor and/or an angiotensin II receptor antagonist disclosed herein may be, e.g., at least 1 mg/day, at least 5 mg/day, at least 10 mg/day, at least 25 mg/day, at least 50 mg/day, at least 75 mg/day, at least 100 mg/day, at least 150 mg/day, at least 200 mg/day, at least 250 mg/day, at least 300 mg/day, at least 350 mg/day, at least 400 mg/day, at least 450 mg/day, or at least 500 mg/day. In yet other aspects of this embodiment, in conjunction with a methylxanthine, an effective amount of an ACE inhibitor and/or an angiotensin II receptor antagonist disclosed herein may be, e.g., at most 1 mg/day, at most 5 mg/day, at most 10 mg/day, at most 25 mg/day, at most 50 mg/day, at most 75 mg/day, at most 100 mg/day, at most 150 mg/day, at most 200 mg/day, at most 250 mg/day, at most 300 mg/day, at most 350 mg/day, at most 400 mg/day, at most 450 mg/day, or at most 500 mg/day.

In still other aspects of this embodiment, in conjunction with a methylxanthine, an effective amount of an ACE inhibitor and/or an angiotensin II receptor antagonist disclosed herein may be, e.g., about 1 mg/day to about 100 mg/day, about 1 mg/day to about 150 mg/day, about 1 mg/day to about 200 mg/day, about 1 mg/day to about 250 mg/day, about 1 mg/day to about 300 mg/day, about 1 mg/day to about 350 mg/day, about 1 mg/day to about 400 mg/day, about 1 mg/day to about 450 mg/day, about 1 mg/day to about 500 mg/day, about 10 mg/day to about 100 mg/day, about 10 mg/day to about 150 mg/day, about 10 mg/day to about 200 mg/day, about 10 mg/day to about 250 mg/day, about 10 mg/day to about 300 mg/day, about 10 mg/day to about 350 mg/day, about 10 mg/day to about 400 mg/day, about 10 mg/day to about 450 mg/day, or about 10 mg/day to about 500 mg/day.

Dosing can be single dosage or cumulative (serial dosing), and can be readily determined by one skilled in the art. For instance, treatment of a coughing condition may comprise a one-time administration of an effective dose of a pharmaceutical composition disclosed herein. Alternatively, treatment of a coughing condition may comprise multiple administrations of an effective dose of a pharmaceutical composition carried out over a range of time periods, such as, e.g., once daily, twice daily, trice daily, once every few days, or once weekly. The timing of administration can vary from individual to individual, depending upon such factors as the severity of an individual's symptoms. For example, an effective dose of a pharmaceutical composition disclosed herein can be administered to an individual once daily for an indefinite period of time, or until the individual no longer requires therapy. A person of ordinary skill in the art will recognize that the condition of the individual can be monitored throughout the course of treatment and that the effective amount of a pharmaceutical composition disclosed herein that is administered can be adjusted accordingly.

Various routes of administration can be useful for administering a therapeutic compound disclosed herein, according to a method of treating a coughing condition disclosed herein. A pharmaceutical composition may be administered to an individual by any of a variety of means depending, e.g., on the type of coughing condition to be treated, the location of coughing condition to be treated, the specific therapeutic compound or composition used, or other compound to be included in the composition, and the history, risk factors and symptoms of the individual. As such, topical, enteral or parenteral routes of administration may be suitable for of treating a coughing condition disclosed herein and such routes include both local and systemic delivery of a therapeutic compound or composition disclosed herein. Compositions comprising either a single therapeutic compound disclosed herein, or two or more therapeutic compounds disclosed herein are intended for inhaled, topical, intranasal, sublingual, intravenous, rectal and/or vaginal use may be prepared according to any method known to the art for the manufacture of pharmaceutical compositions.

A pharmaceutical composition disclosed herein can be administered to an individual in a single formulation or in separate formulations, for combined, simultaneous or sequential administration. In one embodiment, an individual is administered a first composition comprising a methylxanthine and a second composition comprising another therapeutic compound having antitussive activity. In aspects of this embodiment, an individual is administered a first composition comprising at least one methylxanthine and a second composition comprising at least one other therapeutic compound having antitussive activity. In aspects of this embodiment, the at least one other therapeutic compound having antitussive activity includes, without limitation, a non-opiate antitussive, an opiate antitussive, a decongestant, an expectorant, a mucolytic agent, an anti-histamine, a non-steroidal anti-inflammatory drug (NSAID), a neuropathic pain agent, a terpene, an ace inhibitor, and/or an angiotensin II receptor antagonist.

In another embodiment, an individual is administered a composition comprising a methylxanthine and another therapeutic compound having antitussive activity. In aspects of this embodiment, an individual is administered a composition comprising at least one methylxanthine and at least one other therapeutic compound having antitussive activity. In aspects of this embodiment, the at least one other therapeutic compound having antitussive activity includes, without limitation, a non-opiate antitussive, an opiate antitussive, a decongestant, an expectorant, a mucolytic agent, an anti-histamine, a non-steroidal anti-inflammatory drug (NSAID), a neuropathic pain agent, a terpene, an ace inhibitor, and/or an angiotensin II receptor antagonist.

A pharmaceutical composition disclosed herein can also be administered to an individual in combination with other therapeutic compounds to increase the overall therapeutic effect of the treatment. The use of multiple compounds to treat an indication can increase the beneficial effects while reducing the presence of side effects.

In an aspect of this embodiment, $\beta_2$-agonists, such as, e.g. salbutamol, salmeterol and formoterol, may be formulated for co-administration with a therapeutic compound or composition disclosed herein. In another aspect of this embodiment, anti-muscarinic compounds, such as, e.g., ipratropium (e.g. ipratropium bromide) or tiotropium may be formulated for co-administration with a therapeutic compound or composition disclosed herein. In yet another aspect of this embodiment, steroids, such as, e.g., beclomethasone, dipropionate and fluticasone may be formulated for co-administration with a therapeutic compound or composition disclosed herein. In still another aspect of this embodiment, matrix metalloproteinase inhibitors, leukotrienes, antibiotics, anti-infective agents, antineoplastics, peptides, antitussives, nicotine, PDE4 inhibitors, elastase inhibitors and/or sodium cromoglycate may be formulated for co-administration with a therapeutic compound or composition disclosed herein.

Aspects of the present specification may also be described as follows:

1. A composition comprising a methylxanthine or a cocoa and a plurality of additional therapeutic agent having antitussive activity.
2. The composition according to embodiment 1, wherein the methylxanthine includes Aminophylline, Caffeine, IBMX, Paraxanthine, Pentoxifylline, Theobromine, Theophylline, Xanthine, or any combination thereof.
3. The composition according to embodiment 1 or 2, wherein the plurality of therapeutic agent having antitussive activity includes a non-opiate antitussive agent, an opiate antitussive agent, a decongestant, an expectorant, a mucolytic agent, an anti-histamine, a non-steroidal anti-inflammatory drug (NSAID), a neuropathic pain agent, a terpene, an ACE inhibitor, an angiotensin II receptor antagonist or any combination thereof.
4. The composition according to embodiment 3, wherein the non-opiate antitussive agent includes Benproperine, Benzonate, Bibenzonium, Butamirate, Cloperastine, Clofedanol, Dextromethorphan, Dibunate, Dimemorfan, Dropropizine, Fedrilate, Indantadol, Isoaminile, Morclofone, Meprotixol, Nepinalone, Oxolamine, Oxeladin, Piperidione, Pentoxyverine, Prenoxdiazine, Zipeprol. or any combination thereof.
5. The composition according to embodiment 3, wherein the opiate antitussive agent includes Alfentanil, Alphamethylfentanyl, Buprenorphine, Carfentanyl, Codeine, Diamorphine, Dihydrocodeine, Ethyl Morphine, Etorphine, Fentanyl, Hydrocodone, Hydromorphone, Loperamide, Morphine, Noscapine, Oripavine, Oxymorphone, Oxycodone, Papaverine, Pentazocine, Pethidine, Propoxyphene, Remifentanil, Sufentanil, Thebaine, Tipepidine, Tramadol, or any combination thereof.
6. The composition according to embodiment 3, wherein the decongestant includes Ephedrine, Levmetamfetamine, Naphazoline, Oxymetazoline, Phenylephrine, Phenylpropanolamine, Propylhexedrine, Pseudoephedrine, Synephrine, Tetrahydrozoline, or any combination thereof.
7. The composition according to embodiment 3, wherein the expectorant includes Ambroxol, Ammonium Bicarbonate, Ammonium Carbonate, Bromhexine, Calcium Iodide, Carbocysteine, Guaiacol, Guaiacol Benzoate, Guaiacol Carbonate, Guaiacol Phosphate, Guaifenesin, Guaithylline, Hydriodic Acid, Iodinated Glycerol, Potassium Guaiacolsulfonate, Potassium Iodide, Sodium Citrate, Sodium Iodide, Storax Terebene, Terpin, Trifolium, Althea Root, Antimony Pentasulfide, Creosote, Ipecacuanha (Syrup of Ipecac), Levoverbenone, Senega, Tyloxapol, or any combination thereof.
8. The composition according to embodiment 3, wherein the mucolytic agent includes Acetylcysteine, Bromhexine, Carbocysteine, Domiodol, Erdostine, Letostine, Lysozyme, Mecysteine Hydrochloride, Mesna, Sobrerol, Stepronin, Tiopronin, Tyloxapol, Ambroxol, Ammonium Chloride, Dornase Alfa, Eprazinone, Erdosteine, Letosteine, Neltenexine, or any combination thereof.
9. The composition according to embodiment 3, wherein the anti-histamine includes Acrivastine, Alimemazine, Astemizole, Azatadine, Bromodiphenhydramine, Brompheniramine, Carbinoxamine, Cetirizine, Chlorpheniramine, Clemastine, Cyproheptadine, Desloratadine, Dexchlorpheniramine, Dextrobrompheniramine, Dimenhydrinate, Diphenhydramine, Doxylamine, Fexofenadine, Hydroxyzine, Levocetirizine, Loratadine, Meclizine, Mizolastine, Quetiapine, Pheniramine, Promethazine, Pyrilamine, Tripelennamine, Triprolidine., or any combination thereof.
10. The composition according to embodiment 3, wherein the NSAID includes a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclo-oxygenase (COX) inhibitor, a selective cyclooxygenase 1 (COX 1) inhibitor, a selective cyclooxygenase 2 (COX 2) inhibitor, or any combination thereof.
11. The composition according to embodiment 3, wherein the neuropathic pain agent includes Acetazolamide, Amitriptyline, Amitriptylinoxide, Baclofen, Butriptyline, Carbamazepine, Carisoprodol, Clobazam, Clomipramine, Conotoxins, Cyclobenzaprine, Demexiptiline, Desipramine, Diazepam, Dibenzepin, Dimetacrine, Doxepin, Duloexetine, Ethotoin, Felbamate, Fosphenyloin, Gabapentin, Imipramine, Imipraminoxide, Ketamine, Lamotrigine, Lidocaine, Lignocaine, Lofepramine, Mephenyloin, Melitracen, Metapramine, Metaxalone, Methadone, Methocarbamol, Nitroxazepine, Nortriptyline, Noxiptiline, Oxcarbazepine, Phenobarbital, Phensuximide, Phenyloin, Pipofezine, Pregabalin, Progabide, Propizepine, Protriptyline, Quinupramine, Stiripentol, Tiagabine, Topiramate, Trimethadione, Valproate, Venlafaxine, Vigabatrin, Zonisamide, or any combination thereof.
12. The composition according to embodiment 3, wherein the terpene includes camphor oil, citronella, clove oil, eucalyptus oil, ginger oil, horsemint oil, l-menthol, lemon oil, limonene, marjoram oil, mint oil, neroli oil, peppermint oil, pine oil, rose oil, rosemary oil, spearmint oil, tea tree oil, thyme oil, water mint oil, or any combination thereof.
13. The composition according to embodiment 3, wherein the ACE inhibitor includes Captopril, Enalapril, Lisinopril, Meleate, Ramipril, or any combination thereof.
14. The composition according to embodiment 3, wherein the angiotensin II receptor antagonist includes Azilsartan, Candesartan, Eprosartan, Irbesartan, Losartan, Olmesartan, Telmisartan, Valsartan, or any combination thereof.
15. The composition according to embodiments 1-3, wherein the plurality of therapeutic compounds does not include a non-opiate antitussive agent.
16. The composition according to embodiments 1-4, wherein the plurality of therapeutic compounds does not include Dextromethorphan.

17. The composition according to embodiments 1-3, wherein the plurality of therapeutic compounds does not include an anti-histamine.
18. The composition according to embodiments 1-3 or 9, wherein the plurality of therapeutic compounds does not include Azatadine, Bromodiphenhydramine, Brompheniramine, Carbinoxamine, Cetirizine, Chlorpheniramine, Clemestine, Dexchlorpheniramine, Dexbrompheniramine, Diphenhydramine, Doxylamine, Pyrilamine, Tripelennamine, or Tripolidine.
19. The composition according to embodiments 1-18, wherein the pharmaceutical composition reduces an unwanted side.
20. The composition according to embodiment 19, wherein the unwanted side includes sedation, cognitive fogging, dizziness, drowsiness, postural hypertension, coordination problems, weakness, tremors, respiratory depression, psychotropic effects, sleep disturbances, unwanted waitfulness, CNS stimulation, weight gain, appetite change, change in sexual function, constipation, dry mouth, gut erosion, gastric ulcerations, renal inflammation, cardiovascular hypertension, cardiovascular stimulation, hyperchlimina, not going into public, chest pain, stress incontinence, or any combination thereof.
21. The composition according to embodiments 1-20, wherein the antitussive activity reduces a symptom associated with a coughing condition.
22. The composition according to embodiment 21, wherein the antitussive activity reduces a symptom associated with a coughing condition by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%.
23. The composition according to embodiment 21, wherein the symptom includes the frequency of a cough, the severity of a cough, the volume or noise level of a cough, hoarseness, sore throat, breathing difficulty, respiratory congestion, wheezing, respiratory constriction, respiratory inflammation, muscle spasms associated with a cough, phlegm production, fainting, insomnia, vomiting, subconjunctival hemorrhage (red eye), cough defecation, cough urination, abdominal hernia, pelvic hernia, costochondritis, or lower rib fracture.
24. The composition according to embodiments 1-23, wherein the antitussive activity suppresses a vagal nerve function associated with a cough.
25. The composition according to embodiment 24, wherein the antitussive activity suppresses a vagal nerve function associated with a cough by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%.
26. The composition according to embodiments 1-25, wherein the antitussive activity suppresses a central nerve function associated with a cough.
27. The composition according to embodiment 26, wherein the antitussive activity suppresses a central nerve function associated with a cough by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%.
28. The composition according to embodiments 1-27, wherein the antitussive activity suppresses a peripheral nerve function associated with a cough.
29. The composition according to embodiment 28, wherein the antitussive activity suppresses a peripheral nerve function associated with a cough by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%.
30. The composition according to embodiments 1-29, wherein the composition is formulated for inhalatory administration.
31. The composition according to embodiments 1-29, wherein the composition is formulated for oral administration.
32. The composition according to embodiments 1-3 or 17-31, wherein the composition includes a methylxanthine and a non-opiate antitussive agent.
33. The composition according to embodiment 32, wherein the composition includes about 1 mg/mL to about 1000 mg/mL of the methylxanthine and about 1 mg/mL to about 250 mg/mL of the non-opiate antitussive agent.
34. The composition according to embodiments 1-3 or 15-31, wherein the composition includes a methylxanthine and an opiate antitussive agent.
35. The composition according to embodiment 34, wherein the composition includes about 1 mg/mL to about 1000 mg/mL of the methylxanthine and about 0.1 mg/mL to about 75 mg/mL of the opiate antitussive agent.
36. The composition according to embodiments 1-3 or 15-31, wherein the composition includes a methylxanthine and a decongestant.
37. The composition according to embodiment 36, wherein the composition includes about 1 mg/mL to about 1000 mg/mL of the methylxanthine and about 0.1 mg/mL to about 6000 mg/mL of the decongestant.
38. The composition according to embodiments 1-3 or 15-31, wherein the composition includes a methylxanthine and an expectorant.
39. The composition according to embodiment 38, wherein the composition includes about 1 mg/mL to about 1000 mg/mL of the methylxanthine and about 0.1 mg/mL to about 6000 mg/mL of the expectorant.
40. The composition according to embodiments 1-3 or 15-31, wherein the composition includes a methylxanthine and a mucolytic agent.
41. The composition according to embodiment 40, wherein the composition includes about 1 mg/mL to about 1000 mg/mL of the methylxanthine and about 0.1 mg/mL to about 6000 mg/mL of the mucolytic agent.
42. The composition according to embodiments 1-3, 15, 16, or 19-31, wherein the composition includes a methylxanthine and an anti-histamine.
43. The composition according to embodiment 42, wherein the composition includes about 1 mg/mL to about 1000 mg/mL of the methylxanthine and about 0.1 mg/mL to about 100 mg/mL of the anti-histamine.
44. The composition according to embodiments 1-3 or 15-31, wherein the composition includes a methylxanthine and a NSAID.
45. The composition according to embodiment 44, wherein the composition includes about 1 mg/mL to about 1000 mg/mL of the methylxanthine and about 1 mg/mL to about 3200 mg/mL of the NSAID.
46. The composition according to embodiments 1-3 or 15-31, wherein the composition includes a methylxanthine and a neuropathic pain agent.

47. The composition according to embodiment 46, wherein the composition includes about 1 mg/mL to about 1000 mg/mL of the methylxanthine and about 0.1 mg/mL to about 8000 mg/mL of the neuropathic pain agent.
48. The composition according to embodiments 1-3 or 15-31, wherein the composition includes a methylxanthine and a terpene.
49. The composition according to embodiments 48, wherein the composition includes about 1 mg/mL to about 1000 mg/mL of the methylxanthine and about 0.01 mg/mL to about 200 mg/mL of the terpene.
50. The composition according to embodiments 1-3 or 15-31, wherein the composition includes a methylxanthine and an ACE inhibitor.
51. The composition according to embodiment 50, wherein the composition includes about 1 mg/mL to about 1000 mg/mL of the methylxanthine and about 0.1 mg/mL to about 450 mg/mL of the ACE inhibitor.
52. The composition of claim 1, wherein the composition includes a methylxanthine and an angiotensin II receptor antagonist.
53. The composition of claim 46, wherein the composition includes about 1 mg/mL to about 1000 mg/mL of the methylxanthine and about 0.1 mg/mL to about 450 mg/mL of the angiotensin II receptor antagonist.
54. A method of treating a coughing condition in an individual, the method comprising the step of administering a composition according to embodiments 1-53, wherein administration reduces a symptom associated with the coughing condition.
55. The method according to embodiment 54, wherein the coughing condition comprises an acute coughing condition.
56. The method according to embodiment 54, wherein the coughing condition comprises a subacute coughing condition.
57. The method according to embodiment 54, wherein the coughing condition comprises a chronic coughing condition.
58. The method according to embodiments 54-57, wherein the coughing condition comprises a non-productive coughing condition.
59. The method according to embodiments 54-57, wherein the coughing condition comprises a productive coughing condition.
60. The method according to embodiments 54-59, wherein the coughing condition comprises a cough associated with a disease or disorder.
61. The method according to embodiment 60, wherein the disease or disorder is an asthma, an atopic cough a bronchitis, a gastroesophageal reflux disease (GERD), an infection of the respiratory tract, an inflammation, a medication, a pollutant, a post-nasal drip, a smoking event, a vagal nerve irritation, a diseases of the external auditory canal, a lung disease, a lung tumor, a habit cough, a tic, a Tourette syndrome, a cardiovascular disease, or a post-infectious cough.
62. The method according to embodiment 61, wherein the lung disease includes a bronchiectasis, a cystic fibrosis, an interstitial lung disease, a sarcoidosis, or a COPD.
63. The method according to embodiment 61, wherein the cardiovascular disease includes a heart failure, a pulmonary infarction, or an aortic aneurysm.
64. The method according to embodiment 61, wherein the infection of the respiratory tract includes a cold, croup, pertussis, pneumonia, or tuberculosis.
65. The method according to embodiments 54-64, wherein administration of the pharmaceutical composition reduces an unwanted side.
66. The method according to embodiment 65, wherein the unwanted side includes sedation, cognitive fogging, dizziness, drowsiness, postural hypertension, coordination problems, weakness, tremors, respiratory depression, psychotropic effects, sleep disturbances, unwanted waitfulness, CNS stimulation, weight gain, appetite change, change in sexual function, constipation, dry mouth, gut erosion, gastric ulcerations, renal inflammation, cardiovascular hypertension, cardiovascular stimulation, hyperchlimina, not going into public, chest pain, stress incontinence, or any combination thereof.
67. The method according to embodiments 54-66, wherein the symptom includes coughing, hoarseness, sore throat, breathing difficulty, respiratory congestion, wheezing, respiratory constriction, respiratory inflammation, muscle spasms associated with a cough, phlegm production, fainting, insomnia, vomiting, subconjunctival hemorrhage (red eye), cough defecation, cough urination, abdominal hernia, pelvic hernia, costochondritis, lower rib fracture, or any combination thereof.
68. Use of a composition according to embodiments 1-53 in the manufacture of a medicament for the treatment of a coughing condition.
69. Use of a composition according to embodiments 1-53 in the treatment of a coughing condition.
70. The use according to embodiment 67 or 68, wherein the coughing condition comprises an acute coughing condition.
71. The use according to embodiment 67 or 68, wherein the coughing condition comprises a subacute coughing condition.
72. The use according to embodiment 67 or 68, wherein the coughing condition comprises a chronic coughing condition.
73. The use according to embodiments 67-72, wherein the coughing condition comprises a non-productive coughing condition.
74. The use according to embodiments 67-72, wherein the coughing condition comprises a productive coughing condition.
75. The use according to embodiments 67-74, wherein the coughing condition comprises a cough associated with a disease or disorder.
76. The use according to embodiment 75, wherein the disease or disorder is an asthma, an atopic cough a bronchitis, a gastroesophageal reflux disease (GERD), an infection of the respiratory tract, an inflammation, a medication, a pollutant, a post-nasal drip, a smoking event, a vagal nerve irritation, a diseases of the external auditory canal, a lung disease, a lung tumor, a habit cough, a tic, a Tourette syndrome, a cardiovascular disease, or a post-infectious cough.
77. The use according to embodiment 76, wherein the lung disease includes a bronchiectasis, a cystic fibrosis, an interstitial lung disease, a sarcoidosis, or a COPD.
78. The use according to embodiment 76, wherein the cardiovascular disease includes a heart failure, a pulmonary infarction, or an aortic aneurysm.
79. The use according to embodiment 76, wherein the infection of the respiratory tract includes a cold, croup, pertussis, pneumonia, or tuberculosis.
80. The use according to embodiments 67-79, wherein administration of the pharmaceutical composition reduces an unwanted side.

81. The use according to embodiment 80, wherein the unwanted side includes sedation, cognitive fogging, dizziness, drowsiness, postural hypertension, coordination problems, weakness, tremors, respiratory depression, psychotropic effects, sleep disturbances, unwanted waitfulness, CNS stimulation, weight gain, appetite change, change in sexual function, constipation, dry mouth, gut erosion, gastric ulcerations, renal inflammation, cardiovascular hypertension, cardiovascular stimulation, hyperchlimina, not going into public, chest pain, stress incontinence, or any combination thereof.

82. The use according to embodiment 80, wherein the symptom includes coughing, hoarseness, sore throat, breathing difficulty, respiratory congestion, wheezing, respiratory constriction, respiratory inflammation, muscle spasms associated with a cough, phlegm production, fainting, insomnia, vomiting, subconjunctival hemorrhage (red eye), cough defecation, cough urination, abdominal hernia, pelvic hernia, costochondritis, lower rib fracture, or any combination thereof.

EXAMPLES

The following non-limiting examples are provided for illustrative purposes only in order to facilitate a more complete understanding of representative embodiments now contemplated. These examples should not be construed to limit any of the embodiments described in the present specification, including those pertaining to the compounds, pharmaceutical compositions, or methods or uses of treating a coughing condition.

Example 1

Oral Administration of Theobromine

This example illustrates the antitussive activity of theobromine.

Nine male Dunkin Hartley guinea pigs (400-500 g, supplied by Harlan UK Ltd) were randomly allocated equally into one of three groups. Group 1 animals were administered vehicle only; Group 2 animals were orally dosed (volume 2 mL/kg) with 3 mg/kg of theobromine; Group 3 animals were orally dosed with 7 mg/kg of theobromine. All pre-treatments were administered 120 minutes prior to citric acid exposure. Individual guinea pigs were placed in an exposure chamber with an airflow of 2 L/min for 10 minutes prior to citric acid exposure to allow acclimatisation. Cough responses were induced by exposure to 1 M citric acid aerosol generated by an ultrasonic nebuliser at a nebulisation rate of 0.6 mL/min for 10 minutes. Coughs were counted throughout the 10 minute citric acid exposure and for a further 5 minute post-exposure recovery period.

The results of this study are shown in Table 1. The mean number of citric acid induced cough responses recorded in the vehicle treated guinea pigs was 28±3 coughs with a mean onset time for first cough of 66±18 seconds. In theobromine-treated animals there was a dose dependant decrease in the total number of coughs evoked by citric acid exposure as well as an increase in the onset time to the first cough. At the highest dose, the total number of coughs had been reduced to 18±3, while the onset to the first cough had been extended to 98±36 seconds.

TABLE 1

Cough Suppression of Theobromine

| Group[1] Treatment | Cough Events | |
|---|---|---|
| | Mean Number | Mean Onset Time |
| Group 1 vehicle (p.o.) | 28 ± 3 | 66 ± 18 sec |
| Group 2 3 mg/kg theobromine (p.o.) | 25 ± 4 | 73 ± 17 sec |
| Group 3 7 mg/kg theobromine (p.o.) | 18 ± 3 | 98 ± 36 sec |

[1]n = 3 guinea pigs per group.

Example 2

Oral and Intratracheal Administration of Theobromine

This example illustrates the antitussive activity of theobromine.

Thirty-six male Dunkin Hartley guinea pigs (350-550 g, supplied by Harlan UK Ltd) were randomly allocated equally into one of six groups. Group 1 animals were administered vehicle only; Group 2 animals were intraperonteneally dosed (volume 2 mL/kg) with 25 mg/kg of codeine; Group 3 animals were orally dosed (volume 2 mL/kg) with 30 mg/kg of theobromine; Group 4 animals were intra-tracheally dosed with 3 mg/kg of theobromine; Group 5 animals were intra-tracheally dosed with 10 mg/kg of theobromine; and Group 6 animals were intra-tracheally dosed with 30 mg/kg of theobromine. All pre-treatments were administered 30 minutes prior to citric acid exposure. Individual guinea pigs were placed in an exposure chamber with an airflow of 2 L/min for 10 minutes prior to citric acid exposure to allow acclimatisation. Cough responses were induced by exposure to 1 M citric acid aerosol generated by an ultrasonic nebuliser at a nebulisation rate of 0.6 mL/min for 10 minutes. Coughs were counted throughout the 10 minute citric acid exposure and for a further 5 minute post-exposure recovery period.

The results of this study are shown in Table 2. The mean number of citric acid induced cough responses recorded in the vehicle treated guinea pigs was 26±4 coughs with a mean onset time for first cough of 71±26 seconds. The level of response was significantly reduced to 5±1 coughs in codeine-treated animals and the onset to the first cough was significantly extended to 337±51 seconds. Pre-treatment with theobromine (30 mg/kg, p.o.) also caused a significant reduction to the number of citric acid induced coughs (12±2), although the onset of the first cough was not significantly increased when compared to the control animals (126±20 seconds c.f. 71±26 seconds). Local administration (i.t.) of theobromine also had a significant dose dependant effect on the total number of coughs, reducing the number of coughs at a dose of 30 mg/kg of theobromine to 6±1. Indeed at the doses of 10 mg/kg (i.t.) theobromine caused a similar degree of cough suppression to that observed at 30 mg/kg (p.o.) theobromine (10.3±2 c.f. 12±2). It was also evident with increasing concentration of intra-tracheally administered theobromine, that there was an increase to the onset of the first cough which was significantly increased with a dose of 30 mg/kg to 210±22 seconds.

TABLE 2

Cough Suppression of Theobromine

| | | Cough Events | |
|---|---|---|---|
| Group[1] | Treatment | Mean Number | Mean Onset Time |
| Group 1 | vehicle (p.o.) | 26 ± 4 | 71 ± 26 sec |
| Group 2 | 25 mg/kg codeine (i.p.) | 5 ± 1** | 337 ± 51 sec |
| Group 3 | 30 mg/kg theobromine (p.o.) | 12 ± 2** | 126 ± 20 sec |
| Group 4 | 3 mg/kg theobromine (i.t.) | 17 ± 2* | 115 ± 29 sec |
| Group 5 | 10 mg/kg theobromine (i.t.) | 10 ± 2** | 134 ± 18 sec |
| Group 6 | 30 mg/kg theobromine (i.t.) | 6 ± 1** | 210 ± 22 sec* |

[1]n = 6 guinea pigs per group.
**P < 0.01.
*P < 0.05.

TABLE 3

Cough Suppression of Theobromine and Non-Opiate Antitussive Agent

| | | Cough Events | |
|---|---|---|---|
| Group[1] | Treatment | Mean Number | Mean Onset Time |
| Group 1 | vehicle (p.o.) | 28 ± 5 | 52 ± 9 sec |
| Group 2 | 25 mg/kg codeine (i.p.) | 7 ± 2** | 170 ± 32 sec** |
| Group 3 | 10 mg/kg theobromine (p.o.) | 13 ± 2** | 139 ± 22 sec* |
| Group 4 | 10 mg/kg theobromine (p.o.) 10 mg/kg dextromethophan (p.o.) | 15 ± 3* | 115 ± 14 sec |
| Group 5 | 10 mg/kg theobromine (p.o.) 30 mg/kg dextromethophan (p.o.) | 11 ± 2** | 146 ± 23 sec* |

[1]n = 6 guinea pigs per group.
**P < 0.01.
*P < 0.05.

Example 3

Theobromine and a Non-Opiate Antitussive Agent

This example illustrates the antitussive activity of theobromine in combination with a non-opiate antitussive agent.

Thirty male Dunkin Hartley guinea pigs (400-500 g, supplied by Harlan UK Ltd) were randomly allocated equally into one of five groups. Group 1 animals were administered vehicle only; Group 2 animals were intraperoneteally dosed (volume 2 mL/kg) with 25 mg/kg of codeine; Group 3 animals were orally dosed (volume 2 mL/kg) with 10 mg/kg of theobromine; Group 4 animals were orally dosed with 10 mg/kg of theobromine and 10 mg/kg dextromethophan; and Group 5 animals were orally dosed with 10 mg/kg of theobromine and 30 mg/kg dextromethophan. Pre-treatments with theobromine were administered 120 minutes prior to citric acid exposure, whereas pre-treatments with dextromethophan or vehicle were administered 60 minutes prior to citric acid exposure. Pre-treatments with codeine were administered 30 minutes prior to citric acid exposure. Individual guinea pigs were placed in an exposure chamber with an airflow of 2 L/min for 10 minutes prior to citric acid exposure to allow acclimatisation. Cough responses were induced by exposure to 1 M citric acid aerosol generated by an ultrasonic nebuliser at a nebulisation rate of 0.6 mL/min for 10 minutes. Coughs were counted throughout the 10 minute citric acid exposure and for a further 5 minute post-exposure recovery period.

The results of this study are shown in Table 3. The mean number of citric acid induced cough responses recorded in the vehicle treated guinea pigs was 28±5 coughs with a mean onset time for first cough of 52±9 seconds. The level of response was significantly reduced to 7±2 coughs in codeine-treated animals and the onset to the first cough was significantly extended to 170±32 seconds. Pre-treatment with theobromine (10 mg/kg) also caused a significant reduction to the number of citric acid induced coughs (13±2), as well as an increase duration to the onset of the first cough (139±22 seconds). In combination with dextromethophan (10 mg/kg or 30 mg/kg), the inhibitory effect of theobromine on the citric acid-induced tussive activity was potentiated slightly with the higher dose both in respect to the total number of coughs (11±2 c.f. 13±2) and the onset time to the first cough (146±23 seconds c.f. 139±22 seconds).

Example 4

Theobromine and an Opiate Antitussive Agent

This example illustrates the antitussive activity of theobromine in combination with an opiate antitussive agent.

Thirty male Dunkin Hartley guinea pigs (400-500 g, supplied by Harlan UK Ltd) were randomly allocated equally into one of five groups. Group 1 animals were administered vehicle only; Group 2 animals were intraperoneteally dosed (volume 2 mL/kg) with 25 mg/kg of codeine; Group 3 animals were orally dosed (volume 2 mL/kg) with 7 mg/kg of theobromine; Group 4 animals were orally dosed with 7 mg/kg of theobromine and 8 mg/kg codeine; and Group 5 animals were orally dosed with 7 mg/kg of theobromine and 16 mg/kg codeine. Pre-treatments with theobromine were administered 120 minutes prior to citric acid exposure, whereas oral pre-treatments with codeine were administered 60 minutes prior to citric acid exposure. Intraperitoneal pre-treatments with codeine were administered 30 minutes prior to citric acid exposure. Vehicle animals were dosed at both 120 minutes and 60 minutes prior to citric acid exposure. Individual guinea pigs were placed in an exposure chamber with an airflow of 2 L/min for 10 minutes prior to citric acid exposure to allow acclimatisation. Cough responses were induced by exposure to 1 M citric acid aerosol generated by an ultrasonic nebuliser at a nebulisation rate of 0.6 mL/min for 10 minutes. Coughs were counted throughout the 10 minute citric acid exposure and for a further 5 minute post-exposure recovery period.

The results of this study are shown in Table 4. The mean number of citric acid induced cough responses recorded in the vehicle treated guinea pigs was 27±4 coughs with a mean onset time for first cough of 61±9 seconds. The level of response was significantly reduced to 6±1 coughs in codeine-treated animals and the onset to the first cough was significantly extended to 195±33 seconds. Pre-treatment with theobromine (7 mg/kg) also caused a reduction to the number of citric acid induced coughs (19±3), as well as an increase in duration to the onset of the first cough (91±13 seconds), although when compared to vehicle control animals these changes were not significant. However, once combined with codeine (8 mg/kg or 16 mg/kg), the inhibitory response of theobromine on the citric acid induced tussive activity was dose dependently potentiated. Indeed in combination with the highest dose of codeine (16 mg/kg) the total number of coughs were now significantly reduced to 4±1 (c.f 19±3 seen in animals treated with theobromine alone), and onset to the first cough was also significantly extended to 202±30 seconds (c.f. 91±13 seconds).

TABLE 4

Cough Suppression of Theobromine and Opiate Antitussive Agent

| Group[1] | Treatment | Cough Events | |
|---|---|---|---|
| | | Mean Number | Mean Onset Time |
| Group 1 | vehicle (p.o.) | 27 ± 4 | 61 ± 9 sec |
| Group 2 | 25 mg/kg codeine (i.p.) | 6 ± 1** | 195 ± 33 sec** |
| Group 3 | 7 mg/kg theobromine (p.o.) | 19 ± 3 | 91 ± 13 sec |
| Group 4 | 7 mg/kg theobromine (p.o.) 8 mg/kg codeine (p.o.) | 10 ± 2** | 147 ± 15 sec* |
| Group 5 | 7 mg/kg theobromine (p.o.) 16 mg/kg codeine (p.o.) | 4 ± 1** | 202 ± 30 sec** |

[1]n = 6 guinea pigs per group.
**$P < 0.01$.
*$P < 0.05$.

Example 5

Theobromine and a Decongestant

This example illustrates the antitussive activity of theobromine in combination with a decongestant.

Thirty male Dunkin Hartley guinea pigs (400-500 g, supplied by Harlan UK Ltd) were randomly allocated equally into one of five groups. Group 1 animals were administered vehicle only; Group 2 animals were intraperonteneally dosed (volume 2 mL/kg) with 25 mg/kg of codeine; Group 3 animals were orally dosed (volume 2 mL/kg) with 10 mg/kg of theobromine; Group 4 animals were orally dosed with 10 mg/kg of theobromine and 10 mg/kg pseudoephidrine; and Group 5 animals were orally dosed with 10 mg/kg of theobromine and 30 mg/kg pseudoephidrine. Pre-treatments with theobromine were administered 120 minutes prior to citric acid exposure, whereas oral pre-treatments with pseudoephidrine were administered 30 minutes prior to citric acid exposure. Intraperitoneal pre-treatments with codeine were administered 30 minutes prior to citric acid exposure. Vehicle animals were dosed at both 120 minutes and 30 minutes prior to citric acid exposure. Individual guinea pigs were placed in an exposure chamber with an airflow of 2 L/min for 10 minutes prior to citric acid exposure to allow acclimatisation. Cough responses were induced by exposure to 1 M citric acid aerosol generated by an ultrasonic nebuliser at a nebulisation rate of 0.6 mL/min for 10 minutes. Coughs were counted throughout the 10 minute citric acid exposure and for a further 5 minute post-exposure recovery period.

The results of this study are shown in Table 5. The mean number of citric acid induced cough responses recorded in the vehicle treated guinea pigs was 28±4 coughs with a mean onset time for first cough of 72±10 seconds. The level of response was significantly reduced to 6±1 coughs in codeine-treated animals and the onset to the first cough was significantly extended to 195±25 seconds. Pre-treatment with theobromine (10 mg/kg) also caused a significant reduction to the number of citric acid induced coughs (13±3), as well as an increase in duration to the onset of the first cough (156±15 seconds). In combination with pseudoephedrine (10 mg/kg and 30 mg/kg), the inhibitory response of BC1036 on the citric acid induced tussive activity, was potentiated slightly with the highest dose both in respect of total number of coughs (9±2 c.f. 13±3) and onset time to the first cough (170±15 seconds c.f. 156±15 seconds).

TABLE 5

Cough Suppression of Theobromine and Decongestant

| Group[1] | Treatment | Cough Events | |
|---|---|---|---|
| | | Mean Number | Mean Onset Time |
| Group 1 | vehicle (p.o.) | 28 ± 4 | 72 ± 10 sec |
| Group 2 | 25 mg/kg codeine (i.p.) | 6 ± 1** | 195 ± 25 sec** |
| Group 3 | 10 mg/kg theobromine (p.o.) | 13 ± 3** | 156 ± 15 sec** |
| Group 4 | 10 mg/kg theobromine (p.o.) 10 mg/kg pseudoephidrine (p.o.) | 12 ± 3** | 164 ± 17 sec** |
| Group 5 | 10 mg/kg theobromine (p.o.) 30 mg/kg pseudoephidrine (p.o.) | 9 ± 2** | 170 ± 15 sec** |

[1]n =6 guinea pigs per group.
**$P < 0.01$.

Example 6

Theobromine and an Antihistamine

This example illustrates the antitussive activity of theobromine in combination with an antihistamine.

Thirty male Dunkin Hartley guinea pigs (400-500 g, supplied by Harlan UK Ltd) were randomly allocated equally into one of five groups. Group 1 animals were administered vehicle only; Group 2 animals were intraperonteneally dosed (volume 2 mL/kg) with 25 mg/kg of codeine; Group 3 animals were orally dosed (volume 2 mL/kg) with 10 mg/kg of theobromine; Group 4 animals were orally dosed with 10 mg/kg of theobromine and 10 mg/kg chlorpheniramine; and Group 5 animals were orally dosed with 10 mg/kg of theobromine and 30 mg/kg chlorpheniramine. Pre-treatments with theobromine were administered 120 minutes prior to citric acid exposure, whereas oral pre-treatments with chlorpheniramine were administered 30 minutes prior to citric acid exposure. Intraperitoneal pre-treatments with codeine were administered 30 minutes prior to citric acid exposure. Vehicle animals were dosed at both 120 minutes and 30 minutes prior to citric acid exposure. Individual guinea pigs were placed in an exposure chamber with an airflow of 2 L/min for 10 minutes prior to citric acid exposure to allow acclimatisation. Cough responses were induced by exposure to 1 M citric acid aerosol generated by an ultrasonic nebuliser at a nebulisation rate of 0.6 mL/min for 10 minutes. Coughs were counted throughout the 10 minute citric acid exposure and for a further 5 minute post-exposure recovery period.

The results of this study are shown in Table 6. The mean number of citric acid induced cough responses recorded in the vehicle treated guinea pigs was 26±4 coughs with a mean onset time for first cough of 42±9 seconds. The level of response was significantly reduced to 5±1 coughs in codeine-treated animals and the onset to the first cough was significantly extended to 236±22 seconds. Pre-treatment with theobromine (10 mg/kg) also caused a significant reduction to the number of citric acid induced coughs (15±2), as well as an increase in duration to the onset of the first cough (103±15 seconds). In combination with chlorpheniramine (0.3 mg/kg and 1 mg/kg), the inhibitory response of theobromine on the citric acid induced tussive activity, was dose dependently potentiated. Indeed in combination with the highest dose of chlorpheniramine (1 mg/kg) the total number of coughs was reduced to 10±2 (c.f 15±2 seen in animals treated with theobromine alone), and onset to the first cough was extended to 130±11 seconds (c.f. 111±17 seconds).

TABLE 6

Cough Suppression of Theobromine and Antihistamine

| Group[1] | Treatment | Cough Events | |
|---|---|---|---|
| | | Mean Number | Mean Onset Time |
| Group 1 | vehicle (p.o.) | 26 ± 4 | 42 ± 9 sec |
| Group 2 | 25 mg/kg codeine (i.p.) | 5 ± 1** | 236 ± 22 sec** |
| Group 3 | 10 mg/kg theobromine (p.o.) | 15 ± 2** | 103 ± 15 sec* |
| Group 4 | 10 mg/kg theobromine (p.o.) 0.3 mg/kg chlorpheniramine (p.o.) | 12 ± 2** | 111 ± 17 sec* |
| Group 5 | 10 mg/kg theobromine (p.o.) 1 mg/kg chlorpheniramine (p.o.) | 10 ± 2** | 130 ± 11 sec** |

[1]n = 6 guinea pigs per group.
**$P < 0.01$.
*$P < 0.05$.

Example 7

Theobromine and an Expectorant

This example illustrates the antitussive activity of theobromine in combination with an expectorant.

Twenty-four male Dunkin Hartley guinea pigs (400-510 g, supplied by Harlan UK Ltd) were randomly allocated equally into one of four groups. Group 1 animals were administered vehicle only; Group 2 animals were orally dosed (volume 2 mL/kg) with 10 mg/kg of theobromine; Group 3 animals were orally dosed (volume 2 mL/kg) with 30 mg/kg guaifenesin; and Group 4 animals were orally dosed with 10 mg/kg of theobromine and 30 mg/kg guaifenesin. Pre-treatments with theobromine were administered 30 minutes prior to citric acid exposure, whereas pre-treatments with guaifenesin or vehicle were administered 60 minutes prior to citric acid exposure. Individual guinea pigs were placed in an exposure chamber with an airflow of 2 L/min for 10 minutes prior to citric acid exposure to allow acclimatisation. Cough responses were induced by exposure to 1 M citric acid aerosol generated by an ultrasonic nebuliser at a nebulisation rate of 0.6 mL/min for 10 minutes. Coughs were counted throughout the 10 minute citric acid exposure and for a further 5 minute post-exposure recovery period.

The results of this study are shown in Table 7. The mean number of citric acid induced cough responses recorded in the vehicle treated guinea pigs was 30±4 coughs with a mean onset time for first cough of 46±10 seconds. Pre-treatment with theobromine (10 mg/kg, p.o.) caused a significant (P<0.05) reduction to the number of citric acid induced coughs (15±3), as well as an increase duration to the onset of the first cough (126±12 seconds). In contrast, guaifenesin (30 mg/kg, p.o.) had no significant effect on the total number of coughs (28±3) evoked by citric acid exposure or on the onset of the first cough (52±10 seconds). In combination with guaifenesin (30 mg/kg, p.o.), the inhibitory effect of theobromine on the citric acid-induced tussive activity, showed a trend to be potentiated in respect to total number of coughs observed (13±3 c.f. 15±3), although such trend was not evident with regard to onset of the first cough (121±10 seconds c.f. 126±12 seconds).

TABLE 7

Cough Suppression of Theobromine and Expectorant

| Group[1] | Treatment | Cough Events | |
|---|---|---|---|
| | | Mean Number | Mean Onset Time |
| Group 1 | vehicle (p.o.) | 30 ± 4 | 46 ± 10 sec |
| Group 2 | 10 mg/kg theobromine (p.o.) | 15 ± 3** | 126 ± 12 sec** |
| Group 3 | 30 mg/kg guaifenesin (p.o.) | 28 ± 3 | 52 ± 10 sec |
| Group 4 | 10 mg/kg theobromine (p.o.) 30 mg/kg guaifenesin (p.o.) | 13 ± 3** | 121 ± 10 sec** |

[1]n = 6 guinea pigs per group.
**$P < 0.01$.

Example 8

Theobromine and a NSAID

This example illustrates the antitussive activity of theobromine in combination with a NSAID.

Thirty male Dunkin Hartley guinea pigs (400-500 g, supplied by Harlan UK Ltd) are randomly allocated equally into one of five groups. Group 1 animals are administered vehicle only; Group 2 animals are intra-peritoneally dosed (volume 2 mL/kg) with 25 mg/kg of codeine; Group 3 animals are orally dosed (volume 2 mL/kg) with 10 mg/kg of theobromine; Group 4 animals are orally dosed with 10 mg/kg of theobromine and 10 mg/kg ibuprofen; and Group 5 animals are orally dosed with 10 mg/kg of theobromine and 30 mg/kg ibuprofen; Group 6 animals are orally doses with 30 mg/kg of ibuprofen only. Pre-treatments with theobromine are administered 120 minutes prior to citric acid exposure, whereas pre-treatments with ibuprofen or vehicle are administered 60 minutes prior to citric acid exposure. Pre-treatments with codeine are administered 30 minutes prior to citric acid exposure. Individual guinea pigs are placed in an exposure chamber with an airflow of 2 L/min for 10 minutes prior to citric acid exposure to allow acclimatisation. Cough responses are induced by exposure to 1 M citric acid aerosol generated by an ultrasonic nebuliser at a nebulisation rate of 0.6 mL/min for 10 minutes. Coughs are counted throughout the 10 minute citric acid exposure and for a further 5 minute post-exposure recovery period.

The mean number of citric acid induced cough responses recorded in the vehicle treated guinea pigs is 30±5 coughs with a mean onset time for first cough of 55±7 seconds. The level of response is significantly reduced to 8±3 coughs in codeine-treated animals and the onset to the first cough was significantly extended to 150±32 seconds. Pre-treatment with theobromine (10 mg/kg) also caused a significant reduction to the number of citric acid induced coughs (15±3), as well as small increase duration to the onset of the first cough (113±15 seconds). In combination with both doses of ibuprofen (10 mg/kg or 30 mg/kg), the inhibitory effect of theobromine on the citric acid-induced tussive activity was potentiated substantially with both the lower and higher doses both in respect to the total number of coughs (11±2 c.f. 9±1) and the onset time to the first cough (143±19 seconds c.f. 122±20 seconds). Ibuprofen on its own has very little effect on total number of coughs (22±6) or on the onset time to the first cough (70±5 seconds).

Example 9

Theobromine and an Neuropathic Pain Agent

This example illustrates the antitussive activity of theobromine in combination with an neuropathic pain agent.

Thirty male Dunkin Hartley guinea pigs (400-500 g, supplied by Harlan UK Ltd) are randomly allocated equally into one of five groups. Group 1 animals are administered vehicle only; Group 2 animals are intra-peritoneally dosed (volume 2 mL/kg) with 25 mg/kg of codeine; Group 3 animals are orally dosed (volume 2 mL/kg) with 10 mg/kg of theobromine; Group 4 animals are orally dosed with 10 mg/kg of theobromine and 30 mg/kg gabapentin; and Group 5 animals are orally dosed with 10 mg/kg of theobromine and 60 mg/kg gabapentin; Group 6 animals are orally doses with 60 mg/kg of gabapentin only. Pre-treatments with theobromine are administered 120 minutes prior to citric acid exposure, whereas pre-treatments with gabapentin or vehicle are administered 60 minutes prior to citric acid exposure. Pre-treatments with codeine are administered 30 minutes prior to citric acid exposure. Individual guinea pigs are placed in an exposure chamber with an airflow of 2 L/min for 10 minutes prior to citric acid exposure to allow acclimatisation. Cough responses are induced by exposure to 1 M citric acid aerosol generated by an ultrasonic nebuliser at a nebulisation rate of 0.6 mL/min for 10 minutes. Coughs are counted throughout the 10 minute citric acid exposure and for a further 5 minute post-exposure recovery period.

The mean number of citric acid induced cough responses recorded in the vehicle treated guinea pigs is 31±6 coughs with a mean onset time for first cough of 58±9 seconds. The level of response is significantly reduced to 9±4 coughs in codeine-treated animals and the onset to the first cough was significantly extended to 161±31 seconds. Pre-treatment with theobromine (10 mg/kg) also caused a significant reduction to the number of citric acid induced coughs (14±4), as well as small increase duration to the onset of the first cough (108±19 seconds). In combination with gabapentin (30 mg/kg or 60 mg/kg), the inhibitory effect of theobromine on the citric acid-induced tussive activity was potentiated significantly with the higher dose both in respect to the total number of coughs (13±2 c.f. 6±2) and the onset time to the first cough (89±20 seconds c.f. 142±18 seconds). Gabapentin on its own has very little effect on total number of coughs (24±8) or on the onset time to the first cough (90±6 seconds).

Example 10

Theobromine and a Terpene

This example illustrates the antitussive activity of theobromine in combination with a terpene.

Thirty male Dunkin Hartley guinea pigs (400-500 g, supplied by Harlan UK Ltd) are randomly allocated equally into one of five groups. Group 1 animals are administered vehicle only; Group 2 animals are intra-peritoneally dosed (volume 2 mL/kg) with 25 mg/kg of codeine; Group 3 animals are orally dosed (volume 2 mL/kg) with 10 mg/kg of theobromine; Group 4 animals are orally dosed with 10 mg/kg of theobromine and 0.3 mg/kg peppermint oil; and Group 5 animals are orally dosed with 10 mg/kg of theobromine and 1 mg/kg ibuprofen; Group 6 animals are orally doses with 1 mg/kg of peppermint oil only. Pre-treatments with theobromine and peppermint oil are administered 120 minutes prior to citric acid exposure. Pre-treatments with codeine are administered 30 minutes prior to citric acid exposure. Individual guinea pigs are placed in an exposure chamber with an airflow of 2 L/min for 10 minutes prior to citric acid exposure to allow acclimatisation. Cough responses are induced by exposure to 1 M citric acid aerosol generated by an ultrasonic nebuliser at a nebulisation rate of 0.6 mL/min for 10 minutes. Coughs are counted throughout the 10 minute citric acid exposure and for a further 5 minute post-exposure recovery period.

The mean number of citric acid induced cough responses recorded in the vehicle treated guinea pigs is 27±5 coughs with a mean onset time for first cough of 62±7 seconds. The level of response is significantly reduced to 6±2 coughs in codeine-treated animals and the onset to the first cough was significantly extended to 170±28 seconds. Pre-treatment with theobromine (10 mg/kg) also caused a significant reduction to the number of citric acid induced coughs (14±5), as well as small increase duration to the onset of the first cough (120±23 seconds). In combination with peppermint oil (0.3 mg/kg or 1 mg/kg), the inhibitory effect of theobromine on the citric acid-induced tussive activity was potentiated substantially only with the higher dose both in respect to the total number of coughs (15±3 c.f. 6±2) and the onset time to the first cough (115±17 seconds c.f. 130±25 seconds). Peppermint oil on its own has no effect on total number of coughs (26±10) or on the onset time to the first cough (75±8 seconds).

Example 11

Theobromine and an ACE Inhibitor

This example illustrates the antitussive activity of theobromine in combination with an ACE inhibitor.

Thirty male Dunkin Hartley guinea pigs (400-500 g, supplied by Harlan UK Ltd) are randomly allocated equally into one of five groups. Group 1 animals are administered vehicle only; Group 2 animals are intra-peritoneally dosed (volume 2 mL/kg) with 25 mg/kg of codeine; Group 3 animals are orally dosed (volume 2 mL/kg) with 30 mg/kg of theobromine; Group 4 animals are orally dosed with 30 mg/kg of captopril; and Group 5 animals are orally dosed with 30 mg/kg of theobromine and 30 mg/kg captopril. Pre-treatments with theobromine and captopril are administered 120 minutes prior to citric acid exposure. Pre-treatments with codeine are administered 30 minutes prior to citric acid exposure. Individual guinea pigs are placed in an exposure chamber with an airflow of 2 L/min for 10 minutes prior to citric acid exposure to allow acclimatisation. Cough responses are induced by exposure to 1 M citric acid aerosol generated by an ultrasonic nebuliser at a nebulisation rate of 0.6 mL/min for 10 minutes. Coughs are counted throughout the 10 minute citric acid exposure and for a further 5 minute post-exposure recovery period.

The mean number of citric acid induced cough responses recorded in the vehicle treated guinea pigs is 29±9 coughs with a mean onset time for first cough of 66±8 seconds. The level of response is significantly reduced to 7±3 coughs in codeine-treated animals and the onset to the first cough was significantly extended to 170±28 seconds. Pre-treatment with theobromine (30 mg/kg) also caused a significant reduction to the number of citric acid induced coughs (10±4), as well as small increase duration to the onset of the first cough (125±22 seconds). Pretreatment with captopril (30 mg/kg), substantially increased the protussive effect of citric acid, with total number of coughs (45±12) and the shortened the onset time to the first cough (34±12 seconds). Combining the captopril and theobromine reduced the total number of coughs compared to the captopril alone group (18±10) and lengthened the onset time to the first cough (70±12 seconds).

Example 12

Treatment of a Coughing Condition

A 26 year old woman complains of coughing all the time. After routine history and physical examination, a physician diagnosis the woman with a coughing condition associated with smoking. The woman is treated by inhalatory administration a pharmaceutical composition comprising theobromine and dextromethophan as disclosed herein taken four times daily. Alternatively, the woman may be treated by oral administration a pharmaceutical composition comprising theobromine and dextromethophan as disclosed herein taken twice times daily. The patient's condition is monitored and after about 2 days from treatment, the woman indicates she is experiencing decreased coughing episodes. At two and four month check-ups, the woman indicates that she is still taking the medication and is still experiencing decreased episodes of coughing. This decrease in coughing episodes indicates successful treatment with the pharmaceutical composition disclosed herein.

In a similar manner, a pharmaceutical composition comprising theobromine and any of the therapeutic compounds disclosed herein, such as, e.g., a non-opiate antitussive, an opiate antitussive, a decongestant, an expectorant, a mucolytic agent, an anti-histamine, a NSAID, a neuropathic pain agent, a terpene, or any combination thereof, will be formulated into a pharmaceutical composition and administered to the patient as described above.

A 78 year old man complains of coughing all the time. After routine history and physical examination, a physician diagnosis the man with a coughing condition associated with tuberculosis. The man is treated by inhalatory administration a pharmaceutical composition comprising theobromine and codeine as disclosed herein taken four times daily. Alternatively, the man may be treated by oral administration a pharmaceutical composition comprising theobromine and codeine as disclosed herein taken twice times daily. The patient's condition is monitored and after about 2 days from treatment, the man indicates he is experiencing decreased coughing episodes. At two and four month check-ups, the man indicates that he is still taking the medication and is still experiencing decreased episodes of coughing. This decrease in coughing episodes indicates successful treatment with the pharmaceutical composition disclosed herein.

In a similar manner, a pharmaceutical composition comprising theobromine and any of the therapeutic compounds disclosed herein, such as, e.g., a non-opiate antitussive, an opiate antitussive, a decongestant, an expectorant, a mucolytic agent, an anti-histamine, a NSAID, a neuropathic pain agent, a terpene, or any combination thereof, will be formulated into a pharmaceutical composition and administered to the patient as described above.

A 58 year old male complains of coughing due to breathing difficulty. After routine history and physical examination, a physician diagnosis the man with a coughing condition associated with a chronic obstructive pulmonary disease (COPD). The man is treated by inhalatory administration a pharmaceutical composition comprising theobromine and pseudoephidrine as disclosed herein taken four times daily. Alternatively, the man may be treated by oral administration a pharmaceutical composition comprising theobromine and pseudoephidrine as disclosed herein taken twice times daily. The patient's condition is monitored and after about 2 days from treatment, the man indicates he is experiencing decreased coughing episodes. At two and four month check-ups, the man indicates that he is still taking the medication and is still experiencing decreased episodes of coughing. This decrease in coughing episodes indicates successful treatment with the pharmaceutical composition disclosed herein.

In a similar manner, a pharmaceutical composition comprising theobromine and any of the therapeutic compounds disclosed herein, such as, e.g., a non-opiate antitussive, an opiate antitussive, a decongestant, an expectorant, a mucolytic agent, an anti-histamine, a NSAID, a neuropathic pain agent, a terpene, or any combination thereof, will be formulated into a pharmaceutical composition and administered to the patient as described above.

A 18 year old woman complains of coughing and stuffed-up nose. After routine history and physical examination, a physician diagnosis the woman with a coughing condition associated with a respiratory tract infection. The woman is treated by inhalatory administration a pharmaceutical composition comprising theobromine and ibuprofen as disclosed herein taken four times daily. Alternatively, the woman may be treated by oral administration a pharmaceutical composition comprising theobromine and ibuprofen as disclosed herein taken twice times daily. The patient's condition is monitored and after about 2 days from treatment, the woman indicates she is experiencing decreased coughing episodes. At one and two week check-ups, the woman indicates that she is not coughing and feels great. This decrease in coughing episodes indicates successful treatment with the pharmaceutical composition disclosed herein.

In a similar manner, a pharmaceutical composition comprising theobromine and any of the therapeutic compounds disclosed herein, such as, e.g., a non-opiate antitussive, an opiate antitussive, a decongestant, an expectorant, a mucolytic agent, an anti-histamine, a NSAID, a neuropathic pain agent, a terpene, or any combination thereof, will be formulated into a pharmaceutical composition and administered to the patient as described above.

A 47 year old woman complains of coughing and runny nose. After routine history and physical examination, a physician diagnosis the woman with a coughing condition associated with an allergy. The woman is treated by inhalatory administration a pharmaceutical composition comprising theobromine and chlorpheniramine as disclosed herein taken four times daily. Alternatively, the woman may be treated by oral administration a pharmaceutical composition comprising theobromine and chlorpheniramine as disclosed herein taken twice times daily. The patient's condition is monitored and after about 2 days from treatment, the woman indicates she is experiencing decreased coughing episodes. At one and two month check-ups, the woman indicates that she is not coughing and does not have a runny nose. This decrease in coughing episodes indicates successful treatment with the pharmaceutical composition disclosed herein.

In a similar manner, a pharmaceutical composition comprising theobromine and any of the therapeutic compounds disclosed herein, such as, e.g., a non-opiate antitussive, an opiate antitussive, a decongestant, an expectorant, a mucolytic agent, an anti-histamine, a NSAID, a neuropathic pain agent, a terpene, or any combination thereof, will be formulated into a pharmaceutical composition and administered to the patient as described above.

A 34 year old male complains of coughing due to breathing difficulty. After routine history and physical examination, a physician diagnosis the man with a coughing condition associated with a chest cold. The man is treated by inhalatory administration a pharmaceutical composition comprising theobromine and guaifenesin as disclosed herein taken four times daily. Alternatively, the man may be treated by oral administration a pharmaceutical composition comprising theobromine and guaifenesin as disclosed herein taken twice times daily. The patient's condition is monitored and after about 2 days from treatment, the man indicates he is experiencing decreased coughing episodes. At one and two week check-ups, the man indicates that indicates that his chest is cleared and his is not coughing. This decrease in coughing episodes indicates successful treatment with the pharmaceutical composition disclosed herein.

In a similar manner, a pharmaceutical composition comprising theobromine and any of the therapeutic compounds disclosed herein, such as, e.g., a non-opiate antitussive, an opiate antitussive, a decongestant, an expectorant, a mucolytic agent, an NSAID, a neuropathic pain agent, a terpene, or any combination thereof, will be formulated into a pharmaceutical composition and administered to the patient as described above.

A 67 year old male complains of coughing due to a medication including an ACE inhibitor for hypertension. After routine history and physical examination, a physician diagnosis the man with a coughing condition that is a side-effect of his ACE inhibitor medication. The man is treated by inhalatory administration a pharmaceutical composition comprising theobromine as disclosed herein in conjunction with his ACE inhibitor medication. Alternatively, the man may be treated by oral administration a pharmaceutical composition comprising theobromine as disclosed herein in conjunction with his ACE inhibitor medication. Alternatively, the man may be treated by inhalatory administration a pharmaceutical composition comprising theobromine and the ACE inhibitor as disclosed herein taken four times daily. Alternatively, the man may be treated by oral administration a pharmaceutical composition comprising theobromine and the ACE inhibitor as disclosed herein taken twice times daily. The patient's condition is monitored and after about 2 days from treatment, the man indicates he is experiencing decreased coughing episodes. At two and four month check-ups, the man indicates that he is still taking the medication and is still experiencing decreased episodes of coughing. This decrease in coughing episodes indicates successful treatment with the pharmaceutical composition disclosed herein.

A 73 year old male complains of coughing due to a medication including an angiotensin II receptor antagonist for hypertension. After routine history and physical examination, a physician diagnosis the man with a coughing condition that is a side-effect of his ACE inhibitor medication. The man is treated by inhalatory administration a pharmaceutical composition comprising theobromine as disclosed herein in conjunction with his angiotensin II receptor antagonist medication. Alternatively, the man may be treated by oral administration a pharmaceutical composition comprising theobromine as disclosed herein in conjunction with his angiotensin II receptor antagonist medication. Alternatively, the man may be treated by inhalatory administration a pharmaceutical composition comprising theobromine and the angiotensin II receptor antagonist as disclosed herein taken four times daily. Alternatively, the man may be treated by oral administration a pharmaceutical composition comprising theobromine and the angiotensin II receptor antagonist as disclosed herein taken twice times daily. The patient's condition is monitored and after about 2 days from treatment, the man indicates he is experiencing decreased coughing episodes. At two and four month check-ups, the man indicates that he is still taking the medication and is still experiencing decreased episodes of coughing. This decrease in coughing episodes indicates successful treatment with the pharmaceutical composition disclosed herein.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The invention claimed is:

1. An oral pharmaceutical composition comprising 0.5 mg/mL to 10 mg/mL of Theobromine, 0.25 mg/mL to 7.5 mg/mL of Diphenhydramine, and 0.1 mg/mL to 5 mg/mL of Phenylephrine, wherein the pharmaceutical composition does not include a non-opiate antitussive agent and wherein the therapeutically-effective amount of the theobromine is at least 60 mg/day and at most 150 mg/day.

2. The oral pharmaceutical composition according to claim 1, wherein the oral pharmaceutical composition comprises 0.5 mg/mL to 6 mg/mL of Theobromine, 0.5 mg/mL to 5 mg/mL of Diphenhydramine, and 0.1 mg/mL to 2 mg/mL of Phenylephrine.

3. The oral pharmaceutical composition according to claim 2, wherein the oral pharmaceutical composition comprises 1 mg/mL to 3 mg/mL of Theobromine, 1 mg/mL to 3 mg/mL of Diphenhydramine, and 0.1 mg/mL to 1 mg/mL of Phenylephrine.

4. The oral pharmaceutical composition according to claim 3, wherein the oral pharmaceutical composition comprises 2 mg/mL of Theobromine, 1.25 mg/mL of Diphenhydramine, and 0.5 mg/mL of Phenylephrine.

5. A method of treating cough due to a cold, the method comprising the step of administering a therapeutically-effective amount of the oral pharmaceutical composition of claim 1.

6. The method according to claim 5, wherein the oral pharmaceutical composition comprises 0.5 mg/mL to 6 mg/mL of Theobromine, 0.5 mg/mL to 5 mg/mL of Diphenhydramine, and 0.1 mg/mL to 2 mg/mL of Phenylephrine.

7. The method according to claim 6, wherein the oral pharmaceutical composition comprises 1 mg/mL to 3 mg/mL of, 1 mg/mL to 3 mg/mL of Diphenhydramine, and 0.1 mg/mL to 1 mg/mL of Phenylephrine.

8. The method according to claim 7, wherein the oral pharmaceutical composition comprises 2 mg/mL of Theobromine, 1.25 mg/mL of Diphenhydramine, and 0.5 mg/mL of Phenylephrine.

9. The method according to claim 5, wherein the therapeutically-effective amount of the oral pharmaceutical composition comprises between 60 mg/day and 150 mg/day of Theobromine, 20 mg/day and 100 mg/day of Diphenhydramine, and 5 mg/day and 50 mg/day of Phenylephrine.

10. The method according to claim 9, wherein the therapeutically-effective amount of the oral pharmaceutical composition comprises between 60 mg/day and 120 mg/day of Theobromine, 37.5 mg/day and 75 mg/day of Diphenhydramine, and 15 mg/day and 30 mg/day of Phenylephrine.

* * * * *